(12) United States Patent
Eckert

(10) Patent No.: US 9,512,129 B2
(45) Date of Patent: Dec. 6, 2016

(54) SOLID FORMS COMPRISING 1-ETHYL-7-(2-METHYL-6-(1H-1,2,4-TRIAZOL-3-YL)PYRIDIN-3-YL)-3,4-DIHYDROPYRAZINO[2,3-B]PYRAZIN-2(1H)-ONE AND A COFORMER

(71) Applicant: Signal Pharmaceuticals, LLC, San Diego, CA (US)

(72) Inventor: Jeffrey Eckert, Hazlet, NJ (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 54 days.

(21) Appl. No.: 14/686,856

(22) Filed: Apr. 15, 2015

(65) Prior Publication Data

US 2015/0299207 A1 Oct. 22, 2015

Related U.S. Application Data

(60) Provisional application No. 61/980,111, filed on Apr. 16, 2014.

(51) Int. Cl.
*A61K 31/4985* (2006.01)
*C07D 241/38* (2006.01)
*C07D 487/04* (2006.01)
*A61K 9/14* (2006.01)
*A61K 9/20* (2006.01)

(52) U.S. Cl.
CPC .............. *C07D 487/04* (2013.01); *A61K 9/145* (2013.01); *A61K 9/2018* (2013.01); *A61K 9/2054* (2013.01)

(58) Field of Classification Search
CPC ......................... A61K 31/4985; C07D 241/38
USPC ........................ 514/249; 544/350; 546/268.1; 548/266.4
See application file for complete search history.

(56) References Cited

U.S. PATENT DOCUMENTS

| | | | |
|---|---|---|---|
| 3,507,866 A | 4/1970 | Jones et al. | |
| 3,567,725 A | 3/1971 | Grabowski et al. | |
| 4,294,836 A | 10/1981 | Lesher et al. | |
| 4,294,837 A | 10/1981 | Lesher et al. | |
| 4,309,537 A | 1/1982 | Lesher et al. | |
| 4,317,909 A | 3/1982 | Lesher et al. | |
| 4,898,872 A | 2/1990 | Campbell et al. | |
| 4,963,561 A | 10/1990 | Lesher et al. | |
| 5,424,311 A | 6/1995 | Billhardt-Troughton | |
| 5,869,659 A | 2/1999 | Stolle et al. | |
| 6,031,105 A | 2/2000 | Wright | |
| 6,093,728 A | 7/2000 | McMahon et al. | |
| 6,372,740 B1 | 4/2002 | Murata et al. | |
| 6,566,367 B2 | 5/2003 | Bakthavatchalam et al. | |
| 6,791,006 B2 | 9/2004 | Nezu et al. | |
| 6,800,436 B1 | 10/2004 | Jenne et al. | |
| 6,855,723 B2 | 2/2005 | McMahon et al. | |
| 7,608,622 B2 | 10/2009 | Liu et al. | |
| 8,372,976 B2 | 2/2013 | Mortensen et al. | |
| 8,383,634 B2 | 2/2013 | Mortensen et al. | |
| 8,492,381 B2 | 7/2013 | Perrin-Ninkovic et al. | |
| 2003/0036652 A1 | 2/2003 | Bakthavatchalam et al. | |
| 2003/0162968 A1 | 8/2003 | Cirillo et al. | |
| 2004/0023921 A1 | 2/2004 | Hong et al. | |
| 2004/0063658 A1 | 4/2004 | Roberts et al. | |
| 2004/0097485 A1 | 5/2004 | Burkitt et al. | |
| 2005/0009737 A1 | 1/2005 | Clark | |
| 2006/0004014 A1 | 1/2006 | Hoffmann et al. | |
| 2006/0135511 A1 | 6/2006 | Burgey | |
| 2006/0142269 A1 | 6/2006 | Dykes | |
| 2006/0211702 A1 | 9/2006 | Oslob et al. | |
| 2007/0036793 A1 | 2/2007 | Hardie et al. | |
| 2007/0112005 A1 | 5/2007 | Chen et al. | |
| 2008/0194019 A1 | 8/2008 | Cantley et al. | |
| 2008/0214580 A1 | 9/2008 | Neagu et al. | |
| 2009/0023724 A1 | 1/2009 | Mortensen et al. | |
| 2009/0042890 A1 | 2/2009 | Mortensen et al. | |
| 2009/0069289 A1 | 3/2009 | Neagu et al. | |
| 2009/0163545 A1 | 6/2009 | Goldfard | |
| 2009/0181963 A1 | 7/2009 | Dehnhardt et al. | |
| 2009/0281075 A1 | 11/2009 | Roughton et al. | |
| 2010/0144738 A1 | 6/2010 | Bornmann et al. | |
| 2010/0216781 A1 | 8/2010 | Perrin-Ninkovic et al. | |
| 2010/0249122 A1 | 9/2010 | Kalman | |
| 2011/0137028 A1 | 6/2011 | Harris et al. | |
| 2011/0257167 A1 | 10/2011 | Chopra et al. | |
| 2011/0318336 A1 | 12/2011 | Petricoin, III et al. | |
| 2012/0028972 A1 | 2/2012 | Wong et al. | |
| 2013/0102613 A1 | 4/2013 | Xu et al. | |
| 2013/0142873 A1 | 6/2013 | Assaf et al. | |
| 2013/0158023 A1 | 6/2013 | Ning et al. | |
| 2013/0225518 A1 | 8/2013 | Xu et al. | |
| 2013/0245026 A1 | 9/2013 | Xu et al. | |
| 2013/0245027 A1 | 9/2013 | Xu et al. | |

(Continued)

FOREIGN PATENT DOCUMENTS

| | | |
|---|---|---|
| CA | 2 458 699 | 3/2003 |
| DE | 262 026 | 11/1988 |
| EP | 0 385 850 | 9/1990 |
| JP | 63275582 | 5/1987 |
| JP | 2001048882 | 2/2001 |

(Continued)

OTHER PUBLICATIONS

Barlin 1982, "Purine analogs as amplifiers of phleomycin. VII. Some 1H-inidazo[4,5-b]pyrazines and related compound," Australian Journal of Chemistry, vol. 35:2299-2306.

(Continued)

*Primary Examiner* — Douglas M Willis

(74) *Attorney, Agent, or Firm* — Jones Day

(57) ABSTRACT

Provided herein are formulations, processes, solid forms and methods of use relating to 1-ethyl-7-(2-methyl-6-(1H-1,2,4-triazol-3-yl)pyridin-3-yl)-3,4-dihydropyrazino[2,3-b]pyrazin-2(1H)-one.

14 Claims, 46 Drawing Sheets

(56) References Cited

U.S. PATENT DOCUMENTS

| | | | |
|---|---|---|---|
| 2013/0245028 A1 | 9/2013 | Xu et al. |
| 2013/0245029 A1 | 9/2013 | Xu et al. |
| 2013/0245254 A1 | 9/2013 | Harris et al. |
| 2014/0113905 A1 | 4/2014 | Xu et al. |
| 2014/0314673 A1 | 10/2014 | Raymon et al. |
| 2014/0314674 A1 | 10/2014 | Raymon et al. |
| 2014/0314751 A1 | 10/2014 | Hege et al. |
| 2014/0314752 A1 | 10/2014 | Lopez-Girona et al. |
| 2014/0314753 A1 | 10/2014 | Hege et al. |
| 2014/0315848 A1 | 10/2014 | Raymon et al. |
| 2014/0315900 A1 | 10/2014 | Raymon et al. |
| 2014/0315907 A1 | 10/2014 | Raymon et al. |
| 2014/0315908 A1 | 10/2014 | Menon et al. |

FOREIGN PATENT DOCUMENTS

| | | |
|---|---|---|
| JP | 2002100363 | 4/2002 |
| JP | 2002167387 | 6/2002 |
| WO | WO 03/032989 | 4/1903 |
| WO | WO 2004/042002 | 5/1904 |
| WO | WO 99/16438 | 4/1999 |
| WO | WO 99/28320 | 6/1999 |
| WO | WO 99/28459 | 6/1999 |
| WO | WO 00/73306 | 12/2000 |
| WO | WO 02/048152 | 6/2002 |
| WO | WO 02/076954 | 10/2002 |
| WO | WO 03/032989 | 4/2003 |
| WO | WO 03/072557 | 9/2003 |
| WO | WO 03/093290 | 11/2003 |
| WO | WO 2004/042002 | 5/2004 |
| WO | WO 2004/048365 | 6/2004 |
| WO | WO 2004/065378 | 8/2004 |
| WO | WO 2004/076454 | 9/2004 |
| WO | WO 2004/078754 | 9/2004 |
| WO | WO 2004/085409 | 10/2004 |
| WO | WO 2004/096797 | 11/2004 |
| WO | WO 2005/003147 | 1/2005 |
| WO | WO 2005/021519 | 3/2005 |
| WO | WO 2005/120511 | 12/2005 |
| WO | WO 2006/001266 | 1/2006 |
| WO | WO 2006/018182 | 2/2006 |
| WO | WO 2006/030031 | 3/2006 |
| WO | WO 2006/036883 | 4/2006 |
| WO | WO 2006/045828 | 5/2006 |
| WO | WO 2006/046031 | 5/2006 |
| WO | WO 2006/050076 | 5/2006 |
| WO | WO 2006/065703 | 6/2006 |
| WO | WO 2006/087530 | 8/2006 |
| WO | WO 2006/090167 | 8/2006 |
| WO | WO 2006/090169 | 8/2006 |
| WO | WO 2006/091737 | 8/2006 |
| WO | WO 2006/108103 | 10/2006 |
| WO | WO 2007/044698 | 4/2007 |
| WO | WO 2007/044729 | 4/2007 |
| WO | WO 2007/044813 | 4/2007 |
| WO | WO 2007/047754 | 4/2007 |
| WO | WO 2007/060404 | 5/2007 |
| WO | WO 2007/066099 | 6/2007 |
| WO | WO 2007/066102 | 6/2007 |
| WO | WO 2007/080382 | 7/2007 |
| WO | WO 2007/125321 | 11/2007 |
| WO | WO 2007/129044 | 11/2007 |
| WO | WO 2007/129052 | 11/2007 |
| WO | WO 2007/129161 | 11/2007 |
| WO | WO 2007/135398 | 11/2007 |
| WO | WO 2008/016669 | 2/2008 |
| WO | WO 2008/023161 | 2/2008 |
| WO | WO 2008/032027 | 3/2008 |
| WO | WO 2008/032028 | 3/2008 |
| WO | WO 2008/032033 | 3/2008 |
| WO | WO 2008/032036 | 3/2008 |
| WO | WO 2008/032060 | 3/2008 |
| WO | WO 2008/032064 | 3/2008 |
| WO | WO 2008/032072 | 3/2008 |
| WO | WO 2008/032077 | 3/2008 |
| WO | WO 2008/032089 | 3/2008 |
| WO | WO 2008/032091 | 3/2008 |
| WO | WO 2008/051493 | 5/2008 |
| WO | WO 2008/064093 | 5/2008 |
| WO | WO 2008/115974 | 9/2008 |
| WO | WO 2008/140947 | 11/2008 |
| WO | WO 2009/007748 | 1/2009 |
| WO | WO 2009/007750 | 1/2009 |
| WO | WO 2009/007751 | 1/2009 |
| WO | WO 2009/052145 | 4/2009 |
| WO | WO 2009/102986 | 8/2009 |
| WO | WO 2010/006072 | 1/2010 |
| WO | WO 2010/062571 | 6/2010 |
| WO | WO 2010/068483 | 6/2010 |
| WO | WO 2011/031965 | 3/2011 |
| WO | WO 2011/053518 A1 | 5/2011 |
| WO | WO 2011/079114 | 6/2011 |
| WO | WO 2011/097333 | 8/2011 |

OTHER PUBLICATIONS

Beresnev et al., 2000, "Interaction of 5-methoxy-1,2,4-traizines with uras as a new route to 6-azapurines," Medeleev Commu., vol. 2:58-59.
Bergmann et al., 1963, "2-Phenylpurines, their chemical and enzumological reactivity," J. Chem Org., pp. 3729-3735.
Booth et al., 1992, "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. 2119-26.
Booth et al., 1995, "Synthesis of [1α, 2β,3α-2,3-bis(benzylox3rmethypcyclobutl]imidazol-5-amines: important precursors to cyclobut-A derivatives," J. Chem Society, Perkin Tranactions 1: Organic and Bio-Organic Chemistry, vol. 6, pp. 669-675.
Booth et al., 2001, "The Reactions of Diaminomaleonitrile with Isocyanates and Either Aldehydes or Ketones Revisited," J. Org Chem, vol. 66:8436-8441.
Booth, et al., 1994, "Synthesis of 4- and 5-Disubstituted 1-Benzylimidazoles, Important Precursors of Purine Analogs," J. of Heterocyclic of Chemistry, vol. 31(2):345-50.
Caira et al., 1998, "Crystalline Polymorphism of Organic Compounds," *Topics in Current Chemistry*, Jan. 1, 1998, pp. 163-208, vol. 198, Springer, Berlin, DE.
Carretero et al. 2010, "Integrative Genomic and Proteomic Analyses Indentity Targets for Lkb1-Deficient Metastatic Lung Tumors," Cancer Cell, vol. 17(6): 547-559.
Chupakhin et al., 2001, "A simple one pot synthesis of condensed 1,2,4-triazines by using the tandem $A_N$-$S_N$ ipso and $S_N^H$—$S_N$ ipso reactions," J. of Heterocyclic Chemistry, vol. 38(4):901-907.
Cohen, P. 2001, "The role of protein phosphorylation in human health and disease," Eur. J. Biochem,vol. 268:5001-5010.
Cohen, P. 2002, "Protein kinases—the major drug targets of the twenty-first century?" Nature Reviews/Drug Discovery, vol. 1:309-315.
Cohen, 2005, *Protein Kinase Inhibitors for the Treatment of Disease: The Promise and the Problems*, Handbook of Experimental Pharmacology, Springer Berlin Heidelberg, 167:1-7.
Coish, et al., 2006, "Small molecule inhibitors of IKK kinase activity," Expert Opin. Ther. Patents, vol. 16(1):1-12.
Crofts et al., 1997 "Metabolism of 2-amino-1-methyl-6-phenylimidazo [4,5-b]pyridine (PhIP) by human cytochrome P4501B1," Carcinogenesis, vol. 18(9):1793-1798.
Dang et al., 1999, "Efficient synthesis of purines and purine nucelosides via an inverse electron demand diels—alder reaction," J. Am Chem Soc., vol. 121(24):5833-5834.
Database Caplus Online Chemical Abstracts Service, Columbus, Ohio, Database Accession No. 1951:49974 (XP-002472261) (1951).
Database Caplus Online Chemical Abstracts Service, Columbus, Ohio, Database Accession No. 1978:433195 (XP-002472262) (1978).
Database Caplus Online Chemical Abstracts Service, Columbus, Ohio, Database Accession No. 1966:26849 (XP-002472263) (1965).

(56) References Cited

OTHER PUBLICATIONS

Dornow et al., 1957, "Synthese von2-Oxy-imidazolo-(5',4':2,3)-pyridinen)," Arch Pharm. vol. 290, pp. 20-31 (w/English language abstract).

Dzierba et al., 2004, "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47, pp. 5783-5790.

Fabbro et al., 2002, "Protein kinases as targets for anticancer agents: from inhibitors to useful drugs," Pharmacol Ther., 93(2-3):79-98.

Farhadi et al., 2006, "The role of protein kinase C isoforms in modulating injury and repair of the intestinal barrier," J. Pharm Exp. Ther., vol. 316(1):1-7.

Frandsen et al., 1992, "Reaction of the N2-acetoxy derivative of 2-amino-l-methyl-6-phenylimidazo[4,5,b] pyridine . . . ," Carcinogenesis, vol. 13(4):629-635.

Furniss et al., 1989, "Vogel's Textbook of Practical Organic Chemistry Fifth Edition," 1989, p. 132-136, Longman.

Gao et al., 2010, "LKB1 inhibits lung cancer progression through lysyl oxidase and extracellular matrix remodeling," Proceedings of the National Academy of Sciences, vol. 107(44): 18892-18897.

Gao et al.: 2011, "LKB1 in lung cancerigenesis: a serine/threonine kinase as tumor suppressor," Protein & Cell, Gaodeng Jiaoyu Chubanshe, China, vol. 2(2): 99-107.

Georgakis and Younes, 2006, "From rapi nui to rapamycin: targeting PI3K/Akt/mTOR for cancer therapy," Expert Rev. Anticancer Ther., vol. 6(1):131-140.

Gini et al., 2013, "The mTOR Kinase Inhibitors, CC214-1 and CC214-2, Preferentially Block the Growth of EGFRvIII-Activated Glioblastomas," Clin Cancer Res 2013;19:5722-5732.

Grimmiger et al., 2010, " Targeting non-malignant disorders with tyrosine kinase inhibitors," Nat. Rev. Drug Disc., 9(12):956-970.

Hamad, 2001, "A new synthesis of 4-cyano-1,3-dihydro-2-oxo-2$H$-imidazole-5-($N^1$-tosyl)carboxamide: Reactive precursor for thiopurine analogues," J of Heterocyclic Chemistry, vol. 38(4):939-944.

Hernan et al., "De novo germline mutation in the serine-threonine kinase STK11/LKB1 gene associated with Peutz-Jeghers syndrome," Clin Genet., 66(1):58-62.

Huang et al., 2010, "Genetic and epigenetic silencing of SCARA5 may contribute to human hepatocellular carcinoma by activating FAK signaling," Journal of Clinical Investigation, American Society for Clinical investigation, vol. 120(1): 223-241.

Inge et al., 2009, "Expression of LKB1 tumor suppressor in non-small cell lung cancer determines sensitivity to 2-deoxyglucose," Journal of Thoracic and Cardiovascular Surgery, vol. 137(3): 580-586.

Irie et al., 2005, "Toward the development of new medicinal leads with selectivity for protein kinase C isozymes," The Chemical Record, vol. 5:185-195.

Itoh et al., 2004, "A novel practical synthesis of C-2-arylpurines," Advanced Synthesis & Catalysis, vol. 346:1859-1867.

Ji et al., 2007, "LKB1 modulates lung cancer differentiation and metastasis," Nature, 448(7155):807-810.

Jones et al., 1973, "6-Substituted-5-chloro-1,3-dihydro-2H-imidazo(4,5-b)pyrazin-2-ones with hypotensive activity," J. Med. Chem., vol. 16(5):537-542.

Kazaoka et al., 2003, "Synthesis of 6-substituted 9-benzyl-8-hydroxypurines with potential interferon-indcuing activity," Chemical & Pharmaceutical Bulletin, vol. 51(5):608-611.

Killday et al., 2001, "Microxine, a new cdc2 kinase inhibitor from the Australian marine sponge *Microxina* species," J. of Natural Products, vol. 64(4):525-526.

Mahoney et al., 2009, "LKB1/KRAS mutant lung cancers constitute a genetic subset of NSCLC with increased sensitivity to MAPK and mTOR signalling inhibition," Br J Cancer, 100(2):370-375.

Minehan et al., 2000, "Molecular recognition of DNA by Hoechst Benzimidazoles: Exploring beyond theopyrrole-imidazole-hydroxypyrrole polyamide-pairing code," Helvitica Chima Acta, vol. 83(9):2197-2213.

Nagashima et al., 2004, "Solution-Phase parallel synthesis of an N-Alkylated dihydropteridinone library from fluorous amino acids," J of Comb. Chemistry, vol. 6(6):942-949.

Park et al., 2000, "A novel mechanism of TRAF signaling revealed by structural and functional analyses of the TRADD-TRAF2 interaction," Cell, vol. 101:777-787.

Patani et al., 1998, "Bioisosterim: A rational approach in drug design," Chemical Reviews, vol. 96:3147-3176.

PCT Annex Communication Relating to the Results of the Partial International Search issued in connection with PCT/US2012/049281,filed Aug. 2, 2012.

PCT International Search Report issued in connection with PCT/US2012/049281, filed Aug. 2, 2012.

PCT Written Opinion of the International Searching Authority issued in connection with PCT/US2012/049281, filed Aug. 2, 2012.

Registry File Document for RN 863501-03-5, 863502-39-0 and others (Sep. 20, 2005).

Seela et al., 2004, "Product Class 17: Purines," Science of Synthesis, vol. 16, pp. 945-1108.

Shaw et al., 2004, "The LKB1 tumor suppressor negativiely regulates mTOR signaling," Cancer Cell, vol. 6(1): 91-99.

Shaw et al., 2009, "LKB1 and AMP-activated protein kinase control of mTOR signalling and growth," Acta. Physiol (Oxf.) 196(1):65-80.

Shoji et al. 2012, "Genotype-dependent efficacy of a dual PI3K/mTOR inhibitor, NVP-BEZ235, and an mTOR inhibitor, RAD001, in endometrial carcinomas." *PloS one* 7.5, 2012, e37431.

Singh et al., 1994, "Novel cAMP PDE III Inhibitors: Imidazo[4,5-b]pyridin-2(3H)-ones and Thiazolo[4,5-b]pyridin-2(3h)-ones and Their Analogs," J. Med. Chem, vol. 37(2):248-54.

Sridhar et al., 2000, "Protein kinases as therapeutic targets," Pharm. Res., 17(11):1345-1353.

Wallace 2008, "Palladium-catalyzed synthesis of quinoxaline derivatives," Tetrahedron, vol. 64:9675-9684.

Wei et al., 2009, "Chemopreventive efficacy of rapamycin on Peutz-Jeghers syndrome in a mouse model," Cancer Lett., 277(2):149-154.

Westover et al., 1981, "Synthesis and antiviral activity of certain 9-β-D-Riofuranoaylpurine-6-carboxamides," J.Med. Chem., vol. 24(8):941-46.

Wingo et al., 2009, "Somatic LKB1 mutations promote cervical cancer progression," PloS One, 4(4):1-8.

Yoneda et al., 1976, "A transformationof 7-azapteridines into 6-azapurines (Imidazo[4,5-e]-as-triazines)," Heterocycles, vol. 4(9):1503-1508.

Yoneda et al., 1978, "Synthesis of imadazo[4,5-e]-as-triazine (6-Azapurine) Deriviatives," Chem & Pharm Bulletin, vol. 26(10):3154-3160.

Yuan et al., 2009, "Targeting tumorigenesis: development and use of mTOR inhibitors in cancer therapy," Journal of Hematology & Oncology, Biomed Central Ltd., London UK, vol. 2(1): 45.

Zaki et al., 2007, "The synthesis of imidazol[4,5-$d$]pyridines from a substituted imidazole and acyl or sulfonyl acetonitrile," Tetrahedron, vol. 63(18):3745-3753.

Zhong et al., 2006, "LKB1 mutation in large cell carcinoma of the lung," Cancer Lung, vol. 53(3):285-294.

Chandramouli et al., 2012, "Review on Cocrystal as an approach with Newer Implications in Pharmaceutical Field". Int. J. of Med. Chem. and Anal. 2:91-100.

SOLID FORMS COMPRISING 1-ETHYL-7-(2-METHYL-6-(1H-1,2,4-TRIAZOL-3-YL)PYRIDIN-3-YL)-3,4-DIHYDROPYRAZINO[2,3-B]PYRAZIN-2(1H)-ONE AND A COFORMER

This application claims the benefit of U.S. Provisional Application No. 61/980,111, filed Apr. 16, 2014, the entire contents of which are incorporated herein by reference.

1. FIELD

Provided herein are solid forms comprising 1-ethyl-7-(2-methyl-6-(1H-1,2,4-triazol-3-yl)pyridin-3-yl)-3,4-dihydropyrazino[2,3-b]pyrazin-2(1H)-one and a coformer. Pharmaceutical compositions comprising such solid forms (e.g., cocrystals) and methods of use for treating, preventing, and managing various disorders are also provided herein.

2. BACKGROUND

The identification and selection of a solid form of a pharmaceutical compound is complex, given that a change in a solid form may affect a variety of physical and chemical properties, which may provide benefits or drawbacks in processing, formulation, stability and bioavailability, among other important pharmaceutical characteristics. Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, potential solid forms of a pharmaceutical compound include single-component and multiple-component solids. Single-component solids consist essentially of the pharmaceutical compound in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., Solid State Chemistry of Drugs, (1999) SSCI, West Lafayette). The importance of discovering polymorphs was underscored by the case of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417).

Additional diversity among the potential solid forms of a pharmaceutical compound may arise from the possibility of multiple-component solids. Crystalline solids comprising two or more ionic species are termed salts (see, e.g., Handbook of Pharmaceutical Salts: Properties, Selection and Use, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, cocrystals and clathrates, among others (see, e.g., S. R. Byrn et al., Solid State Chemistry of Drugs, (1999) SSCI, West Lafayette). Moreover, multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*: 3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Deliver Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

Cocrystals are crystalline molecular complexes of two or more non-volatile compounds bound together in a crystal lattice by non-ionic interactions. Pharmaceutical cocrystals are cocrystals of a therapeutic compound, e.g., an active pharmaceutical ingredient (API), and one or more non-volatile compound(s) (referred to herein as coformer). A coformer in a pharmaceutical cocrystal is typically selected from non-toxic pharmaceutically acceptable molecules, such as, for example, food additives, preservatives, pharmaceutical excipients, or other APIs. In recent years, pharmaceutical cocrystals have emerged as a possible alternative approach to enhance physicochemical properties of drug products. The variety of possible solid forms creates potential diversity in physical and chemical properties for a given pharmaceutical compound.

The compound chemically named 1-ethyl-7-(2-methyl-6-(1H-1,2,4-triazol-3-yl)pyridin-3-yl)-3,4-dihydropyrazino[2,3-b]pyrazin-2(1H)-one and tautomers thereof (collectively referred to herein as "Compound 1") are disclosed in U.S. Pat. No. 8,110,578, issued on Feb. 7, 2012, and International Pub. No. WO 2010/062571, the entireties of each of which are incorporated by reference herein.

Citation or identification of any reference in Section 2 of this application is not to be construed as an admission that the reference is prior art to the present application.

3. SUMMARY

Provided herein are solid forms (e.g., cocrystal forms or mixtures thereof) comprising the Compound of formula 1:

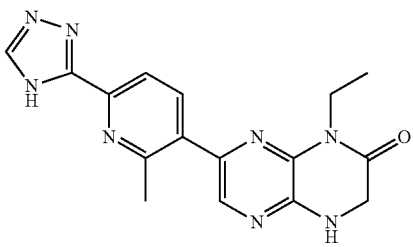

having the name 1-ethyl-7-(2-methyl-6-(1H-1,2,4-triazol-3-yl)pyridin-3-yl)-3,4-dihydropyrazino[2,3-b]pyrazin-2(1H)-one, including tautomers thereof, and a coformer. Also provided are methods of preparing, isolating, and characterizing the solid forms.

Also provided herein are pharmaceutical compositions and single unit dosage forms, which comprise one or more solid forms provided herein.

A solid form is provided which comprises (a) 1-ethyl-7-(2-methyl-6-(1H-1,2,4-triazol-3-yl)pyridin-3-yl)-3,4-dihydropyrazino[2,3-b]pyrazin-2(1H)-one; and (b) a coformer. The coformer is benzoic acid, fumaric acid, gentisic acid, nicotinamide, succinic acid or mandelic acid. The solid form is substantially crystalline. The solid form can substantially be a cocrystal. The solid form is greater than 80% by weight, greater than 90% by weight, greater than 95% by weight, greater than 97% by weight, or greater than 99% by weight of a cocrystal. The solid form is substantially physically pure. The solid form is substantially free of other solid forms of 1-ethyl-7-(2-methyl-6-(1H-1,2,4-triazol-3-yl)pyridin-3-yl)-3,4-dihydropyrazino[2,3-b]pyrazin-2(1H)-one. The solid form further comprises amorphous 1-ethyl-7-(2-methyl-6-(1H-1,2,4-triazol-3-yl)pyridin-3-yl)-3,4-dihydropyrazino[2,3-b]pyrazin-2(1H)-one. The solid form of is substantially crystalline.

Also provided is a pharmaceutical composition comprising the solid forms provided herein. The pharmaceutical composition can further comprise a pharmaceutically acceptable excipient or carrier. The pharmaceutical composition can be a single unit dosage form. The pharmaceutical composition can be a tablet or a capsule.

Further provided herein are crystal forms comprising the compound of formula (I):

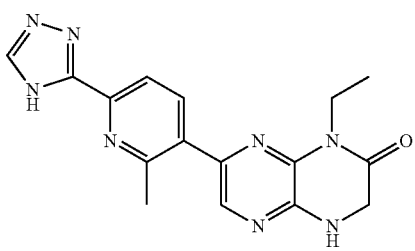

One crystal form provided herein has an X-ray powder diffraction pattern comprising characteristic X-ray powder diffraction peaks at a two-theta angle of approximately 7.78, 13.02 and 25.02 degrees. The X-ray powder diffraction pattern can further comprise characteristic X-ray powder diffraction peaks at a two-theta angle of approximately 13.54, 24.26 and 26.1 degrees. The crystal form can have a thermogravimetric analysis thermogram comprising a total mass loss of approximately 5% of the total mass of the crystal form when heated from about 25° C. to about 300° C. The crystal form can have a single differential thermal analysis thermogram comprising an endotherm between about 35° C. and about 105° C. with a maximum at approximately 89° C. when heated from about 25° C. to about 300° C. The crystal form can be methanol solvated. The crystal form can be substantially pure.

Another crystal form provided herein has characteristic X-ray powder diffraction peaks at a two-theta angle of approximately 7.66, 10.42 and 27.02 degrees. The X-ray powder diffraction pattern can further comprise characteristic X-ray powder diffraction peaks at a two-theta angle of approximately 14.02, 17.46 and 24.06 degrees. The crystal can have a thermogravimetric analysis thermogram comprising a total mass loss of approximately 5.1% of the total mass of the crystal form when heated from about 25° C. to about 300° C. The crystal form can have a single differential thermal analysis thermogram comprising an endotherm between about 35° C. and about 135° C. with a maximum at approximately 115° C. when heated from about 25° C. to about 300° C. The single differential thermal analysis thermogram can further comprise an endotherm with a maximum at approximately 177° C. The crystal form can be methanol and water solvated. The crystal form can be substantially pure.

Still another crystal form provided herein has an X-ray powder diffraction pattern comprising characteristic X-ray powder diffraction peaks at a two-theta angle of approximately 9.06, 26.06 and 28.7 degrees. The X-ray powder diffraction pattern can further comprise characteristic X-ray powder diffraction peaks at a two-theta angle of approximately 22.74, 24.58 and 26.9 degrees. The crystal form can have a thermogravimetric analysis thermogram comprising a total mass loss of approximately 4.2% of the total mass of the crystal form when heated from about 25° C. to about 300° C. The crystal form can have a single differential thermal analysis thermogram comprising an endotherm between about 35° C. and about 105° C. with a maximum at approximately 93° C. when heated from about 25° C. to about 300° C. The single differential thermal analysis thermogram can further comprise an endotherm with a maximum at approximately 178.1° C. The crystal form can be methanol solvated. The crystal form can be substantially pure.

Another further crystal form provided herein has an X-ray powder diffraction pattern comprising characteristic X-ray powder diffraction peaks at a two-theta angle of approximately 13.34, 22.9 and 25.18 degrees. The X-ray powder diffraction pattern can further comprise characteristic X-ray powder diffraction peaks at a two-theta angle of approximately 7.58, 12.22 and 24.22 degrees. The crystal form can have a thermogravimetric analysis thermogram comprising a total mass loss of approximately 1.7% of the total mass of the crystal form when heated from about 25° C. to about 300° C. The crystal form can have a single differential thermal analysis thermogram comprising an endotherm between about 110° C. and about 150° C. with a maximum at approximately 101.3° C. when heated from about 25° C. to about 300° C. The single differential thermal analysis thermogram can further comprise an endotherm with a maximum at approximately 141.6° C. The crystal form can be water solvated. The crystal form can be substantially pure.

Furthermore provided is a crystal form which has characteristic X-ray powder diffraction peaks at a two-theta angle of approximately 17.42, 24.7 and 28.34 degrees. The X-ray powder diffraction pattern can further comprise characteristic X-ray powder diffraction peaks at a two-theta angle of approximately 10.82, 19.3 and 30.86 degrees. The crystal form can have a thermogravimetric analysis thermogram comprising a total mass loss of approximately 1.6% of the total mass of the crystal form when heated from about 25° C. to about 300° C. The crystal form can have a single differential thermal analysis thermogram comprising an endotherm between about 35° C. and about 155° C. with a maximum at approximately 180° C. when heated from about 25° C. to about 300° C. The single differential thermal analysis thermogram can further comprise an endotherm with a maximum at approximately 236° C. The crystal form can be water solvated. The crystal form can be substantially pure.

Still furthermore, a crystal form provided herein has characteristic X-ray powder diffraction peaks at a two-theta angle of approximately 11.5, 23.42 and 25.06 degrees. The X-ray powder diffraction pattern can further comprise characteristic X-ray powder diffraction peaks at a two-theta angle of approximately 14.9, 24.18 and 26.1 degrees. The crystal form can have a thermogravimetric analysis thermogram comprising a total mass loss of approximately 3.8% of the total mass of the crystal form when heated from about 25° C. to about 300° C. The crystal form can have a single differential thermal analysis thermogram comprising an endotherm between about 35° C. and about 145° C. with a maximum at approximately 89° C. when heated from about 25° C. to about 300° C. The single differential thermal analysis thermogram can further comprise an endotherm with a maximum at approximately 200° C. The crystal form can be THF solvated or water solvated. The crystal form can be substantially pure.

A further a crystal form provided herein has characteristic X-ray powder diffraction peaks at a two-theta angle of approximately 7.62, 10.54 and 26.7 degrees. The X-ray powder diffraction pattern can further comprise characteristic X-ray powder diffraction peaks at a two-theta angle of approximately 13.82, 19.34 and 24.26 degrees. The crystal form can have a thermogravimetric analysis thermogram comprising a total mass loss of approximately 3.8% of the total mass of the crystal form when heated from about 25° C. to about 300° C. The crystal form can have a single differential thermal analysis thermogram comprising an endotherm between about 35° C. and about 145° C. with a maximum at approximately 108.8° C. when heated from about 25° C. to about 300° C. The single differential thermal analysis thermogram can further comprise an endotherm with a maximum at approximately 164.3° C. The crystal form can be water solvated. The crystal form can be substantially pure.

Another further crystal form provided herein has characteristic X-ray powder diffraction peaks at a two-theta angle of approximately 6.94, 13.82 and 27.66 degrees. The X-ray powder diffraction pattern can further comprise characteristic X-ray powder diffraction peaks at a two-theta angle of approximately 22.18, 26.22 and 26.98 degrees. The crystal form can have a thermogravimetric analysis thermogram comprising a total mass loss of approximately 4.2% of the total mass of the crystal form when heated from about 25° C. to about 300° C. The crystal form can have a single differential thermal analysis thermogram comprising an endotherm between about 35° C. and about 145° C. with a maximum at approximately 118.7° C. when heated from about 25° C. to about 300° C. The crystal form can be water solvated. The crystal form can be substantially pure.

All the solid forms and the pharmaceutical compositions provided herein can be used as a medicament. In certain embodiments, solid forms of Compound 1 are useful for treating or preventing cancer and conditions treatable or preventable by inhibition of a kinase pathway, for example, the mTOR/PI3K/Akt pathway. All the solid form and the pharmaceutical composition can be used in methods for treating or preventing cancer, an inflammatory condition, an immunological condition, a neurodegenerative disease, diabetes, obesity, a neurological disorder, an age-related disease, a cardiovascular condition, or a conditions treatable or preventable by inhibition of a kinase pathway. The methods comprise administering an effective amount of a solid form or a pharmaceutical composition to a subject in need thereof. The kinase pathway is the TOR kinase pathway.

All the solid forms and the pharmaceutical compositions provided herein can be used in methods for achieving a Response Evaluation Criteria in Solid Tumors (RECIST 1.1) of complete response, partial response or stable disease in a subject. The methods comprise administering an effective amount of a solid form or a pharmaceutical composition to a subject having a solid tumor.

All the solid forms and the pharmaceutical compositions provided herein can be used in methods for improving International Workshop Criteria (IWC) for NHL, International Uniform Response Criteria for Multiple Myeloma (IURC), Eastern Cooperative Oncology Group Performance Status (ECOG) or Response Assessment for Neuro-Oncology (RANO) Working Group for GBM. The methods comprise administering an effective amount of a solid form or a pharmaceutical composition to a subject in need thereof.

The present embodiments can be understood more fully by reference to the detailed description and examples, which are intended to exemplify non-limiting embodiments.

4. BRIEF DESCRIPTION OF THE DRAWINGS

5. DETAILED DESCRIPTION

5.1 Definitions

Figure 1:
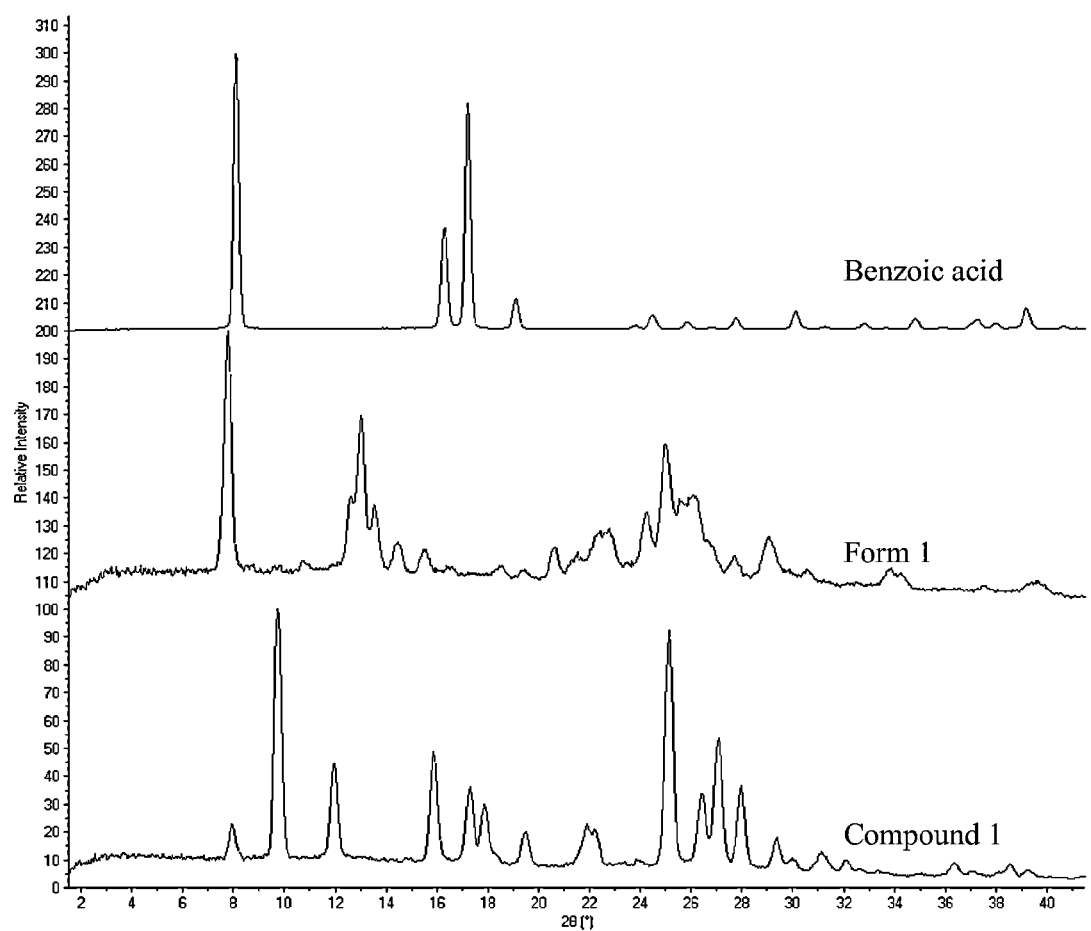
FIG. 1 depicts an X-ray powder diffractogram stack plot of Compound 1, Form 1 and benzoic acid (from bottom to top).

As used herein, and in the specification and the accompanying claims, the indefinite articles "a" and "an" and the definite article "the" include plural as well as single referents, unless the context clearly indicates otherwise.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, IR or Raman spectroscopy or XRPD; indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of an XRPD peak position may vary by up to ±0.2 degrees two theta while still describing the particular XRPD peak.

As used herein, and unless otherwise specified, a crystalline that is "pure," i.e., substantially free of other crystalline or amorphous forms, contains less than about 10% by weight of one or more other crystalline or amorphous forms, less than about 5% by weight of one or more other crystalline or amorphous forms, less than about 3% by weight of one or more other crystalline or amorphous forms, or less than about 1% by weight of one or more other crystalline or amorphous forms.

As used herein and unless otherwise indicated, the term "substantially pure" when used to describe a polymorph of a compound, i.e. a crystal form or an amorphous form of a compound, means a crystal form or an amorphous form of the compound that comprises that crystal form or amorphous form and is substantially free of other polymorphs of the compound. A substantially pure crystal form is no less than about 95% pure, no less than about 96% pure, no less than about 97% pure, no less than about 98% pure, no less than about 98.5% pure, no less than about 99% pure, no less than about 99.5% pure, or no less than about 99.8% pure. In certain embodiments, a form that is substantially pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other polymorphs on a weight basis.

As used herein, and unless otherwise specified, a solid form that is "substantially physically pure" is substantially free from other solid forms. In certain embodiments, a crystal form that is substantially physically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

Unless otherwise specified, the terms "solvate" and "solvated," as used herein, refer to a solid form of a substance which contains solvent. The terms "hydrate" and "hydrated" refer to a solvate wherein the solvent is water. "Polymorphs of solvates" refer to the existence of more than one solid form for a particular solvate composition. Similarly, "polymorphs of hydrates" refer to the existence of more than one solid form for a particular hydrate composition. The term "desolvated solvate," as used herein, refers to a solid form of a substance which can be made by removing the solvent from a solvate. The terms "solvate" and "solvated," as used herein, can also refer to a solvate of a salt, cocrystal, or molecular complex. The terms "hydrate" and "hydrated," as used herein, can also refer to a hydrate of a salt, cocrystal, or molecular complex.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

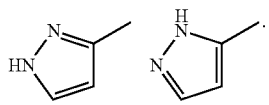

As readily understood by one skilled in the art, a wide variety of functional groups and other structures may exhibit tautomerism and all tautomers of Compound 1 are within the scope of the present invention.

Unless otherwise specified, the term "composition" as used herein is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

The term "solid form" refers to a physical form which is not predominantly in a liquid or a gaseous state. As used herein and unless otherwise specified, the term "solid form," when used herein to refer to Compound 1, refers to a physical form comprising Compound 1 which is not predominantly in a liquid or a gaseous state. A solid form may be a crystalline form or a mixture thereof. In certain embodiments, a solid form may be a liquid crystal. In certain embodiments, the term "solid forms comprising Compound 1" includes crystal forms comprising Compound 1. In certain embodiments, the solid form of Compound 1 is Form 1, Form 2, Form 3, Form 4, Form 5, Form 6, Form 7 and Form 8 or a mixture thereof.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, $23^{rd}$ ed., 1843-1844 (1995).

The term "crystal form" or "crystalline form" refers to a solid form that is crystalline. In certain embodiments, crystal forms include salts. In certain embodiments, a crystal form of a substance may be substantially free of amorphous forms and/or other crystal forms. In certain embodiments, a crystal form of a substance may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous forms and/or other crystal forms. In certain embodiments, a crystal form of a substance may be physically and/or chemically pure. In certain embodiments, a crystal form of a substance may be about 99%, about 98%, about 97%, about 96%, about 95%, about 94%, about 93%, about 92%, about 91%, or about 90% physically and/or chemically pure.

Unless otherwise specified, the terms "polymorph," "polymorphic form," "polymorphs," "polymorphic forms," and related terms herein refer to two or more crystal forms that consist essentially of the same molecule, molecules or ions. Different polymorphs may have different physical properties, such as, for example, melting temperatures, heats of fusion, solubilities, dissolution rates, and/or vibrational spectra as a result of a different arrangement or conformation of the molecules or ions in the crystal lattice. The differences in physical properties exhibited by polymorphs may affect pharmaceutical parameters, such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically a more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing; for example, one polymorph might be more likely to form solvates or might be difficult to filter and wash free of impurities (e.g., particle shape and size distribution might be different between polymorphs).

Unless otherwise specified, the term "cocrystal" as used herein, refers to a crystalline material comprised of Compound 1, including tautomers thereof, and one or more non-volative compounds bound together in a crystal lattice by non-covalent interactions.

Unless otherwise specified, the term "amorphous" or "amorphous form" means that the substance, component, or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In certain embodiments, an amorphous form of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous forms and/or crystal forms on a weight basis. In certain embodiments, an amorphous form of a substance may be physically and/or chemically pure. In certain embodiments, an amorphous form of a substance be about 99%, about 98%, about 97%, about 96%, about 95%, about 94%, about 93%, about 92%, about 91%, or about 90% physically and/or chemically pure.

"Treating" as used herein, means an alleviation, in whole or in part, of the disease or disorder, or symptoms associated with the disease or disorder, or slowing, or halting of further progression or worsening of the disease or disorder, or symptoms associated with the disease or disorder.

"Preventing" as used herein, means prevention of the onset, recurrence, or spread of the disease or disorder, or symptoms associated with the disorder or disease, in a patient at risk for developing the disease or disorder.

The term "effective amount" in connection with a solid form of Compound 1 means, in one embodiment, an amount capable of alleviating, in whole or in part, symptoms associated with a disorder or disease, or slowing or halting further progression or worsening of those symptoms, or, in another embodiment, an amount capable of preventing or providing prophylaxis for the disease or disorder in a subject at risk for developing the disease or disorder as disclosed herein, such as cancer. In one embodiment, an effective amount of a solid form of Compound 1 is an amount that inhibits a kinase in a cell, such as, for example, in vitro or in vivo. In one embodiment the kinase is mTOR, DNA-PK, PI3K or a combination thereof. In some embodiments, the effective amount of a solid form of Compound 1 inhibits the kinase in a cell by 10%, 20%, 30%, 40%, 50%, 60%, 70%, 80%, 90% or 99%, compared to the activity of the kinase in an untreated cell. The effective amount of a solid form of Compound 1, for example in a pharmaceutical composition, may be at a level that will exercise the desired effect; for example, about 0.005 mg/kg of a subject's body weight to about 100 mg/kg of a patient's body weight in unit dosage for both oral and parenteral administration. As will be apparent to those skilled in the art, it is to be expected that the effective amount of a solid form of Compound 1 disclosed herein may vary depending on the indication being treated, e.g., the effective amount of a solid form of Compound 1 would likely be different for treating patients suffering from, or at risk for, inflammatory conditions relative to the effective amount of a solid form of Compound 1 for treating patients suffering from, or at risk of, a different disorder, e.g., cancer or a metabolic disorder.

"Patient" or "subject" is defined herein to include animals, such as mammals, including, but not limited to, primates (e.g., humans), cows, sheep, goats, horses, dogs, cats, rabbits, rats, mice, monkeys, chickens, turkeys, quails, or guinea pigs and the like. In specific embodiments, the patient or subject is a human.

The term "cancer" refers to any of various malignant neoplasms characterized by the proliferation of cells that can invade surrounding tissue and metastasize to new body sites. Both benign and malignant tumors are classified according to the type of tissue in which they are found. For example, fibromas are neoplasms of fibrous connective tissue, and melanomas are abnormal growths of pigment (melanin) cells. Malignant tumors originating from epithelial tissue, e.g., in skin, bronchi, and stomach, are termed carcinomas. Malignancies of epithelial glandular tissue such as are found in the breast, prostate, and colon, are known as adenocarcinomas. Malignant growths of connective tissue, e.g., muscle, cartilage, lymph tissue, and bone, are called sarcomas. Lymphomas and leukemias are malignancies arising among white blood cells. Through the process of metastasis, tumor cell migration to other areas of the body establishes neoplasms in areas away from the site of initial appearance. Bone tissues are one of the most favored sites of metastases of malignant tumors, occurring in about 30% of all cancer cases. Among malignant tumors, cancers of the lung, breast, prostate or the like are particularly known to be likely to metastasize to bone.

In the context of neoplasm, cancer, tumor growth or tumor cell growth, inhibition may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention. In this context, the term "prevention" includes either preventing the onset of clinically evident neoplasia altogether or preventing the onset of a preclinically evident stage of neoplasia in individuals at risk. Also intended to be encompassed by this definition is the prevention of transformation into malignant cells or to arrest or reverse the progression of premalignant cells to malignant cells. This includes prophylactic treatment of those at risk of developing the neoplasia.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
| --- | --- | --- | --- | --- |
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | Infiltrate cleared on repeat biopsy; if indeterminate by morphology, immunohistochemistry should be negative |

-continued

| Response | Definition | Nodal Masses | Spleen, liver | Bone Marrow |
|---|---|---|---|---|
| PR | Regression of measurable disease and no new sites | ≥50% decrease in SPD of up to 6 largest dominant masses; no increase in size of other nodes<br>(a) FDG-avid or PET positive prior to therapy; one or more PET positive at previously involved site<br>(b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or PD | (a) FDG-avid or PET positive prior to therapy; PET positive at prior sites of disease and no new sites on CT or PET<br>(b) Variably FDG-avid or PET negative; no change in size of previous lesions on CT | | |
| PD or relapsed disease | Any new lesion or increase by ≥50% of previously involved sites from nadir | Appearance of a new lesion(s) ≥1.5 cm in any axis, ≥50% increase in SPD of more than one node, or ≥50% increase in longest diameter of a previously identifed node ≥1 cm in short axis Lesions PET positive if FDG-avid lymphoma or PET positive prior to therapy | ≥50% increase from nadir in the SPD of any previous lesions | New or recurrent involvement |

Abbreviations:
CR, complete remission;
FDG, [$^{18}$F]fluorodeoxyglucose;
PET, positron emission tomography;
CT, computed tomography;
PR, partial remission;
SPD, sum of the product of the diameters;
SD, stable disease;
PD, progressive disease.

| End point | Patients | Definition | Measured from |
|---|---|---|---|
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations:
CR: complete remission;
PR: partial remission.

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of lymphoma-related symptoms can also be used in this end point.

In certain embodiments, the treatment of CLL may be assessed by the International Workshop Guidelines for CLL (see Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood, 2008; (111) 12: 5446-5456) using the response and endpoint definitions shown therein and in particular:

| Parameter | CR | PR | PD |
|---|---|---|---|
| Group A | | | |
| Lymphadenopathy[†] | None >1.5 cm | Decrease ≥50% | Increase ≥50% |
| Hepatomegaly | None | Decrease ≥50% | Increase ≥50% |
| Splenomegaly | None | Decrease ≥50% | Increase ≥50% |
| Blood lymphocytes | <4000/μL | Decrease ≥50% from baseline | Increase ≥50% over baseline |
| Marrow[‡] | Normocellular, <30% lymphocytes, no B-lymphoid nodules. Hypocellular marrow defines CRi (5.1.6). | 50% reduction in marrow infiltrate, or B-lymphoid nodules | |
| Group B | | | |
| Platelet count | >100 000/μL | >100 000/μL or increase ≥50% over baseline | Decrease of ≥50% from baseline secondary to CLL |
| Hemoglobin | >11.0 g/dL | >11 g/dL or increase ≥50% over baseline | Decrease of >2 g/dL from baseline secondary to CLL |
| Neutrophils[†] | >1500/μL | >1500/μL or >50% improvement over baseline | |

Group A criteria define the tumor load; Group B criteria define the function of the hematopoietic system (or marrow). CR (complete remission): all of the criteria have to be met, and patients have to lack disease-related constitutional symptoms; PR (partial remission): at least two of the criteria of group A plus one of the criteria of group B have to be met; SD is absence of progressive disease (PD) and failure to achieve at least a PR; PD: at least one of the above criteria of group A or group B has to be met. Sum of the products of multiple lymph nodes (as evaluated by CT scans in clinical trials, or by physical examination in general practice). These parameters are irrelevant for some response categories.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7), using the response and endpoint definitions shown below:

| Response Subcategory | Response Criteria[a] |
|---|---|
| sCR | CR as defined below plus Normal FLC ratio and Absence of clonal cells in bone marrow[b] by immunohistochemistry or immunofluorescence[c] |
| CR | Negative immunofixation on the serum and urine and Disappearance of any soft tissue plasmacytomas and <5% plasma cells in bone marrow[b] |
| VGPR | Serum and urine M-protein detectable by immunofixation but not on electrophoresis or 90% or greater reduction in serum M-protein plus urine M-protein level <100 mg per 24 h |

-continued

| Response Subcategory | Response Criteria[a] |
|---|---|
| PR | ≥50% reduction of serum M-protein and reduction in 24-h urinary M-protein by≥90% or to <200 mg per 24 h<br>If the serum and urine M-protein are unmeasurable,[d] a ≥50% decrease in the difference between involved and uninvolved FLC levels is required in place of the M-protein criteria<br>If serum and urine M-protein are unmeasurable, and serum free light assay is also unmeasurable, ≥50% reduction in plasma cells is required in place of M-protein, provided baseline bone marrow plasma cell percentage was ≥30%<br>In addition to the above listed criteria, if present at baseline, a ≥50% reduction in the size of soft tissue plasmacytomas is also required |
| SD (not recommended for use as an indicator of response; stability of disease is best described by providing the time to progression estimates) | Not meeting criteria for CR, VGPR, PR or progressive disease |

Abbreviations:
CR, complete response;
FLC, free light chain;
PR, partial response;
SD, stable disease;
sCR, stringent complete response;
VGPR, very good partial response;
[a]All response categories require two consecutive assessments made at anytime before the institution of any new therapy; all categories also require no known evidence of progressive or new bone lesions if radiographic studies were performed. Radiographic studies are not required to satisfy these response requirements;
[b]Confirmation with repeat bone marrow biopsy not needed;
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

In certain embodiments, the treatment of a cancer may be assessed by Response Evaluation Criteria in Solid Tumors (RECIST 1.1) (see Thereasse P., et al. New Guidelines to Evaluate the Response to Treatment in Solid Tumors. J. of the National Cancer Institute; 2000; (92) 205-216 and Eisenhauer E. A., Therasse P., Bogaerts J., et al. New response evaluation criteria in solid tumours: Revised RECIST guideline (version 1.1). European J. Cancer; 2009; (45) 228-247). Overall responses for all possible combinations of tumor responses in target and non-target lesions with our without the appearance of new lesions are as follows:

| Target lesions | Non-target lesions | New lesions | Overall response |
|---|---|---|---|
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response;
PR = partial response;
SD = stable disease; and
PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions and stable disease (SD) is neither sufficient shrinkage to qualify for partial response nor sufficient increase to qualify for progressive disease, taking as reference the smallest sum longest diameter since the treatment started.

With respect to the evaluation of non-target lesions, complete response (CR) is the disappearance of all non-target lesions and normalization of tumor marker level; incomplete response/stable disease (SD) is the persistence of one or more non-target lesion(s) and/or the maintenance of tumor marker level above the normal limits, and progressive disease (PD) is the appearance of one or more new lesions and/or unequivocal progression of existing non-target lesions.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for highgrade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MRI scan is defined as the assessment performed at the end of the post-surgery rest period, prior to re-initiating compound treatment. The baseline MRI is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined MRI scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bidimensionally. A measurement is made of the maximal enhancing tumor diameter (also known as the longest diameter, LD). The greatest perpendicular diameter is measured on the same image. The cross hairs of bidimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bidimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all nonenhancing and other truly nonmeasurable lesions. Nonmeasurable lesions include foci of enhancement that are less than the specified smallest diameter (ie., less than 5 mm by 5 mm), nonenhancing lesions (eg., as seen on T1-weighted post-contrast, T2-weighted, or fluid-attenuated inversion recovery (FLAIR) images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (eg., recorded in the same order on source documents and eCRFs). All measurable and nonmeasurable lesions must be assessed using the same technique as at baseline (e.g., subjects should be imaged on the same MRI scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

In certain embodiments, treatment of a cancer may be assessed by the inhibition of phosphorylation of S6RP, 4E-BP1, AKT and/or DNA-PK in circulating blood and/or tumor cells, and/or skin biopsies or tumor biopsies/aspirates, before, during and/or after treatment with a TOR kinase inhibitor. For example, the inhibition of phosphorylation of S6RP, 4E-BP1, AKT and/or DNA-PK is assessed in B-cells, T-cells and/or monocytes. In other embodiments, treatment of a cancer may be assessed by the inhibition of DNA-dependent protein kinase (DNA-PK) activity in skin samples and/or tumor biopsies/aspirates, such as by assessment of the amount of pDNA-PK 52056 as a biomarker for DNA damage pathways, before, during, and/or after TOR kinase inhibitor treatment. In one embodiment, the skin sample is irradiated by UV light.

In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

Unless otherwise specified, to the extent that there is a discrepancy between a depicted chemical structure of a compound provided herein and a chemical name of a compound provided herein, the chemical structure shall control.

5.2 Compound 1

The solid forms, formulations and methods of use provided herein relate to solid forms (e.g., cocrystals) of Compound 1:

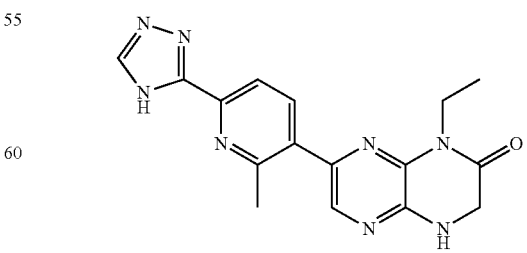

having the name 1-ethyl-7-(2-methyl-6-(1H-1,2,4-triazol-3-yl)pyridin-3-yl)-3,4-dihydropyrazino[2,3-b]pyrazin-2(1H)-one, including tautomers thereof.

Tautomers of Compound 1 include the following:

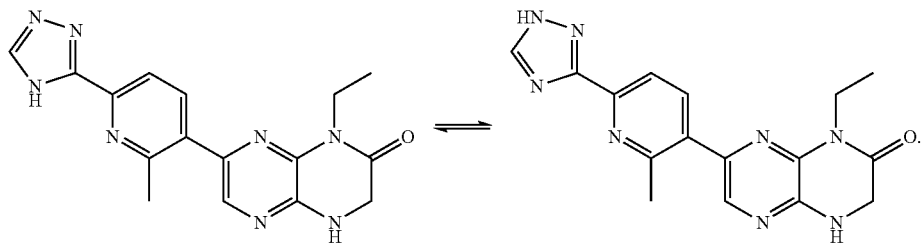 [SMILES: CCN1C(=O)CNc2ncc(-c3ccc(-c4nnc[nH]4)nc3C)nc21 ; CCN1C(=O)CNc2ncc(-c3ccc(-c4nc[nH]n4)nc3C)nc21]

Compound 1 can be prepared using reagents and methods known in the art, including the methods provided in U.S. Pat. No. 8,110,578, issued on Feb. 7, 2012; US Patent Publication Application No. 2011/0137028, published on Jun. 9, 2011; and U.S. Provisional Patent Application No. 61/813,064, filed on Apr. 17, 2013, the entire contents of each of which are incorporated herein by reference.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3 Solid Form Cocrystals of Compound 1

While not intending to be bound by any particular theory, certain solid form cocrystals are characterized by physical properties, e.g., stability, solubility and dissolution rate, appropriate for pharmaceutical and therapeutic dosage forms. Moreover, while not wishing to be bound by any particular theory, certain solid form cocrystals are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid form cocrystals suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

In one embodiment, provided herein are solid forms (e.g., crystal forms, amorphous forms, or mixtures thereof) comprising (a) Compound 1; and (b) a coformer. In one embodiment, provided herein are solid forms (e.g., crystal forms, amorphous forms, or mixtures thereof) comprising (a) a free base of Compound 1; and (b) a coformer. Compound 1 can be synthesized or obtained according to a method known in the literature or based upon the teachings herein, including the methods described in detail in the examples herein.

In certain embodiments, the coformer is benzoic acid, fumaric acid, gentisic acid, nicotinamide, succinic acid or maleic acid.

In one embodiment, solid forms provided herein may be a crystal form or an amorphous form or mixtures thereof (e.g., mixtures of crystal forms, or mixtures of crystal and amorphous forms), which comprises (a) Compound 1; and (b) a coformer. In one embodiment, provided herein is a crystal form comprising (a) Compound 1; and (b) a coformer. In one embodiment, provided herein is a cocrystal comprising (a) Compound 1; and (b) a coformer. In one embodiment, provided herein is an amorphous form comprising (a) Compound 1; and (b) a coformer. In one embodiment, provided herein is a mixture comprising (i) a cocrystal comprising (a) Compound 1; and (b) a coformer; and (ii) a crystal form of Compound 1. In one embodiment, provided herein is a mixture comprising (i) a cocrystal comprising (a) Compound 1; and (b) a coformer; and (ii) an amorphous form of Compound 1.

In one embodiment, provided herein is a solid form comprising (a) Compound 1 and (b) a coformer that is substantially crystalline. In one embodiment, provided herein is a solid form comprising a cocrystal comprising (a) Compound 1 and (b) a coformer. In one embodiment, provided herein is a solid form comprising (i) a cocrystal comprising (a) Compound 1 and (b) a coformer and (ii) an amorphous form of Compound 1. In one embodiment, provided herein is a solid form comprising (i) a cocrystal comprising (a) Compound 1 and (b) a coformer and (ii) one or more additional crystal forms of Compound 1.

In one embodiment, provided herein is an unsolvated solid form comprising (a) Compound 1 and (b) a coformer. In one embodiment, provided herein is an anhydrous solid form comprising (a) Compound 1 and (b) a coformer. In one embodiment, provided herein is an unsolvated crystal form comprising (a) Compound 1 and (b) a coformer. In one embodiment, provided herein is an anhydrous crystal form comprising (a) Compound 1 and (b) a coformer. In one embodiment, provided herein is an unsolvated amorphous form comprising (a) Compound 1 and (b) a coformer. In one embodiment, provided herein is an anhydrous amorphous form comprising (a) Compound 1 and (b) a coformer. In one embodiment, provided herein is a solvated solid form comprising (a) Compound 1 and (b) a coformer. In one embodiment, provided herein is a hydrated solid form comprising (a) Compound 1 and (b) a coformer (e.g., a hydrate having a stoichiometric or non-stoichiometric amount of water). In one embodiment, provided herein is a hydrated form of (a) Compound 1 and (b) a coformer, including, but not limited to, a hemihydrate, a monohydrate, a dihydrate, a trihydrate, and the like. In one embodiment, the hydrated form is substantially crystalline. In one embodiment, the hydrated form is substantially amorphous. In one embodiment, the anhydrous form is substantially crystalline. In one embodiment, the anhydrous form is substantially amorphous. In one embodiment, provided herein is an unsolvated cocrystal comprising (a) Compound 1 and (b) a coformer. In one embodiment, provided herein is an anhydrous cocrystal comprising (a) Compound 1 and (b) a coformer. In one embodiment, provided herein is a hydrated cocrystal comprising (a) Compound 1 and (b) a coformer. In one embodiment, provided herein is a solvated cocrystal comprising (a) Compound 1 and (b) a coformer.

Solid forms provided herein can be prepared by the methods described herein, or by techniques, including, but not limited to, heating, cooling, freeze drying, spray drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces, such as, e.g., in nanopores or capillaries, recrystallization on surfaces or templates, such as, e.g., on polymers, recrystallization in the presence of additives, such as, e.g., cocrystal counter-molecules, desolvation, dehydration, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation, and precipitation from a supercritical fluid. The particle size of the resulting solid forms, which can vary (e.g., from nanometer dimensions to millimeter dimensions), can be controlled, e.g., by varying crystallization conditions, such as, e.g., the rate of crystallization and/or the crystallization solvent system, or by particle-size reduction techniques, e.g., grinding, milling, micronizing, or sonication.

In some embodiments, the cocrystal comprising (a) Compound 1 and (b) a coformer can be obtained by crystallization from certain solvent systems, for example, solvent systems comprising one or more of the following solvents: tetrahydrofuran (THF), methanol and water, a mixture of THF and water, and a mixture of methanol and water. In certain embodiments, a solid form provided herein (e.g., a cocrystal comprising (a) Compound 1 and (b) a coformer) can be obtained by cooling evaporation crystallization, powder in saturated solutions crystallization, slurry crystallization, and grinding crystallization.

In certain embodiments, the non-covalent forces are one or more hydrogen bonds (H-bonds). The coformer may be H-bonded directly to Compound 1 or may be H-bonded to an additional molecule which is bound to Compound 1. The additional molecule may be H-bonded to Compound 1 or bound ionically or covalently to Compound 1. The additional molecule could also be a different active or inactive ingredient. In certain embodiments, the cocrystals may include one or more solvate molecules in the crystalline lattice, i.e., solvates of cocrystals, or a cocrystal further comprising a solvent or compound that is a liquid at room temperature. In certain embodiments, the cocrystals may be a cocrystal between a coformer and a salt of Compound 1. In certain embodiments, the non-covalent forces are pi-stacking, guest-host complexation and/or van der Waals interactions. Hydrogen bonding can result in several different intermolecular configurations. For example, hydrogen bonds can result in the formation of dimers, linear chains, or cyclic structures. These configurations can further include extended (two-dimensional) hydrogen bond networks and isolated triads.

In certain embodiments, the coformer is a solid under ambient temperature conditions when in its pure form.

In certain embodiments, cocrystals can be prepared using solid-state methods such as solid-state grinding and solvent-drop grinding. In certain embodiments, cocrystals can be prepared using high-throughput screening. In certain embodiments cocrystals can be prepared using solution-based crystallization.

In certain embodiments, cocrystals formation can lead to enhancement of physical properties of the resulting solid forms, such as solubility, dissolution rate, bioavailability, physical stability, chemical stability, flowability, fractability, or compressibility.

In certain embodiments, provided herein are cooling evaporative methods for making a solid form cocrystal of Compound 1, comprising 1) obtaining a close-to saturated solution of Compound 1 and conformers in a ratio (e.g., about 1:1.1 or about 1:1.4) in a solvent; 2) heating the solution to a first temperature (e.g., about 30° C. to about 50° C.); 3) cooling the solution to a second temperature (e.g., about −5° C. to about 15° C.); 4) keeping the solution at the second temperature for a period of time (e.g., 48 hours); 5) filtering the solution to yield a solid if there is precipitation; and 6) evaporating the solvent to collect a solid if there is no precipitation after step 4. In certain embodiments, provided herein are cooling evaporative methods for making a solid form cocrystal of Compound 1, comprising 1) obtaining a close-to saturated solution of Compound 1 and conformers in a solvent; 2) heating the solution to about 40° C.); 3) cooling the solution to about 2° C.); 4) keeping the solution at about 2° C. for about 48 hours; 5) filtering the solution to yield a solid if there is precipitation; and 6) evaporating the solvent to collect a solid if there is no precipitation after step 4. In certain embodiments, the solvent is methanol, THF, a mixture of methanol and water (50/50) or a mixture of THF and water (50/50). In one embodiment, the molar ratio of Compound 1 and the conformers in step 1 is about 1:1.1 or about 1:1.4.

In certain embodiments, provided herein are powder in saturated solutions methods for making a solid form cocrystal of Compound 1, comprising 1) obtaining a saturated solution of Compound 1 in a solvent; 2) adding conformers into the solution; 3) stirring the solution at ambient temperature for a period of time; 4) filtering the solution to yield a first solid and 5) evaporate the solvent to collect a second solid. In certain embodiments, the solvent is methanol, THF, a mixture of methanol and water (50/50) or a mixture of THF and water (50/50). In one embodiment, the molar ratio of Compound 1 and the conformers is about 1:5. In one embodiment, the period of time is about 4 hours.

In certain embodiments, provided herein are slurry methods for making a solid form cocrystal of Compound 1, comprising 1) obtaining a slurry of Compound 1 and conformers in a ratio in a solvent; 2) stirring the slurry for a period of time; 3) collecting a solid from the slurry by filtration (e.g., centrifuge filtration). In certain embodiments, the solvent is methanol, THF, a mixture of methanol and water (50/50) or a mixture of THF and water (50/50). In one embodiment, the molar ratio of Compound 1 and the conformers is about 1:1.1. In one embodiment, the period of time is about 3 days.

In certain embodiments, provided herein are grinding methods for making a solid form cocrystal of Compound 1, comprising 1) adding Compound 1, conformers and a solvent into a grinding machine; 2) shaking the container for a period of time at a particular frequency; 3) collecting the resulting solid by filtration (e.g., centrifuge filtration). In certain embodiments, the solvent is methanol, THF, a mixture of methanol and water (50/50) or a mixture of THF and water (50/50). In one embodiment, the molar ratio of Compound 1 and the conformers is about 1:1.1. In one embodiment, the period of time is about 1 hour. In one embodiment, the frequency is about 30 Hz.

The solid form cocrystals provided herein (e.g., Form 1, Form 2, Form 3, Form 4, Form 5, Form 6, Form 7 and Form 8) may be characterized using a number of methods known to a person having ordinary skill in the art, including, but not limited to, single crystal X-ray diffraction, X-ray powder diffraction (XRPD), microscopy (e.g., scanning electron microscopy (SEM)), thermal analysis (e.g., differential scanning calorimetry (DSC), thermal gravimetric analysis (TGA), and hot-stage microscopy), spectroscopy (e.g., infrared, Raman, and solid-state nuclear magnetic resonance), single differential thermal analysis (SDTA), high performance liquid chromatography coupled with mass spectroscopy (HPLC-MS), thermogravimetrical analysis coupled with single differential thermal analysis (TGA-SDTA), and thermogravimetric analysis coupled with mass spectroscopy (TGA-MS). The particle size and size distribution of the solid form provided herein may be determined by conventional methods, such as laser light scattering technique.

The purity of the solid form cocrystals provided herein may be determined by standard analytical methods, such as thin layer chromatography (TLC), gel electrophoresis, gas chromatography, high performance liquid chromatography (HPLC), and mass spectrometry (MS).

It should be understood that the numerical values of the peaks of an X-ray powder diffraction pattern may vary slightly from one machine to another or from one sample to another, and so the values quoted are not to be construed as absolute, but with an allowable variability, such as ±0.2 degrees two theta (° 2θ) (see United State Pharmacopoeia, page 2228 (2003)).

5.3.1 Cocrystal Form 1 Comprising Compound 1 and Benzoic Acid

Provided herein is cocrystal Form 1, comprising Compound 1 and benzoic acid. In one embodiment, provided herein is a cocrystal comprising Compound 1 and benzoic acid that is substantially crystalline. In one embodiment, provided herein is a solid form comprising (i) a cocrystal comprising Compound 1 and benzoic acid and (ii) an amorphous form of Compound 1. In one embodiment, provided herein is a solid form comprising (i) a cocrystal comprising Compound 1 and benzoic acid and (ii) one or more additional crystal forms of Compound 1. Provided herein are various embodiments, preparations, or modifications of a cocrystal comprising Compound 1 and benzoic acid.

In one embodiment, Form 1 is a methanol solvated form comprising Compound 1 and benzoic acid. In another embodiment, Form 1 is crystalline.

In certain embodiments, Form 1 is obtained by grinding experiments comprising 1) adding Compound 1, benzoic acid and a solvent into a grinding container containing grinding balls; 2) shaking the container for a period of time at a particular frequency; 3) collecting the resulting solid by filtration (e.g., centrifuge filtration). In certain embodiments, the solvent is a mixture of methanol and water (50/50). In one embodiment, the molar ratio of Compound 1 and benzoic acid is about 1:1.1. In one embodiment, the period of time is about 1 hour. In one embodiment, the frequency is about 30 Hz.

In certain embodiments, a solid form provided herein, e.g., Form 1, is substantially crystalline, as indicated by, e.g., X-ray powder diffraction measurements. In one embodiment, Form 1 of Compound 1 has an X-ray powder diffraction pattern substantially as shown in FIG. 1 (middle pattern). In one embodiment, Form 1 of Compound 1 has one or more characteristic X-ray powder diffraction peaks at a two-theta angle of approximately 7.78, 13.02, 13.54, 20.62, 24.26, 25.02 or 26.1 degrees as depicted in FIG. 1. In another embodiment, Form 1 of Compound 1 has one, two, three or four characteristic X-ray powder diffraction peaks at a two-theta angle of approximately 7.78, 13.02, 25.02 or 26.1 degrees. In another embodiment, Form 1 of Compound 1 has one, two, three, four, five, six, or seven characteristic X-ray powder diffraction peaks as set forth in Table 12.

Figure 2:
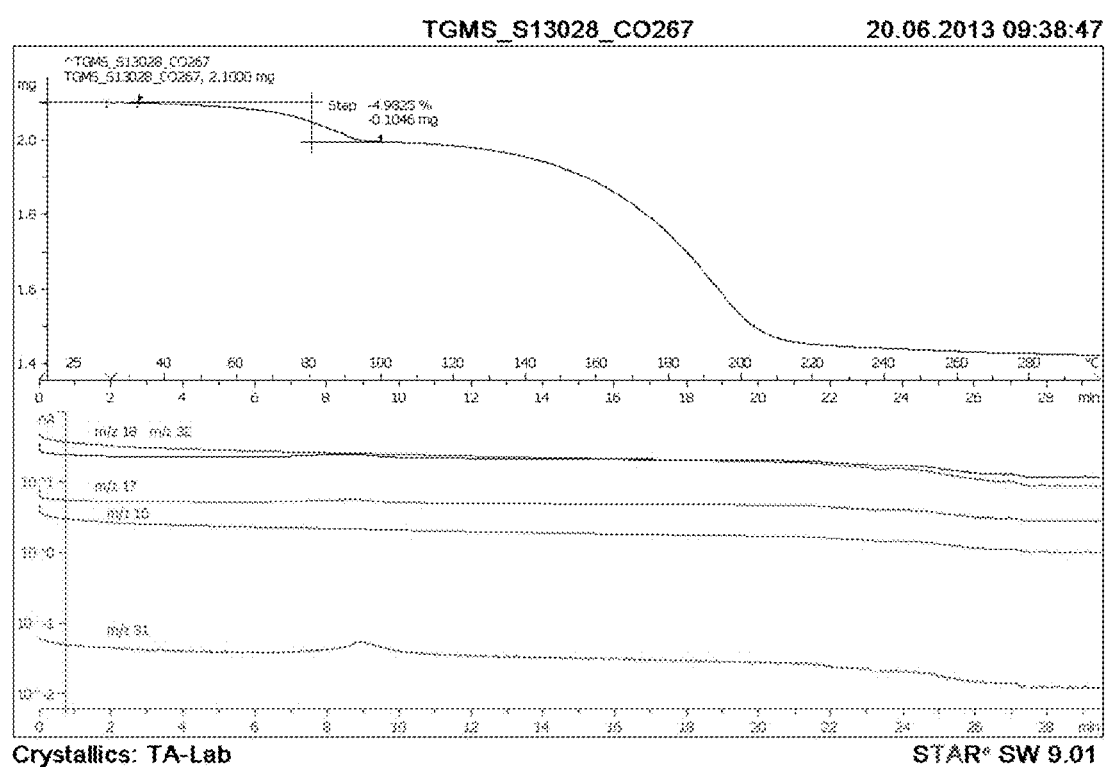
FIG. 2 depicts a thermogravimetric analysis coupled with mass spectroscopy of Form 1.

In one embodiment, provided herein is Form 1 having a thermogravimetric (TGA) thermograph corresponding substantially to the representative TGA thermogram as depicted in FIG. 2. In certain embodiments, the crystalline form exhibits a TGA thermogram comprising a total mass loss of approximately 5.0% of the total mass of the sample between approximately 35° C. and approximately 105° C. when heated from approximately 25° C. to approximately 300° C. Thus, in certain embodiments, the crystalline form loses about 5.0% of its total mass when heated from about ambient temperature to about 300° C.

Figure 3:
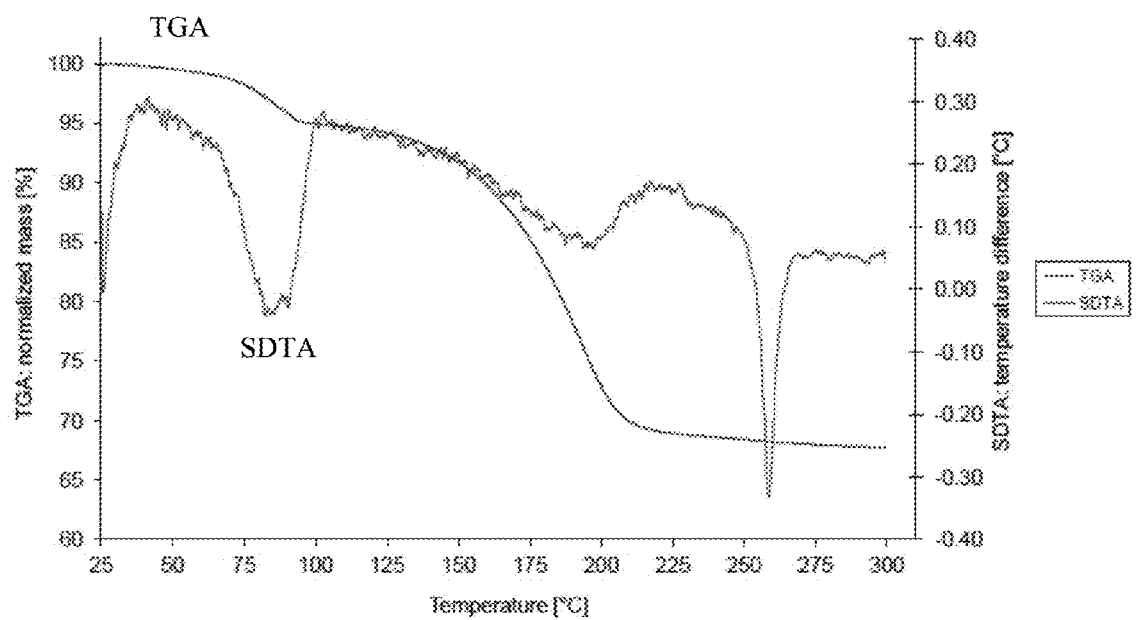
FIG. 3 depicts a thermogravimetrical analysis and single differential thermal analysis of Form 1.

In one embodiment, provided herein is Form 1 having a single differential thermal analysis (SDTA) thermogram as depicted in FIG. 3 comprising an endothermic event with a maximum at about 89° C., followed by decomposition starting at about 200° C., when heated from approximately 25° C. to approximately 300° C.

In still another embodiment, Form 1 of Compound 1 is substantially pure. In certain embodiments, the substantially pure Form 1 of Compound 1 is substantially free of other solid forms, e.g., amorphous form. In certain embodiments, the purity of the substantially pure Form 1 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.2 Cocrystal Form 2 Comprising Compound 1 and Fumaric Acid

Provided herein is cocrystal Form 2, comprising Compound 1 and fumaric acid. In one embodiment, provided herein is a cocrystal comprising Compound 1 and fumaric acid that is substantially crystalline. In one embodiment, provided herein is a solid form comprising (i) a cocrystal comprising Compound 1 and fumaric acid and (ii) an amorphous form of Compound 1. In one embodiment, provided herein is a solid form comprising (i) a cocrystal comprising Compound 1 and fumaric acid and (ii) one or more additional crystal forms of Compound 1. Provided herein are various embodiments, preparations, or modifications of a cocrystal comprising Compound 1 and fumaric acid.

In one embodiment, Form 2 is a hydrated form comprising Compound 1 and fumaric acid. In another embodiment, Form 2 is crystalline.

In certain embodiments, Form 2 is obtained by grinding experiments comprising 1) adding Compound 1, fumaric acid and a solvent into a grinding container containing grinding balls; 2) shaking the container for a period of time at a particular frequency; 3) collecting the resulting solid by filtration (e.g., centrifuge filtration). In certain embodiments, the solvent is a mixture of methanol and water (50/50). In one embodiment, the molar ratio of Compound 1 and benzoic acid is about 1:1.1. In one embodiment, the period of time is about 1 hour. In one embodiment, the frequency is about 30 Hz.

Figure 7:
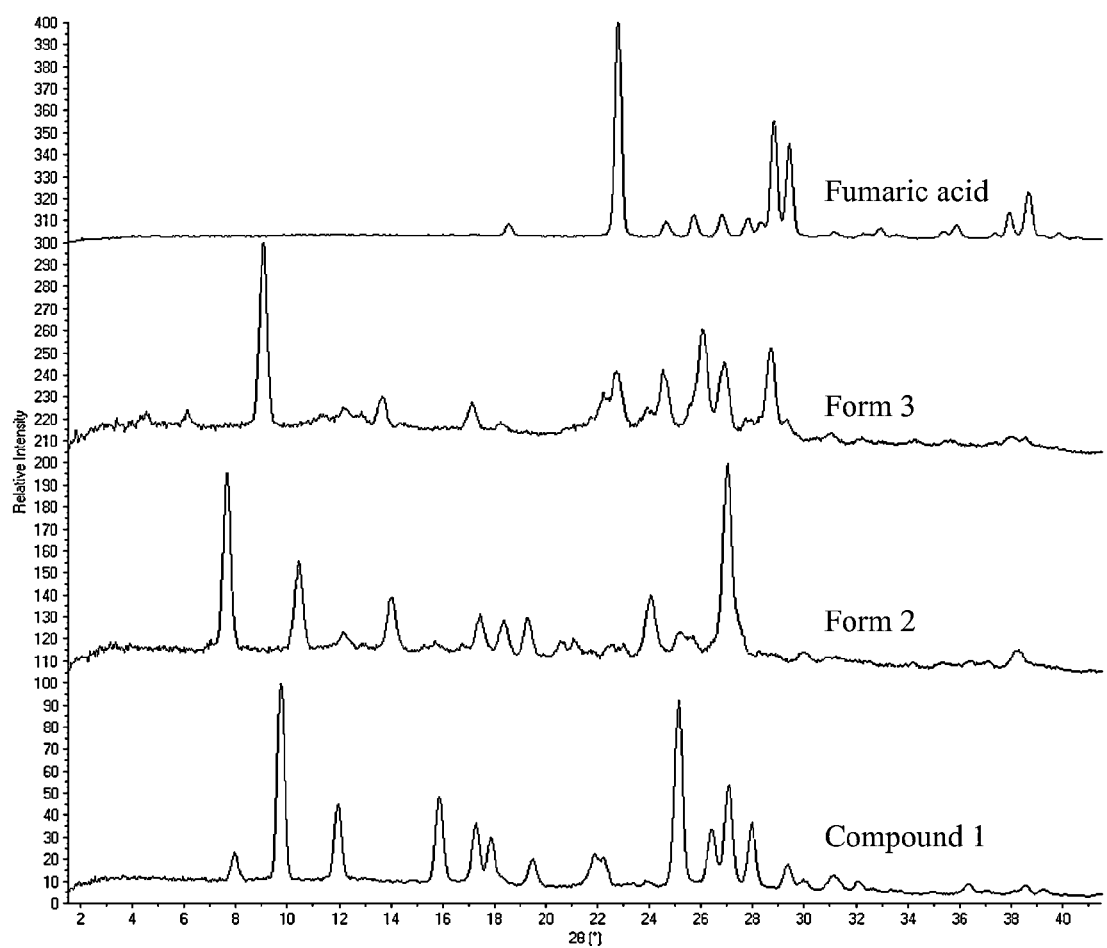
FIG. 7 depicts an X-ray powder diffractogram stack plot of Compound 1, Form 2, Form 3 and fumaric acid.

In certain embodiments, a solid form provided herein, e.g., Form 2, is substantially crystalline, as indicated by, e.g., X-ray powder diffraction measurements. In one embodiment, Form 2 of Compound 1 has an X-ray powder diffraction pattern substantially as shown in FIG. 7 (second pattern from bottom). In one embodiment, Form 2 of Compound 1 has one or more characteristic X-ray powder diffraction peaks at a two-theta angle of approximately 7.66, 10.42, 14.02, 17.46, 18.38, 19.3, 24.06 or 27.02 degrees as depicted in FIG. 7 (second pattern from bottom). In another embodiment, Form 2 of Compound 1 has one, two, three or four characteristic X-ray powder diffraction peaks at a two-theta angle of approximately 7.66, 10.42, 24.06 or 27.02 degrees. In another embodiment, Form 2 of Compound 1 has one, two, three, four, five, six, seven or eight characteristic X-ray powder diffraction peaks as set forth in Table 13.

Figure 8:
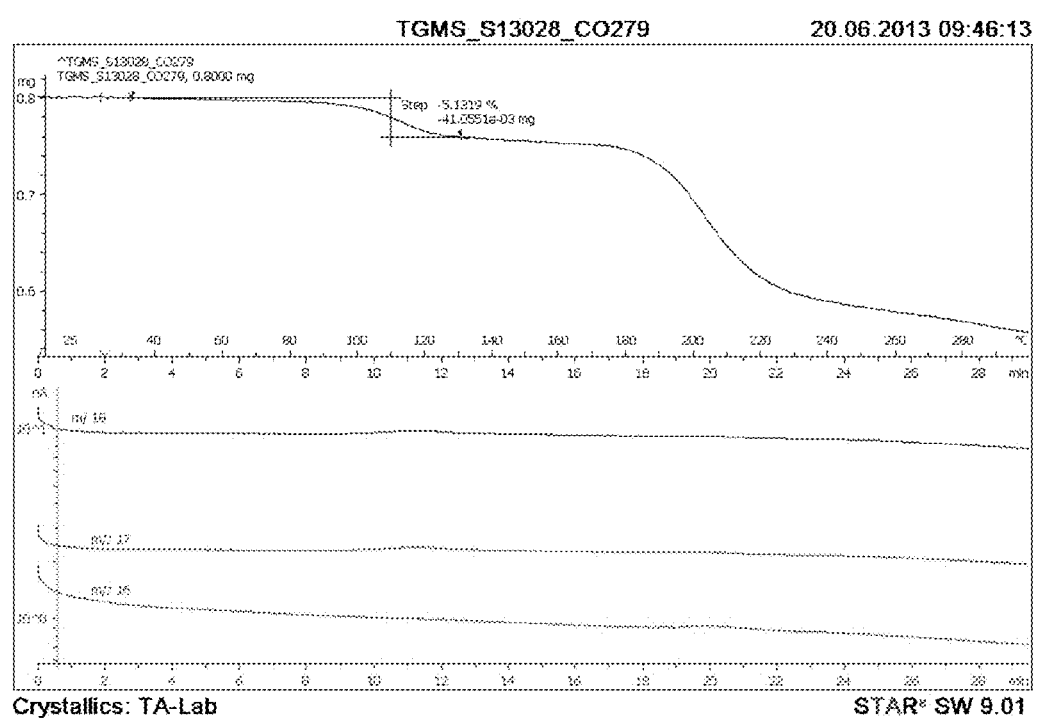
FIG. 8 depicts a thermogravimetric analysis coupled with mass spectroscopy of Form 2.

In one embodiment, provided herein is Form 2 having a thermogravimetric (TGA) thermograph corresponding substantially to the representative TGA thermogram as depicted in FIG. 8. In certain embodiments, the crystalline form exhibits a TGA thermogram comprising a total mass loss of approximately 5.1% of the total mass of the sample between approximately 35° C. and approximately 135° C. when heated from approximately 25° C. to approximately 300° C. Thus, in certain embodiments, the crystalline form loses about 5.1% of its total mass when heated from about ambient temperature to about 300° C.

Figure 9:
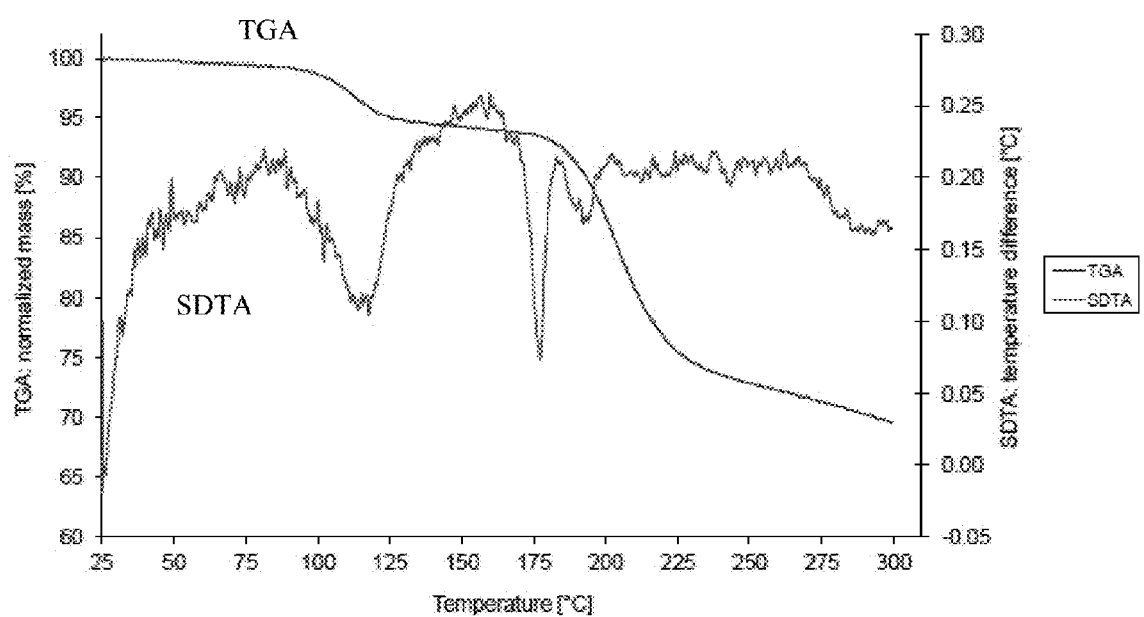
FIG. 9 depicts a thermogravimetrical analysis and single differential thermal analysis of Form 2.

In one embodiment, provided herein is Form 2 having a single differential thermal analysis (SDTA) thermogram as depicted in FIG. 9 comprising an endothermic event with a maximum at about 115° C., followed by an endothermic melt event at about 177° C. and then immediate decomposition, when heated from approximately 25° C. to approximately 300° C.

In still another embodiment, Form 2 of Compound 1 is substantially pure. In certain embodiments, the substantially pure Form 2 of Compound 1 is substantially free of other solid forms, e.g., amorphous form. In certain embodiments, the purity of the substantially pure Form 2 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.3 Cocrystal Form 3 Comprising Compound 1 and Fumaric Acid

Provided herein is cocrystal Form 3, comprising Compound 1 and fumaric acid. In one embodiment, provided herein is a solid form comprising Compound 1 and fumaric acid that is substantially crystalline. In one embodiment, provided herein is a solid form comprising (i) a cocrystal comprising Compound 1 and fumaric acid and (ii) an amorphous form of Compound 1. In one embodiment, provided herein is a solid form comprising (i) a cocrystal comprising Compound 1 and fumaric acid and (ii) one or more additional crystal forms of Compound 1. Provided herein are various embodiments, preparations, or modifications of a cocrystal comprising Compound 1 and fumaric acid.

In certain embodiments, Form 3 is obtained by cooling evaporative experiments comprising 1) obtaining a close-to saturated solution of Compound 1 and fumaric acid in a ratio (e.g., about 1:1.4) in a solvent; 2) heating the solution to a first temperature (e.g., about 30° C. to about 50° C.); 3) cooling the solution to a second temperature (e.g., about −5° C. to about 15° C.); 4) keeping the solution at the second temperature for a period of time (e.g., 48 hours); 5) filtering the solution to yield a solid if there is precipitation; and 6) evaporating the solvent to collect a solid if there is no precipitation after step 4. In certain embodiments, Form 3 is obtained by cooling evaporative experiments, comprising 1) obtaining a close-to saturated solution of Compound 1 and fumaric acid in a solvent; 2) heating the solution to about 40° C.); 3) cooling the solution to about 2° C.); 4) keeping the solution at about 2° C. for about 48 hours; 5) filtering the solution to yield a solid if there is precipitation; and 6) evaporating the solvent to collect a solid if there is no precipitation after step 4. In certain embodiments, the solvent is methanol. In one embodiment, the molar ratio of Compound 1 and fumaric acid in step 1 is about 1:1.4.

In certain embodiments, a solid form provided herein, e.g., Form 3, is substantially crystalline, as indicated by, e.g., X-ray powder diffraction measurements. In one embodiment, Form 3 of Compound 1 has an X-ray powder diffraction pattern substantially as shown in FIG. 7 (third pattern from bottom). In one embodiment, Form 3 of Compound 1 has one or more characteristic X-ray powder diffraction peaks at a two-theta angle of approximately 9.06, 13.66, 17.14, 22.74, 24.58, 26.06, 26.9 or 28.7 degrees as depicted in FIG. 7 (third pattern from bottom). In another embodiment, Form 3 of Compound 1 has one, two, three or four characteristic X-ray powder diffraction peaks at a two-theta angle of approximately 9.06, 26.06, 26.9 or 28.7 degrees. In another embodiment, Form 3 of Compound 1 has one, two, three, four, five, six, seven or eight characteristic X-ray powder diffraction peaks as set forth in Table 14.

Figure 13:
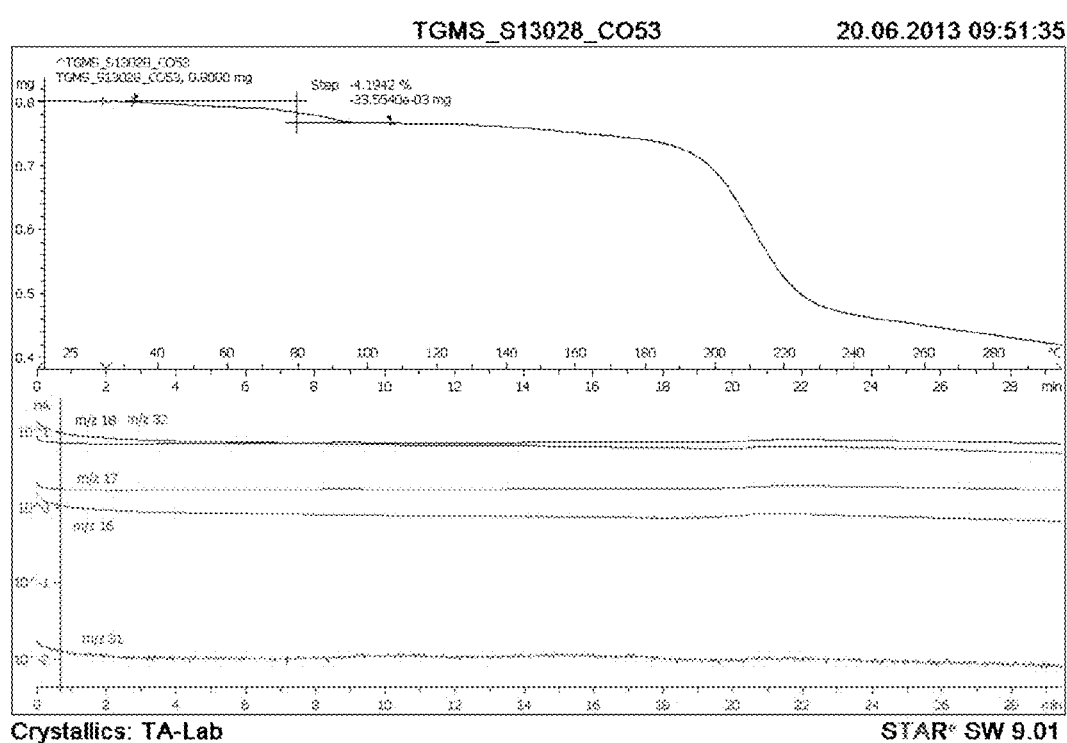
FIG. 13 depicts a thermogravimetric analysis coupled with mass spectroscopy of Form 3.

In one embodiment, provided herein is Form 3 having a thermogravimetric (TGA) thermograph corresponding substantially to the representative TGA thermogram as depicted in FIG. 13. In certain embodiments, the crystalline form exhibits a TGA thermogram comprising a total mass loss of approximately 4.2% of the total mass of the sample between approximately 35° C. and approximately 105° C. when heated from approximately 25° C. to approximately 300° C. Thus, in certain embodiments, the crystalline form loses about 4.2% of its total mass when heated from about ambient temperature to about 300° C.

Figure 14:
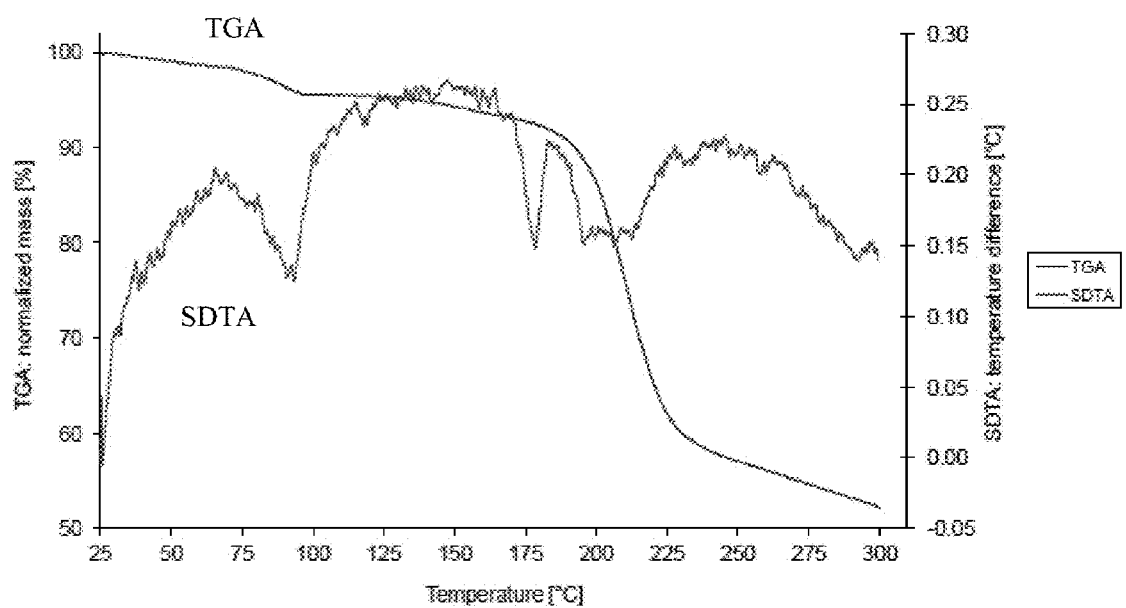
FIG. 14 depicts a thermogravimetrical analysis and single differential thermal analysis of Form 3.

In one embodiment, provided herein is Form 3 having a single differential thermal analysis (SDTA) thermogram as depicted in FIG. 14 comprising an endothermic event with a maximum at about 93° C., followed by an endothermic melt event at about 178.1° C. and then immediate decomposition, when heated from approximately 25° C. to approximately 300° C.

In still another embodiment, Form 3 of Compound 1 is substantially pure. In certain embodiments, the substantially pure Form 3 of Compound 1 is substantially free of other solid forms, e.g., amorphous form. In certain embodiments, the purity of the substantially pure Form 3 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.4 Cocrystal Form 4 Comprising Compound 1 and Gentisic Acid

Provided herein is cocrystal Form 4, comprising Compound 1 and gentisic acid. In one embodiment, provided herein is a solid form comprising Compound 1 and gentisic acid that is substantially crystalline. In one embodiment, provided herein is a solid form comprising (i) a cocrystal comprising Compound 1 and gentisic acid and (ii) an amorphous form of Compound 1. In one embodiment, provided herein is a solid form comprising (i) a cocrystal comprising Compound 1 and gentisic acid and (ii) one or more additional crystal forms of Compound 1. Provided herein are various embodiments, preparations, or modifications of a cocrystal comprising Compound 1 and gentisic acid.

In one embodiment, Form 4 is a hydrate comprising Compound 1 and gentisic acid. In another embodiment, Form 4 is crystalline.

In certain embodiments, Form 4 is obtained by cooling evaporative experiments comprising 1) obtaining a close-to saturated solution of Compound 1 and gentisic acid in a ratio (e.g., about 1:1.1) in a solvent; 2) heating the solution to a first temperature (e.g., about 30° C. to about 50° C.); 3) cooling the solution to a second temperature (e.g., about −5° C. to about 15° C.); 4) keeping the solution at the second temperature for a period of time (e.g., 48 hours); 5) filtering the solution to yield a solid if there is precipitation; and 6) evaporating the solvent to collect a solid if there is no precipitation after step 4. In certain embodiments, Form 4 is obtained by cooling evaporative experiments, comprising 1) obtaining a close-to saturated solution of Compound 1 and gentisic acid in a solvent; 2) heating the solution to about 40° C.); 3) cooling the solution to about 2° C.); 4) keeping the solution at about 2° C. for about 48 hours; 5) filtering the solution to yield a solid if there is precipitation; and 6) evaporating the solvent to collect a solid if there is no precipitation after step 4. In certain embodiments, the solvent is a mixture of methanol and water (50/50). In one embodiment, the molar ratio of Compound 1 and gentisic acid is about 1:1.1.

Figure 18:
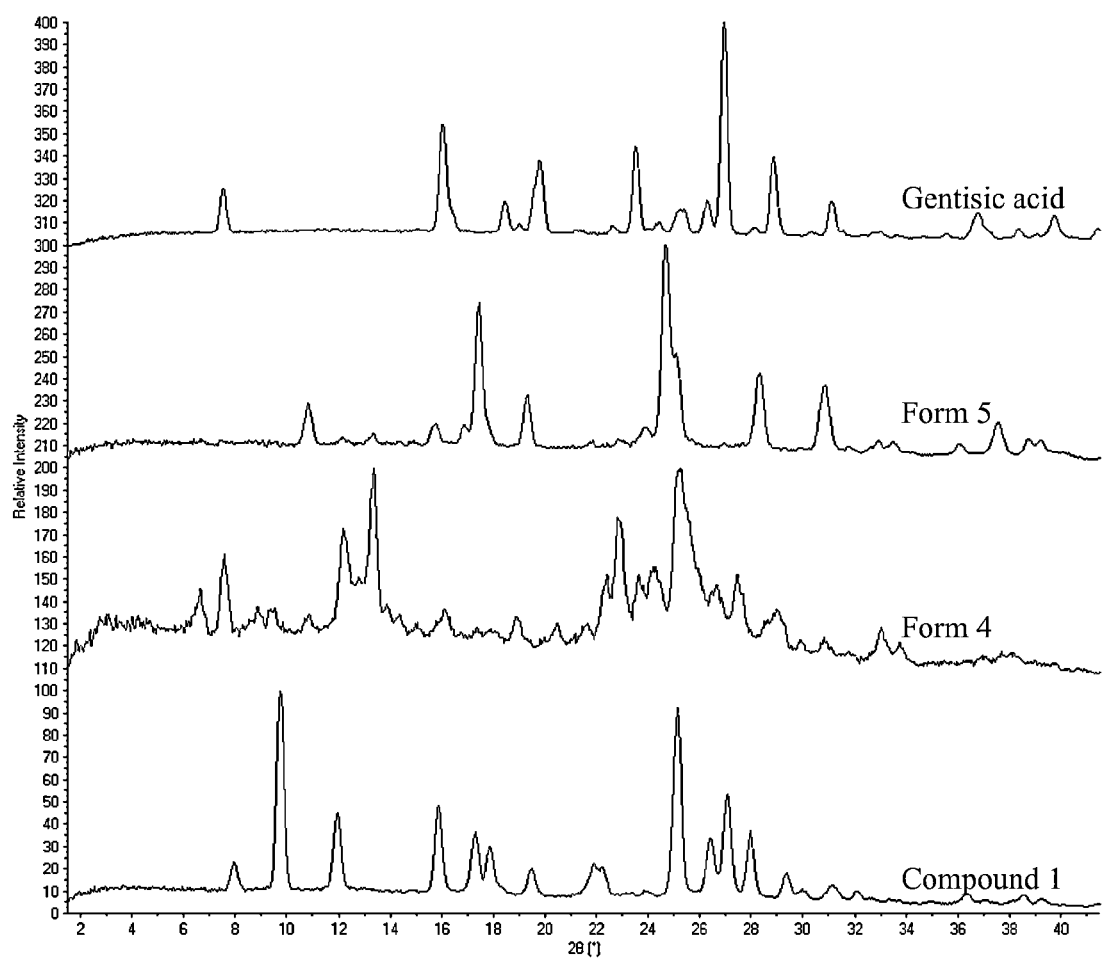
FIG. 18 depicts an X-ray powder diffractogram stack plot of Compound 1, Form 4, Form 5 and gentisic acid.

In certain embodiments, a solid form provided herein, e.g., Form 4, is substantially crystalline, as indicated by, e.g., X-ray powder diffraction measurements. In one embodiment, Form 4 of Compound 1 has an X-ray powder diffraction pattern substantially as shown in FIG. 18 (second pattern from bottom). In one embodiment, Form 4 of Compound 1 has one or more characteristic X-ray powder diffraction peaks at a two-theta angle of approximately 6.62, 7.58, 8.9, 9.42, 12.22, 12.82, 13.34, 13.9, 14.34, 16.14, 18.94, 20.46, 22.34, 22.9, 23.66, 24.22, 25.18, 26.62, 27.46 or 33.02 degrees as depicted in FIG. 18 (second pattern from bottom). In a specific embodiment, Form 4 of Compound 1 has one, two, three, four, five, six, seven or eight characteristic X-ray powder diffraction peaks at a two-theta angle of approximately 7.58, 12.22, 13.34, 22.34, 22.9, 23.66, 24.22 or 25.18 degrees. In another embodiment, Form 4 of Compound 1 has one, two, three or four characteristic X-ray powder diffraction peaks at a two-theta angle of approximately 12.22, 13.34, 22.9 or 25.18 degrees. In another embodiment, Form 4 of Compound 1 has one, two, three, four, five, six, seven, eight, nine, ten, eleven, twelve, thirteen, fourteen, fifteen, sixteen, seventeen, eighteen, nineteen or twenty characteristic X-ray powder diffraction peaks as set forth in Table 15.

Figure 19:
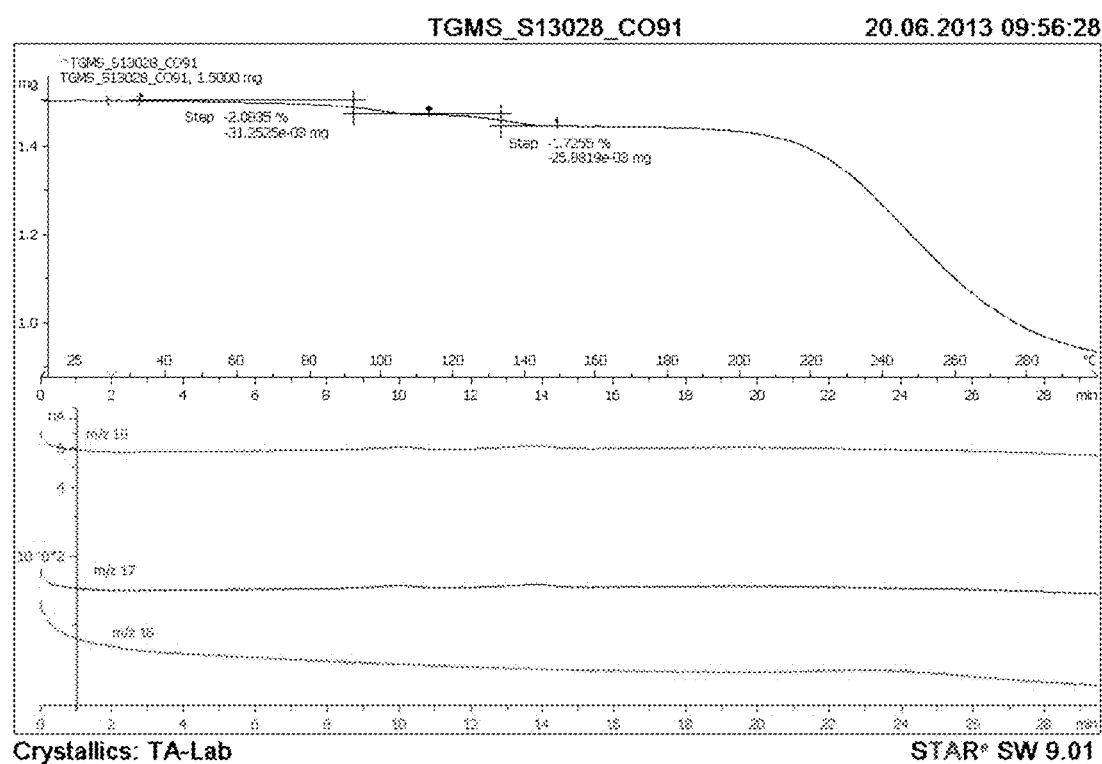
FIG. 19 depicts a thermogravimetric analysis coupled with mass spectroscopy of Form 4.

In one embodiment, provided herein is Form 4 having a thermogravimetric (TGA) thermograph corresponding substantially to the representative TGA thermogram as depicted in FIG. 19. In certain embodiments, the crystalline form exhibits a TGA thermogram comprising a total mass loss of approximately 1.7% of the total mass of the sample between approximately 110° C. and approximately 150° C. when heated from approximately 25° C. to approximately 300° C. Thus, in certain embodiments, the crystalline form loses about 1.7% of its total mass when heated from about ambient temperature to about 300° C.

Figure 20:
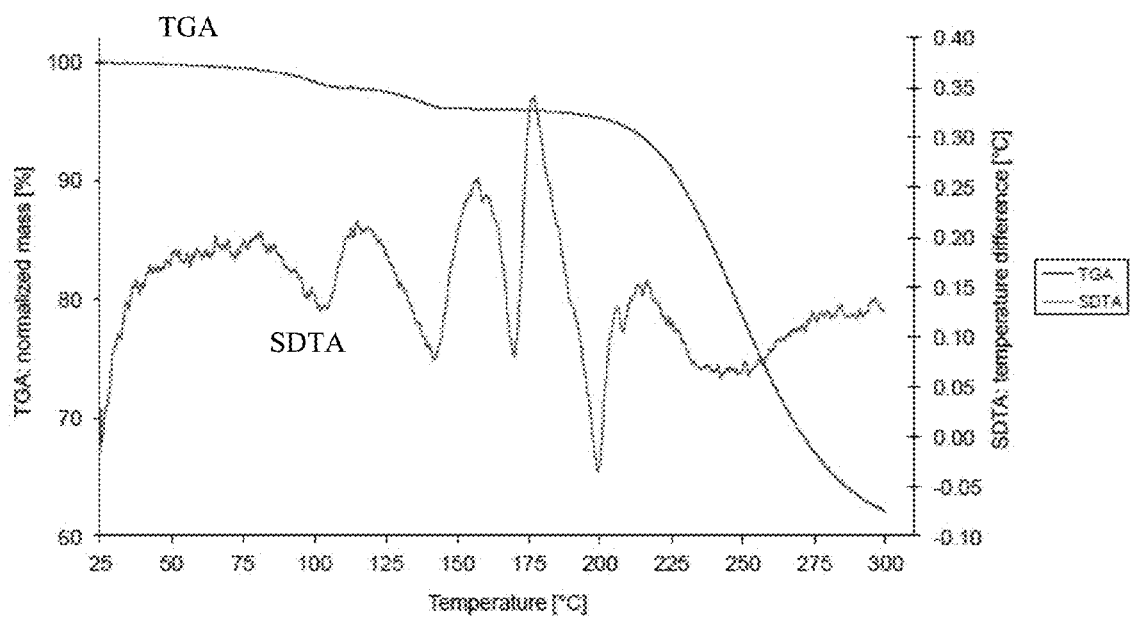
FIG. 20 depicts a thermogravimetrical analysis and single differential thermal analysis of Form 4.

In one embodiment, provided herein is Form 4 having a single differential thermal analysis (SDTA) thermogram as depicted in FIG. 20 comprising an endothermic event with two maximums at about 101.3 and 141.6° C., followed by an endothermic melt event at about 199° C. and then immediate decomposition, when heated from approximately 25° C. to approximately 300° C.

In still another embodiment, Form 4 of Compound 1 is substantially pure. In certain embodiments, the substantially pure Form 4 of Compound 1 is substantially free of other solid forms, e.g., amorphous form. In certain embodiments, the purity of the substantially pure Form 4 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.5 Cocrystal Form 5 Comprising Compound 1 and Gentisic Acid

Provided herein is cocrystal Form 5, comprising Compound 1 and gentisic acid. In one embodiment, provided herein is a solid form comprising Compound 1 and gentisic acid that is substantially crystalline. In one embodiment, provided herein is a solid form comprising (i) a cocrystal comprising Compound 1 and gentisic acid and (ii) an amorphous form of Compound 1. In one embodiment, provided herein is a solid form comprising (i) a cocrystal comprising Compound 1 and gentisic acid and (ii) one or more additional crystal forms of Compound 1. Provided herein are various embodiments, preparations, or modifications of a cocrystal comprising Compound 1 and gentisic acid.

In one embodiment, Form 5 is a hydrate comprising Compound 1 and gentisic acid. In another embodiment, Form 5 are crystalline.

In certain embodiments, Form 5 is obtained by cooling evaporative experiments comprising 1) obtaining a close-to saturated solution of Compound 1 and gentisic acid in a ratio (e.g., about 1:1.1) in a solvent; 2) heating the solution to a first temperature (e.g., about 30° C. to about 50° C.); 3) cooling the solution to a second temperature (e.g., about −5° C. to about 15° C.); 4) keeping the solution at the second temperature for a period of time (e.g., 48 hours); 5) filtering the solution to yield a solid if there is precipitation; and 6) evaporating the solvent to collect a solid if there is no precipitation after step 4. In certain embodiments, Form 5 is obtained by cooling evaporative experiments, comprising 1) obtaining a close-to saturated solution of Compound 1 and gentisic acid in a solvent; 2) heating the solution to about 40° C.); 3) cooling the solution to about 2° C.); 4) keeping the solution at about 2° C. for about 48 hours; 5) filtering the solution to yield a solid if there is precipitation; and 6) evaporating the solvent to collect a solid if there is no precipitation after step 4. In certain embodiments, the solvent is methanol. In one embodiment, the molar ratio of Compound 1 and gentisic acid in step 1 is about 1:1.1.

In certain embodiments, a solid form provided herein, e.g., Form 5, is substantially crystalline, as indicated by, e.g., X-ray powder diffraction measurements. In one embodiment, Form 5 of Compound 1 has an X-ray powder diffraction pattern substantially as shown in FIG. 18 (third pattern from bottom). In one embodiment, Form 5 of Compound 1 has one or more characteristic X-ray powder diffraction peaks at a two-theta angle of approximately 10.82, 16.9, 17.42, 19.3, 24.7, 28.34, 30.86 or 37.58 degrees as depicted in FIG. 18 (third pattern from bottom). In another embodiment, Form 5 of Compound 1 has one, two, three or four characteristic X-ray powder diffraction peaks at a two-theta angle of approximately 17.42, 24.7, 28.34 or 30.86 degrees. In another embodiment, Form 5 of Compound 1 has one, two, three, four, five, six, seven or eight characteristic X-ray powder diffraction peaks as set forth in Table 16.

Figure 24:
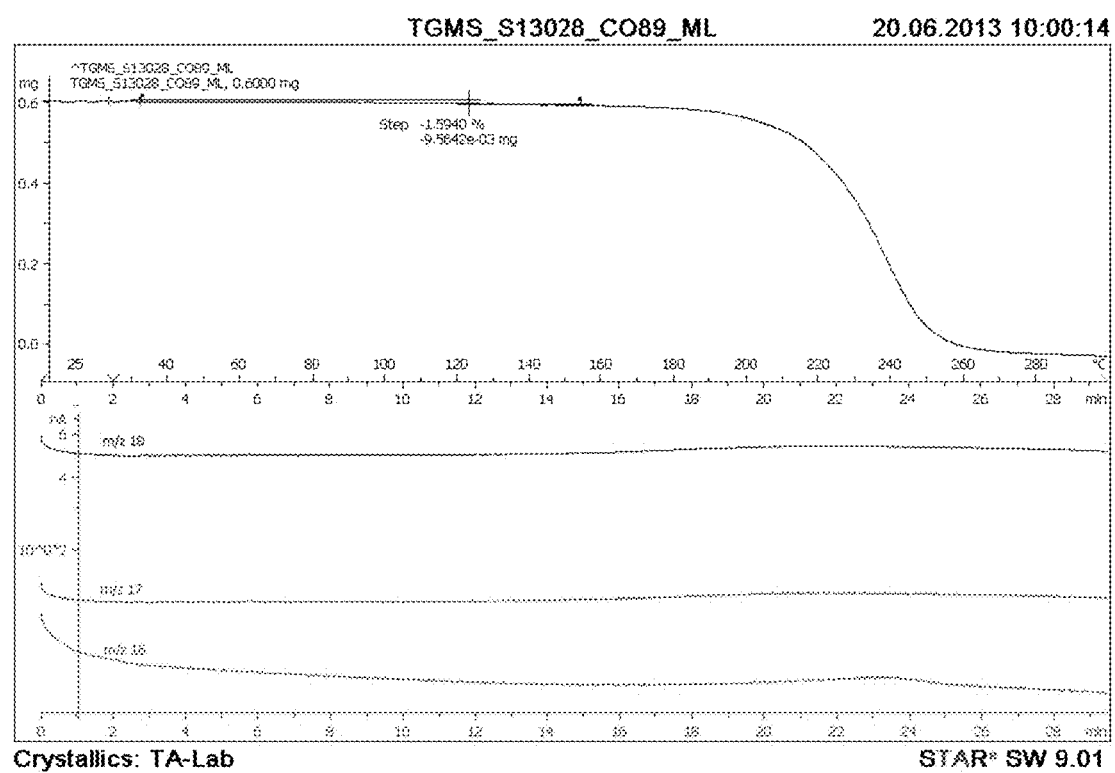
FIG. 24 depicts a thermogravimetric analysis coupled with mass spectroscopy of Form 5.

In one embodiment, provided herein is Form 5 having a thermogravimetric (TGA) thermograph corresponding substantially to the representative TGA thermogram as depicted in FIG. 24. In certain embodiments, the crystalline form exhibits a TGA thermogram comprising a total mass loss of approximately 1.6% of the total mass of the sample between approximately 35° C. and approximately 155° C. when heated from approximately 25° C. to approximately 300° C. Thus, in certain embodiments, the crystalline form loses about 1.6% of its total mass when heated from about ambient temperature to about 300° C.

Figure 25:
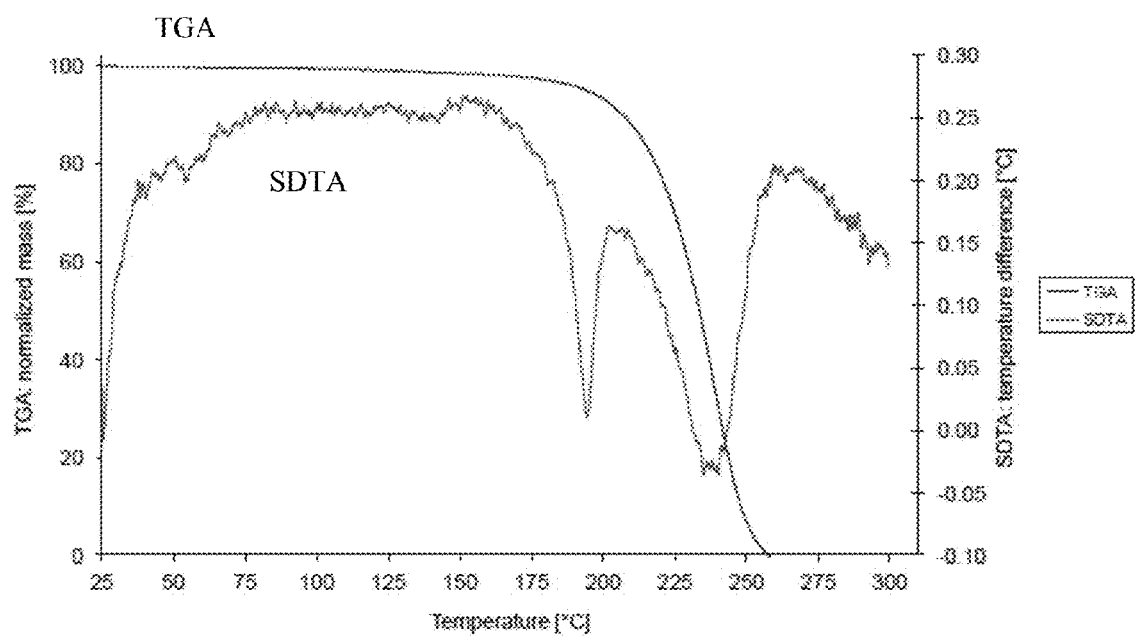
FIG. 25 depicts a thermogravimetrical analysis and single differential thermal analysis of Form 5.

In one embodiment, provided herein is Form 5 having a single differential thermal analysis (SDTA) thermogram as depicted in FIG. 25 comprising an endothermic event with a maximum at about 180° C., followed by immediate decomposition at about 236° C., when heated from approximately 25° C. to approximately 300° C.

In still another embodiment, Form 5 of Compound 1 is substantially pure. In certain embodiments, the substantially pure Form 5 of Compound 1 is substantially free of other solid forms, e.g., amorphous form. In certain embodiments, the purity of the substantially pure Form 5 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.6 Cocrystal Form 6 Comprising Compound 1 and Nicotinamide

Provide herein is cocrystal Form 6, comprising Compound 1 and nicotinamide. In one embodiment, provided herein is a solid form comprising Compound 1 and nicotinamide that is substantially crystalline. In one embodiment, provided herein is a solid form comprising (i) a cocrystal comprising Compound 1 and nicotinamide and (ii) an amorphous form of Compound 1. In one embodiment, provided herein is a solid form comprising (i) a cocrystal comprising Compound 1 and nicotinamide and (ii) one or more additional crystal forms of Compound 1. Provided herein are various embodiments, preparations, or modifications of a cocrystal comprising Compound 1 and nicotinamide.

In one embodiment, Form 6 is a THF and water solvate comprising Compound 1 and nicotinamide. In another embodiment, Form 6 is crystalline.

In certain embodiments, Form 6 is obtained by grinding experiments comprising 1) adding Compound 1, nicotinamide and a solvent into a grinding container containing grinding balls; 2) shaking the container for a period of time at a particular frequency; 3) collecting the resulting solid by filtration (e.g., centrifuge filtration). In certain embodiments, the solvent is a mixture of THF and water (50/50). In one embodiment, the molar ratio of Compound 1 and nicotinamide is about 1:1.1. In one embodiment, the period of time is about 1 hour. In one embodiment, the frequency is about 30 Hz.

Figure 29:
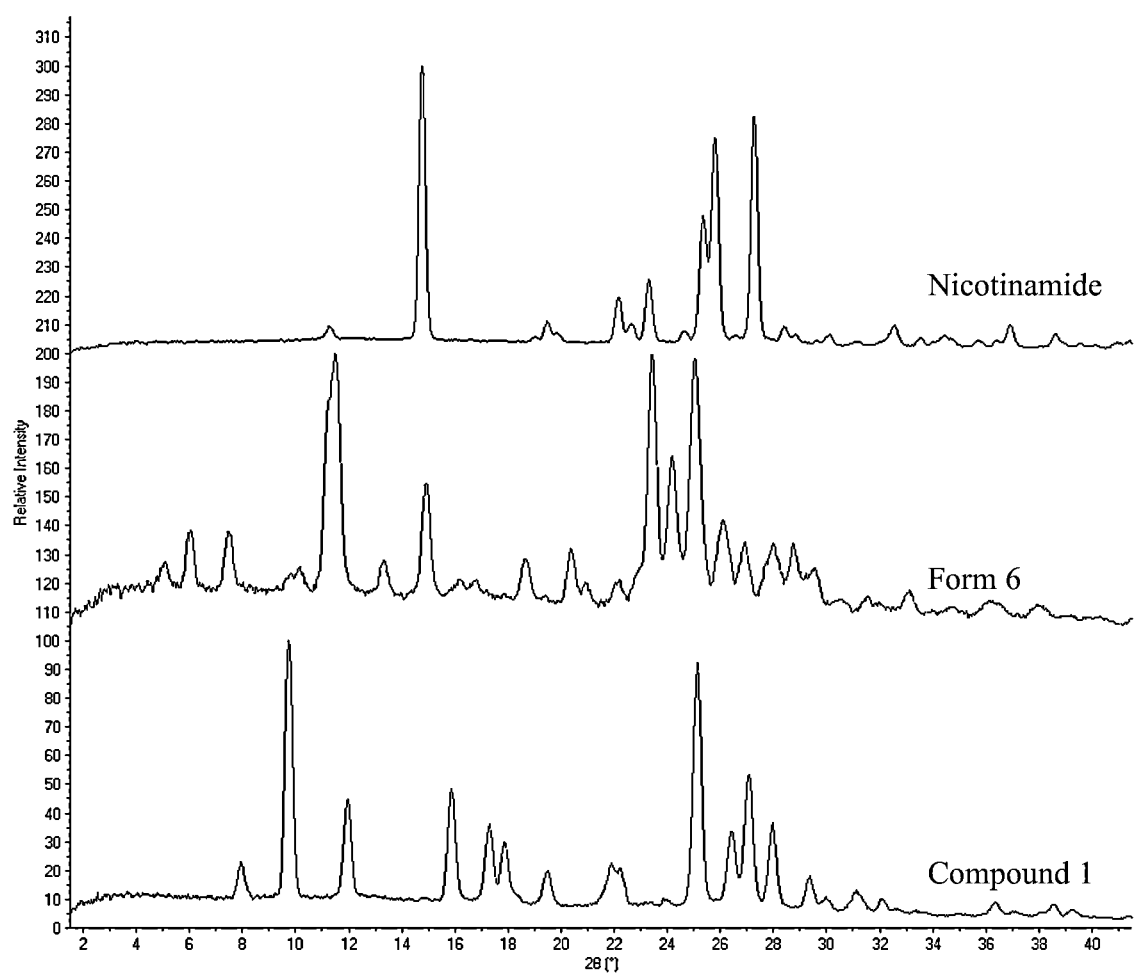
FIG. 29 depicts an X-ray powder diffractogram stack plot of Compound 1, Form 6 and nicotinamide.

In certain embodiments, a solid form provided herein, e.g., Form 6, is substantially crystalline, as indicated by, e.g., X-ray powder diffraction measurements. In one embodiment, Form 6 of Compound 1 has an X-ray powder diffraction pattern substantially as shown in FIG. 29 (middle pattern). In one embodiment, Form 6 of Compound 1 has one or more characteristic X-ray powder diffraction peaks at a two-theta angle of approximately 6.02, 7.46, 11.5, 13.3, 14.9, 18.66, 20.38, 23.42, 24.18, 25.06, 26.1, 26.9, 27.98 or 28.78 degrees as depicted in FIG. 29. In a specific embodiment, Form 6 of Compound 1 has one, two, three, four, five, six, seven or eight characteristic X-ray powder diffraction peaks at a two-theta angle of approximately 6.02, 7.46, 11.5, 14.9, 23.42, 24.18, 25.06 or 26.1 degrees. In another embodiment, Form 6 of Compound 1 has one, two, three or four characteristic X-ray powder diffraction peaks at a two-theta angle of approximately 11.5, 23.42, 24.18 or 25.06 degrees. In another embodiment, Form 6 of Compound 1 has one, two, three, four, five, six, seven, eight, nine, ten, eleven, twelve, thirteen or fourteen characteristic X-ray powder diffraction peaks as set forth in Table 17.

Figure 30:
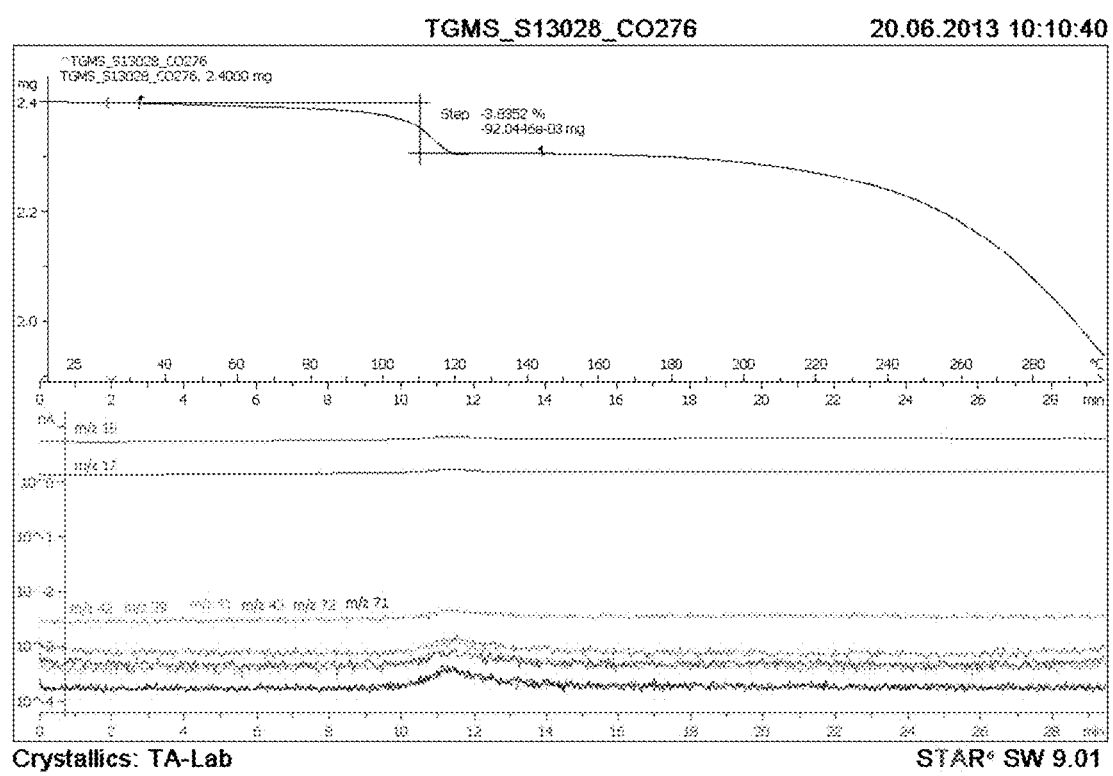
FIG. 30 depicts a thermogravimetric analysis coupled with mass spectroscopy of Form 6.

In one embodiment, provided herein is Form 6 having a thermogravimetric (TGA) thermograph corresponding substantially to the representative TGA thermogram as depicted in FIG. 30. In certain embodiments, the crystalline form exhibits a TGA thermogram comprising a total mass loss of approximately 3.8% of the total mass of the sample between approximately 35° C. and approximately 145° C. when heated from approximately 25° C. to approximately 300° C. Thus, in certain embodiments, the crystalline form loses about 3.8% of its total mass when heated from about ambient temperature to about 300° C.

Figure 31:
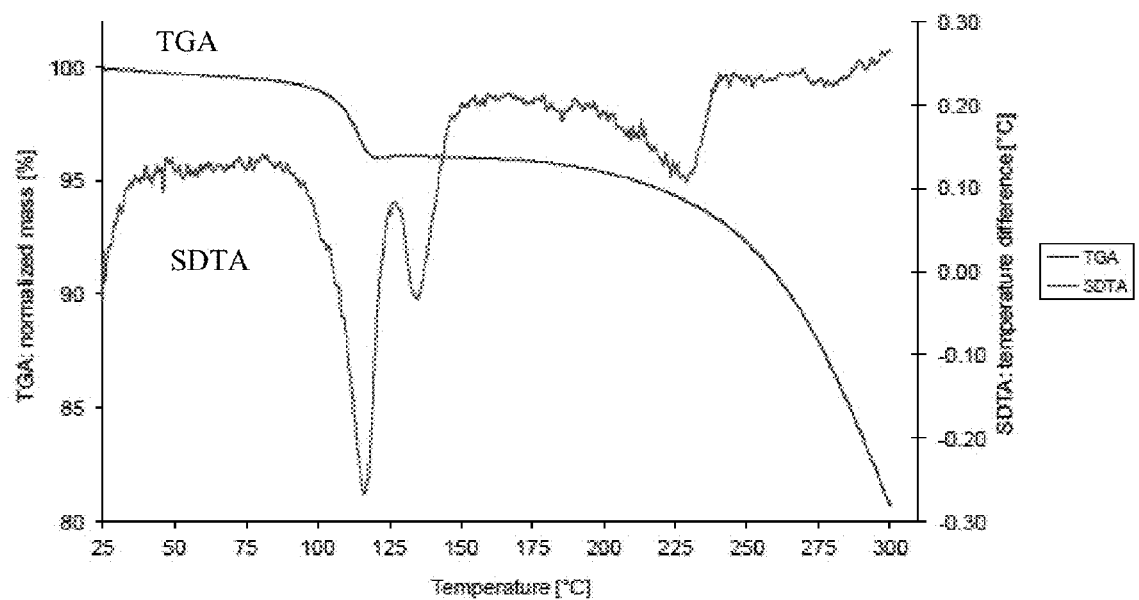
FIG. 31 depicts a thermogravimetrical analysis and single differential thermal analysis of Form 6.

In one embodiment, provided herein is Form 6 having a single differential thermal analysis (SDTA) thermogram as depicted in FIG. 31 comprising an endothermic event with a maximum at about 89° C., followed by immediate decomposition at about 200° C., when heated from approximately 25° C. to approximately 300° C.

In still another embodiment, Form 6 of Compound 1 is substantially pure. In certain embodiments, the substantially pure Form 6 of Compound 1 is substantially free of other solid forms, e.g., amorphous form. In certain embodiments, the purity of the substantially pure Form 6 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.7 Cocrystal Form 7 Comprising Compound 1 and Succinic Acid

Provided herein is cocrystal Form 7, comprising Compound 1 and succinic acid. In one embodiment, provided herein is a solid form comprising Compound 1 and succinic acid that is substantially crystalline. In one embodiment, provided herein is a solid form comprising (i) a cocrystal comprising Compound 1 and succinic acid and (ii) an amorphous form of Compound 1. In one embodiment, provided herein is a solid form comprising (i) a cocrystal comprising Compound 1 and succinic acid and (ii) one or more additional crystal forms of Compound 1. Provided herein are various embodiments, preparations, or modifications of a cocrystal comprising Compound 1 and succinic acid.

In one embodiment, Form 7 is a hydrate comprising Compound 1 and succinic acid. In another embodiment, Form 7 is crystalline.

In certain embodiments, Form 7 is obtained by grinding experiments comprising 1) adding Compound 1, succinic acid and a solvent into a grinding container containing grinding balls; 2) shaking the container for a period of time at a particular frequency; 3) collecting the resulting solid by filtration (e.g., centrifuge filtration). In certain embodiments, the solvent is a mixture of methanol and water (50/50). In one embodiment, the molar ratio of Compound 1 and succinic acid is about 1:1.1. In one embodiment, the period of time is about 1 hour. In one embodiment, the frequency is about 30 Hz.

Figure 35:
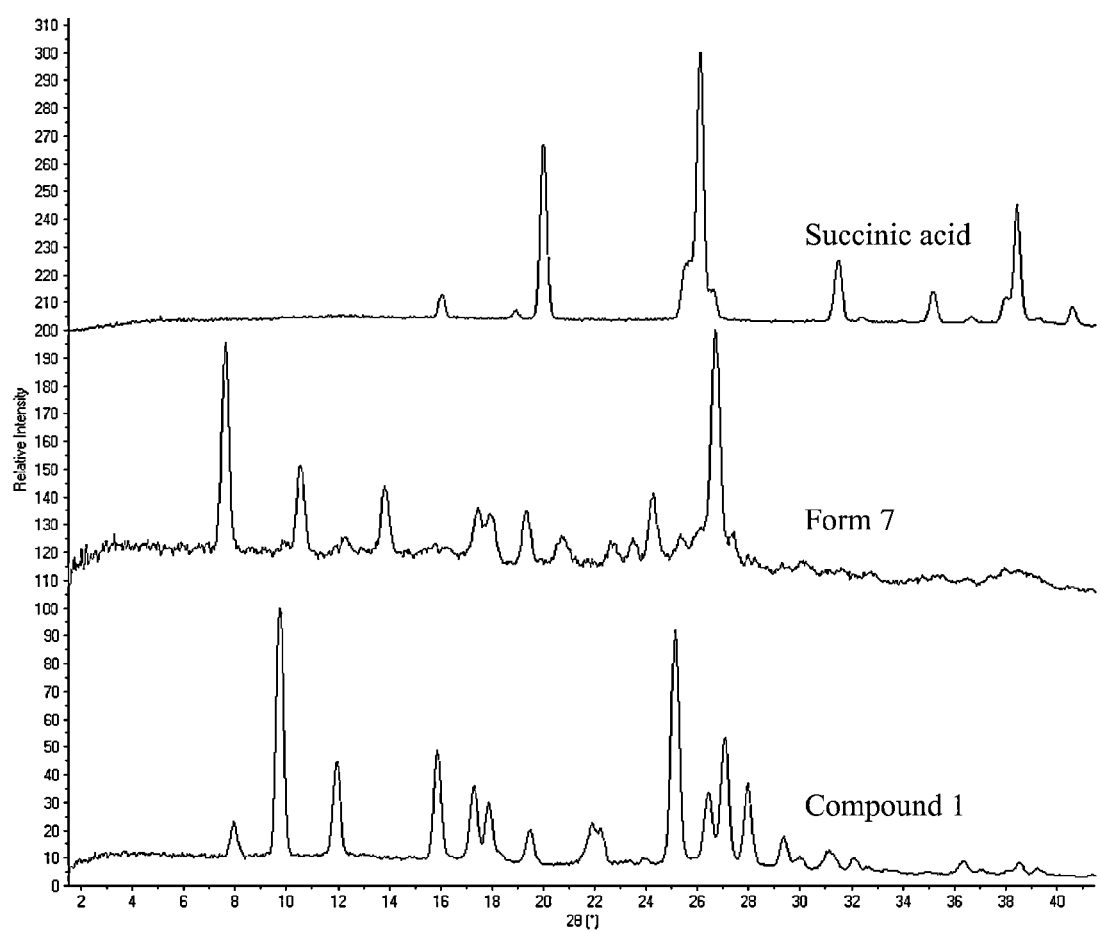
FIG. 35 depicts an X-ray powder diffractogram stack plot of Compound 1, Form 7 and succinic acid.

In certain embodiments, a solid form provided herein, e.g., Form 7, is substantially crystalline, as indicated by, e.g., X-ray powder diffraction measurements. In one embodiment, Form 7 of Compound 1 has an X-ray powder diffraction pattern substantially as shown in FIG. 35 (middle pattern). In one embodiment, Form 7 of Compound 1 has one or more characteristic X-ray powder diffraction peaks at a two-theta angle of approximately 7.62, 10.54, 13.82, 17.46, 17.94, 19.34, 24.26, 26.7 or 27.38 degrees as depicted in FIG. 35. In a specific embodiment, Form 7 of Compound 1 has one, two, three, four, five, six, seven or eight characteristic X-ray powder diffraction peaks at a two-theta angle of approximately 7.62, 10.54, 13.82, 17.46, 17.94, 19.34, 24.26 or 26.7 degrees. In another embodiment, Form 7 of Compound 1 has one, two, three or four characteristic X-ray powder diffraction peaks at a two-theta angle of approximately 7.62, 10.54, 13.82 or 26.7 degrees. In another embodiment, Form 7 of Compound 1 has one, two, three, four, five, six, seven, eight or nine characteristic X-ray powder diffraction peaks as set forth in Table 18.

Figure 36:
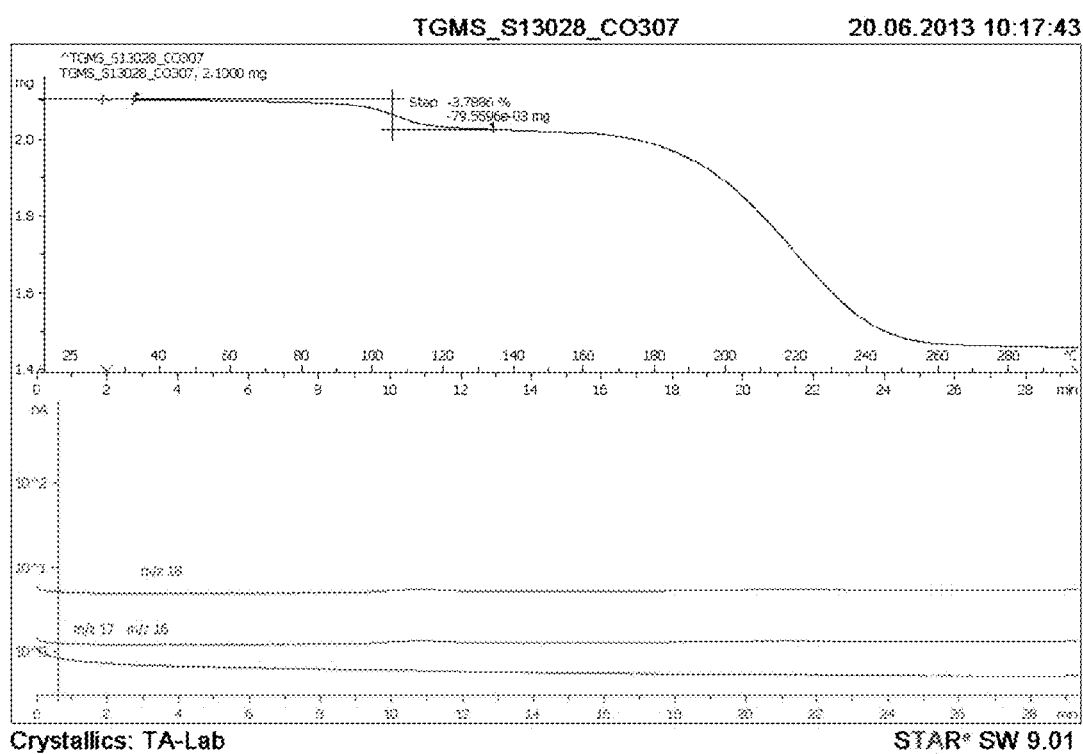
FIG. 36 depicts a thermogravimetric analysis coupled with mass spectroscopy of Form 7.

In one embodiment, provided herein is Form 7 having a thermogravimetric (TGA) thermogram corresponding substantially to the representative TGA thermogram as depicted in FIG. 36. In certain embodiments, the crystalline form exhibits a TGA thermogram comprising a total mass loss of approximately 3.8% of the total mass of the sample between approximately 35° C. and approximately 145° C. when heated from approximately 25° C. to approximately 300° C. Thus, in certain embodiments, the crystalline form loses about 3.8% of its total mass when heated from about ambient temperature to about 300° C.

Figure 37:
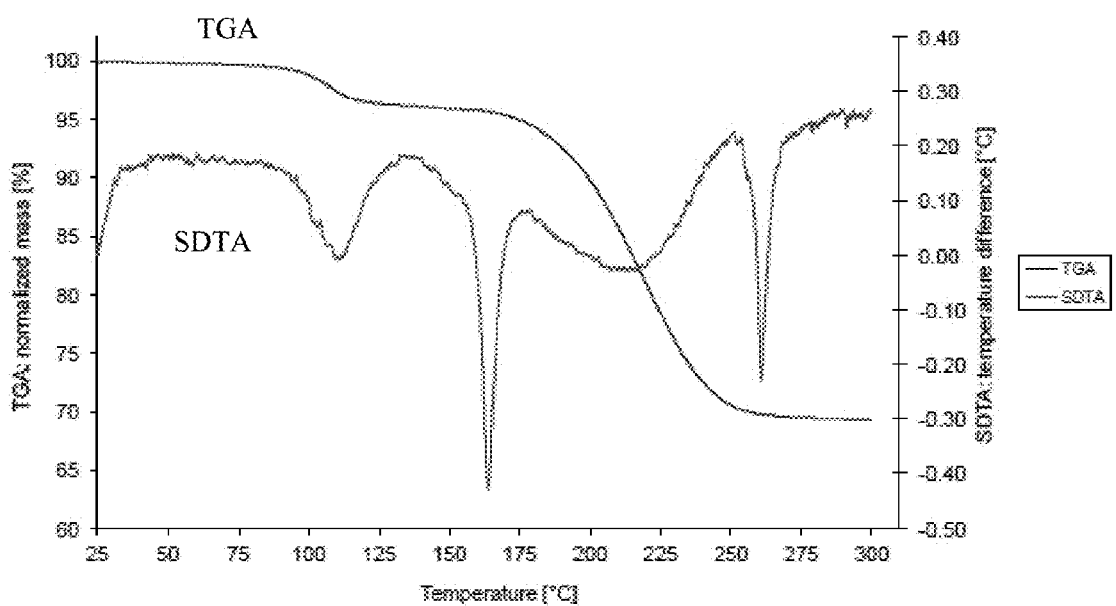
FIG. 37 depicts a thermogravimetrical analysis and single differential thermal analysis of Form 7.

In one embodiment, provided herein is Form 7 having a single differential thermal analysis (SDTA) thermogram as depicted in FIG. 37 comprising an endothermic event with a maximum at about 108.8° C., followed by immediate decomposition at about 163.4° C., when heated from approximately 25° C. to approximately 300° C.

In still another embodiment, Form 7 of Compound 1 is substantially pure. In certain embodiments, the substantially pure Form 7 of Compound 1 is substantially free of other solid forms, e.g., amorphous form. In certain embodiments, the purity of the substantially pure Form 7 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.8 Cocrystal Form 8 Comprising Compound 1 and Maleic Acid

Provided herein is cocrystal Form 8, comprising Compound 1 and maleic acid. In one embodiment, provided herein is a solid form comprising Compound 1 and maleic acid that is substantially crystalline. In one embodiment, provided herein is a solid form comprising (i) a cocrystal comprising Compound 1 and maleic acid and (ii) an amorphous form of Compound 1. In one embodiment, provided herein is a solid form comprising (i) a cocrystal comprising Compound 1 and maleic acid and (ii) one or more additional crystal forms of Compound 1. Provided herein are various embodiments, preparations, or modifications of a cocrystal comprising Compound 1 and maleic acid.

In one embodiment, Form 8 is a hydrate comprising Compound 1 and maleic acid. In another embodiment, Form 8 is crystalline.

In certain embodiments, Form 8 is obtained by grinding experiments comprising 1) adding Compound 1, maleic acid and a solvent into a grinding container containing grinding balls; 2) shaking the container for a period of time at a particular frequency; 3) collecting the resulting solid by filtration (e.g., centrifuge filtration). In certain embodiments, the solvent is a mixture of methanol and water (50/50). In one embodiment, the molar ratio of Compound 1 and maleic acid is about 1:1.1. In one embodiment, the period of time is about 1 hour. In one embodiment, the frequency is about 30 Hz.

Figure 41:
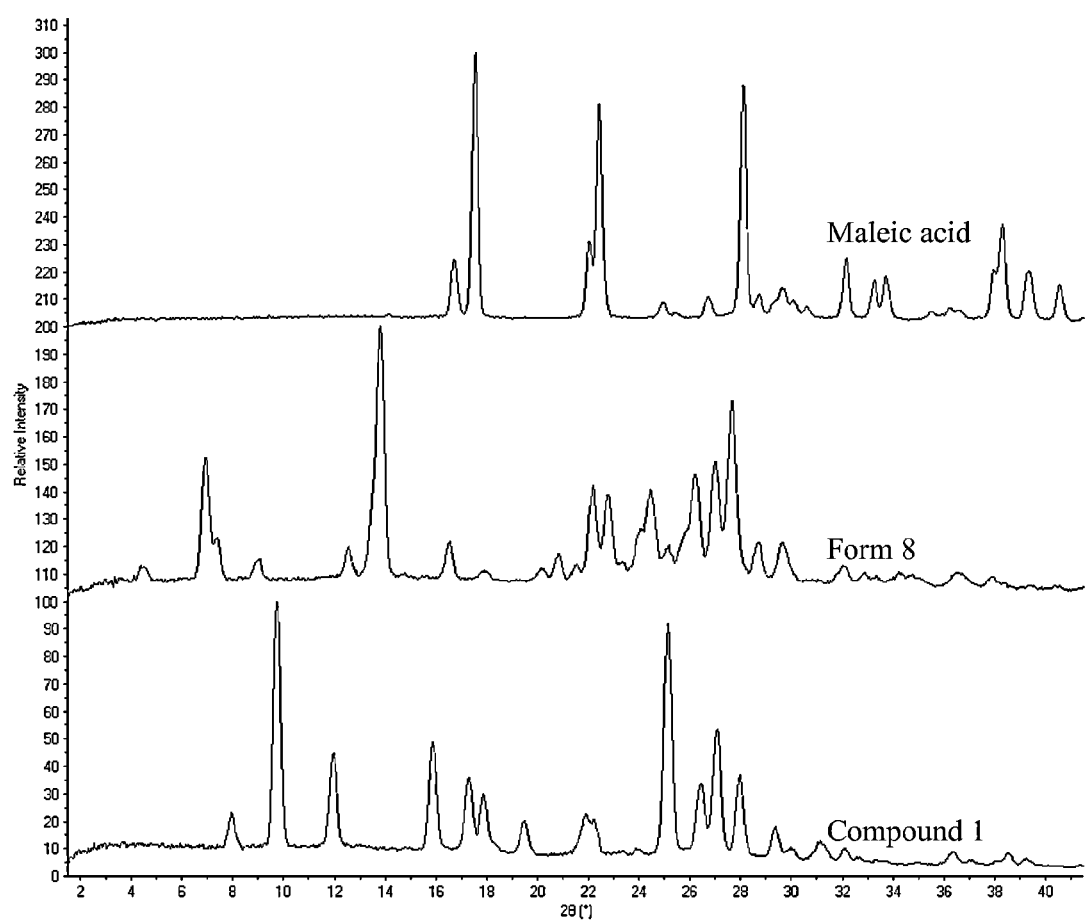
FIG. 41 depicts an X-ray powder diffractogram stack plot of Compound 1, Form 8 and maleic acid.

In certain embodiments, a solid form provided herein, e.g., Form 8, is substantially crystalline, as indicated by, e.g., X-ray powder diffraction measurements. In one embodiment, Form 8 of Compound 1 has an X-ray powder diffraction pattern substantially as shown in FIG. 41 (middle pattern). In one embodiment, Form 8 of Compound 1 has one or more characteristic X-ray powder diffraction peaks at a two-theta angle of approximately 6.94, 12.54, 13.82, 16.54, 20.82, 22.18, 22.78, 24.46, 26.22, 26.98, 27.66, 28.7 or 29.66 degrees as depicted in FIG. 41. In a specific embodiment, Form 8 of Compound 1 has one, two, three, four, five, six, seven or eight characteristic X-ray powder diffraction peaks at a two-theta angle of approximately 6.94, 13.82, 22.18, 22.78, 24.46, 26.22, 26.98 or 27.66 degrees. In another embodiment, Form 8 of Compound 1 has one, two, three or four characteristic X-ray powder diffraction peaks at a two-theta angle of approximately 6.94, 13.82, 26.98 or 27.66 degrees. In another embodiment, Form 8 of Compound 1 has one, two, three, four, five, six, seven, eight, nine, ten, eleven, twelve or thirteen characteristic X-ray powder diffraction peaks as set forth in Table 19.

Figure 42:
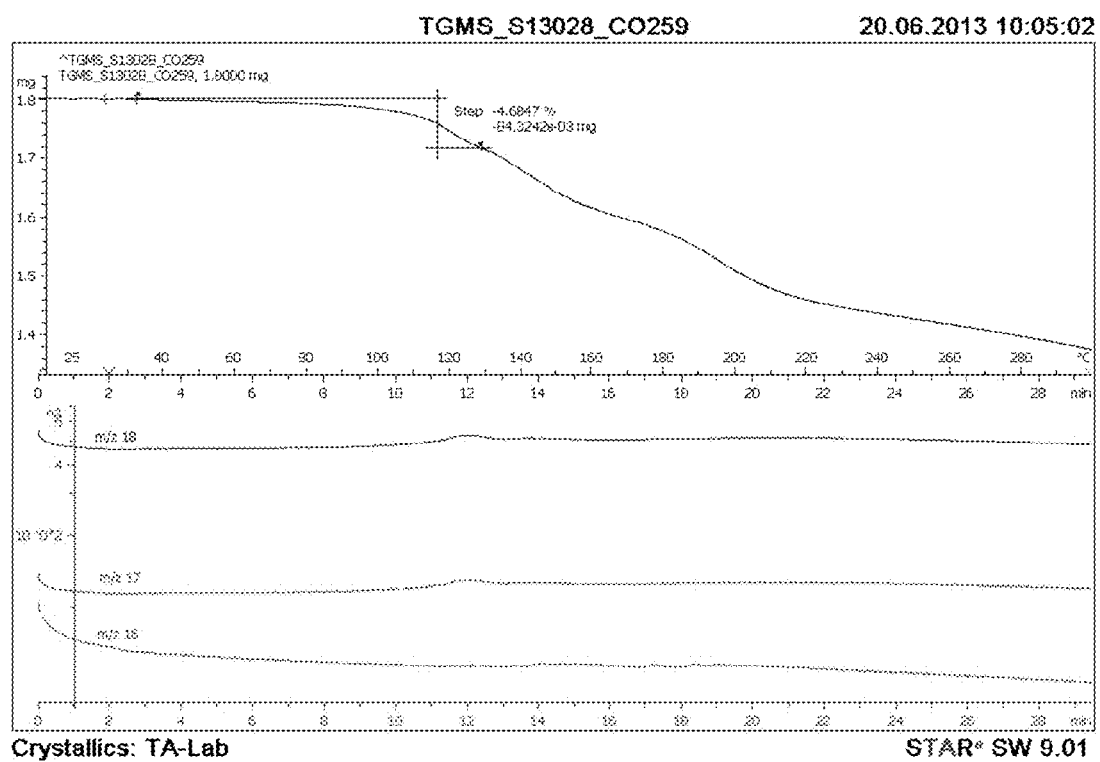
FIG. 42 depicts a thermogravimetric analysis coupled with mass spectroscopy of Form 8.

In one embodiment, provided herein is Form 8 having a thermogravimetric (TGA) thermograph corresponding substantially to the representative TGA thermogram as depicted in FIG. 42. In certain embodiments, the crystalline form exhibits a TGA thermogram comprising a total mass loss of approximately 4.6% of the total mass of the sample between approximately 35° C. and approximately 145° C. when heated from approximately 25° C. to approximately 300° C. Thus, in certain embodiments, the crystalline form loses about 4.6% of its total mass when heated from about ambient temperature to about 300° C.

Figure 43:
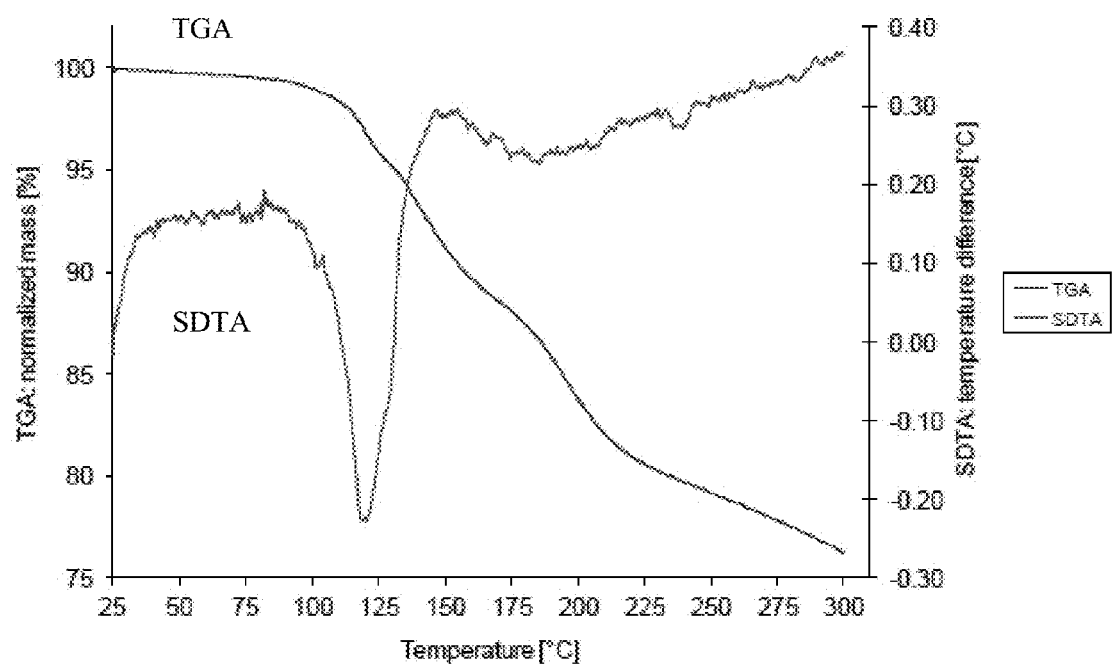
FIG. 43 depicts a thermogravimetrical analysis and single differential thermal analysis of Form 8.

In one embodiment, provided herein is Form 8 having a single differential thermal analysis (SDTA) thermogram as depicted in FIG. 43 comprising an endothermic event with a maximum at about 118.7° C., followed by immediate decomposition, when heated from approximately 25° C. to approximately 300° C.

In still another embodiment, Form 8 of Compound 1 is substantially pure. In certain embodiments, the substantially pure Form 8 of Compound 1 is substantially free of other solid forms, e.g., amorphous form. In certain embodiments, the purity of the substantially pure Form 8 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.4 Methods of Use

The solid forms and the pharmaceutical compositions provided herein can be used in all the methods provided herein. The solid forms and the pharmaceutical compositions provided herein can be used in the treatment of all diseases, disorders or conditions provided herein.

Provided herein are methods for treating or preventing a cancer, comprising administering a solid form of Compound 1 provided herein or a pharmaceutical composition thereof to a patient having a cancer.

In some embodiments, the cancer is an advanced unresectable solid tumor, or a hematologic malignancy. For example, the hematologic malignancy is CLL, NHL, or MM. In some such embodiments, the cancer has progressed on standard anti-cancer therapy, or the patient is not able to tolerate standard anti-cancer therapy. In yet others, the cancer is a cancer for which no approved therapy exists. In some embodiments, the cancer is resistant to standard therapy. In another, the patient has relapsed after standard therapy. In one embodiment, the cancer is a neoplasm metastasis.

In certain embodiments, the cancer is a bloodborne tumor.

In certain embodiments, the cancer is a lymphoma, a leukemia or a multiple myeloma.

In certain embodiments, the cancer is non-Hodgkin's lymphoma. In certain embodiments, the non-Hodgkin's lymphoma is diffuse large B-cell lymphoma (DLBCL), follicular lymphoma (FL), acute myeloid leukemia (AML), mantle cell lymphoma (MCL), or ALK$^+$ anaplastic large cell lymphoma. In one embodiment, the non-Hodgkin's lymphoma is advanced solid non-Hodgkin's lymphoma. In one embodiment, the non-Hodgkin's lymphoma is diffuse large B-cell lymphoma (DLBCL).

In certain embodiments, the cancer is a B-cell lymphoma.

In certain embodiments, the B-cell lymphoma is a B-cell non-Hodgkin's lymphoma selected from diffuse large B-cell lymphoma, Burkitt's lymphoma/leukemia, mantle cell lymphoma, mediastinal (thymic) large B-cell lymphoma, follicular lymphoma, marginal zone lymphoma (including extranodal marginal zone B-cell lymphoma and nodal marginal zone B-cell lymphoma), lymphoplasmacytic lymphoma/Waldenstrom macroglobulinemia. In some embodiments, the B-cell lymphoma is chronic lymphocytic leukemia/small lymphocytic lymphoma (CLL/SLL). In one embodiment, the B-cell lymphoma is Waldenstrom macroglobulinemia.

In one embodiment, the B-cell non-Hodgkin's lymphoma is refractory B-cell non-Hodgkin's lymphoma. In one embodiment, the B-cell non-Hodgkin's lymphoma is relapsed B-cell non-Hodgkin's lymphoma.

In certain embodiments, the cancer is a T-cell lymphoma.

The B-cell disorders chronic lymphocytic leukemia/small lymphocytic lymphoma (CLL/SLL) represent 2 ends of a spectrum of the same disease process differing in the degree of blood/marrow involvement (CLL) versus lymph node involvement (SLL).

In another embodiment, the cancer is CLL characterized by deletion of chromosome 11q22, loss of ATM expression, mutation of IgVH, wild type IgVH, wild type p53/ATM, mutation of p53 or dysfunctional p53.

In other embodiments, the cancer is a multiple myeloma.

In certain embodiments, the cancer is a cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

In other embodiments, the cancer is a solid tumor. In certain embodiments, the solid tumor is a relapsed or refractory solid tumor.

In other embodiments, the solid tumor can be an advanced solid tumor.

In other embodiments, the solid tumor can be a neuroendocrine tumor, glioblastoma multiforme (GBM), hepatocellular carcinoma (HCC), breast cancer, colorectal cancer (CRC), salivary cancer, pancreatic cancer, adenocystic cancer, adrenal cancer, esophageal cancer, renal cancer, leiomyosarcoma, paraganglioma, head and neck squamous cell carcinoma, E-twenty six (ETS) overexpressing castration-resistant prostate cancer or E-twenty six (ETS) overexpressing Ewings sarcoma.

In one embodiment, the solid tumor is a neuroendocrine tumor. In certain embodiments, the neuroendocrine tumor is a neuroendocrine tumor of gut origin. In certain embodiments, the neuroendocrine tumor is of non-pancreatic origin. In certain embodiments, the neuroendocrine tumor is non-pancreatic of gut origin. In certain embodiments, the neuroendocrine tumor is of unknown primary origin. In certain embodiments, the neuroendocrine tumor is a symptomatic endocrine producing tumor or a nonfunctional tumor. In certain embodiments, the neuroendocrine tumor is locally unresectable, metastatic moderate, well differentiated, low (grade 1) or intermediate (grade 2). In certain embodiments, the neuroendocrine tumor is of non-gut origin. In one embodiment, the neuroendocrine tumor of non-gut origin, is rapamycin resistant. In one embodiment, the neuroendocrine tumor of non-gut origin is a bronchial neuroendocrine tumor, or a neuroendocrine tumor with origin in an organ above the diaphragm, for example, a laryngeal neuroendocrine tumor, a pharyngeal neuroendocrine tumor, or a thyroid neuroendocrine tumor. In one embodiment, the neuroendocrine tumor of non-gut origin is a symptomatic endocrine producing tumor or a nonfunctional tumor. In one embodiment, the neuroendocrine tumor of non-gut origin is locally unresectable, metastatic moderate, well differentiated, low (grade 1) or intermediate (grade 2).

In one embodiment, the solid tumor is non-small cell lung cancer (NSCLC).

In another embodiments the solid tumor is glioblastoma multiforme (GBM).

In another embodiment, the solid tumor is hepatocellular carcinoma (HCC).

In another embodiment, the solid tumor is breast cancer. In one embodiment, the breast cancer is hormone receptor positive. In one embodiment, the breast cancer is estrogen receptor positive (ER+, ER+/Her2 or ER+/Her2+). In one embodiment, the breast cancer is estrogen receptor negative (ER−/Her2+). In one embodiment, the breast cancer is triple negative (TN) (breast cancer that does not express the genes and/or protein corresponding to the estrogen receptor (ER), progesterone receptor (PR), and that does not overexpress the Her2/neu protein).

In one embodiment, the solid tumor is an advanced solid tumor.

In another embodiment, the cancer is head and neck squamous cell carcinoma.

In another embodiment, the cancer is E-twenty six (ETS) overexpressing castration-resistant prostate cancer.

In another embodiment, the cancer is E-twenty six (ETS) overexpressing Ewings sarcoma.

In another embodiment, the cancer is head and neck squamous cell carcinoma (HNSCC) characterized by deletion of chromosome 11q22 or loss of ataxia telangiectasia mutated (ATM) expression.

In another embodiment, the cancer is glioblastoma multiforme (GBM) characterized by O6-methylguanine-DNA methyltransferase (MGMT) methylation.

In other embodiments, the cancer is a cancer associated with the pathways involving mTOR, PI3K, or Akt kinases and mutants or isoforms thereof. Other cancers within the scope of the methods provided herein include those associated with the pathways of the following kinases: PI3Kα, PI3Kβ, PI3Kβ, KDR, GSK3α, GSK3β, ATM, ATX, ATR, cFMS, and/or DNA-PK kinases and mutants or isoforms thereof. In some embodiments, the cancers associated with mTOR/PI3K/Akt pathways include solid and blood-borne tumors, for example, multiple myeloma, mantle cell lymphoma, diffused large B-cell lymphoma, acute myeloid lymphoma, follicular lymphoma, chronic lymphocytic leukemia; and solid tumors, for example, breast, lung, endometrial, ovarian, gastric, cervical, and prostate cancer; glioblastoma; renal carcinoma; hepatocellular carcinoma; colon carcinoma; neuroendocrine tumors; head and neck tumors; and sarcomas, such as Ewing's sarcoma.

In certain embodiments, provided herein are methods for achieving a Response Evaluation Criteria in Solid Tumors (for example, RECIST 1.1) of complete response, partial response or stable disease in a patient having a solid tumor, comprising administering a solid form of Compound 1 provided herein or a pharmaceutical composition thereof to said patient. In certain embodiments, provided herein are methods for achieving a National Cancer Institute-Sponsored Working Group on Chronic Lymphocytic Leukemia (NCI-WG CLL) of complete response, partial response or stable disease in a patient having leukemia, comprising administering a solid form of Compound 1 provided herein or a pharmaceutical composition thereof to said patient. In certain embodiments, provided herein are methods for achieving a Prostate Cancer Working Group 2 (PCWG2) Criteria of complete response, partial response or stable disease in a patient having prostate cancer, comprising administering a solid form of Compound 1 provided herein or a pharmaceutical composition thereof to said patient. In certain embodiments, provided herein are methods for achieving an International Workshop Criteria (IWC) for non-Hodgkin's lymphoma of complete response, partial response or stable disease in a patient having non-Hodgkin's lymphoma, comprising administering a solid form of Compound 1 provided herein or a pharmaceutical composition thereof to said patient. In certain embodiments, provided herein are methods for achieving an International Uniform Response Criteria (IURC) for multiple myeloma of complete response, partial response or stable disease in a patient having multiple myeloma, comprising administering a solid form of Compound 1 provided herein or a pharmaceutical composition thereof to said patient. In certain embodiments, provided herein are methods for achieving a Responses Assessment for Neuro-Oncology (RANO) Working Group for glioblastoma multiforme of complete response, partial response or stable disease in a patient having glioblastoma multiforme, comprising administering a solid form of Compound 1 provided herein or a pharmaceutical composition thereof to said patient.

In certain embodiments, provided herein are methods for increasing survival without disease progression of a patient having a cancer, comprising administering a solid form of Compound 1 provided herein or a pharmaceutical composition thereof to said patient.

In certain embodiments, provided herein are methods for treating a cancer, the methods comprising administering a solid form of Compound 1 provided herein or a pharmaceutical composition thereof to a patient having a cancer, wherein the treatment results in prevention or retarding of clinical progression, such as cancer-related cachexia or increased pain.

In some embodiments, provided herein are methods for treating a cancer, the methods comprising administering a solid form of Compound 1 provided herein or a pharmaceutical composition thereof to a patient having a cancer, wherein the treatment results in one or more of inhibition of disease progression, increased Time To Progression (TTP), increased Progression Free Survival (PFS), and/or increased Overall Survival (OS), among others.

Provided herein are methods of using the solid forms and compositions provided herein in the treatment, prevention, or management of conditions and disorders including, but not limited to: a bloodborne tumor, a lymphoma, a leukemia, a multiple myeloma, non-Hodgkin's lymphoma, large B-cell lymphoma (DLBCL), follicular lymphoma (FL), acute myeloid leukemia (AML), mantle cell lymphoma (MCL), ALK+ anaplastic large cell lymphoma, advanced solid non-Hodgkin's lymphoma, diffuse large B-cell lymphoma (DLBCL), B-cell lymphoma, B-cell non-Hodgkin's lymphoma, diffuse large B-cell lymphoma, Burkitt's lymphoma/leukemia, mantle cell lymphoma, mediastinal (thymic) large B-cell lymphoma, follicular lymphoma, marginal zone lymphoma (including extranodal marginal zone B-cell lymphoma and nodal marginal zone B-cell lymphoma), lymphoplasmacytic lymphoma/Waldenstrom macroglobulinemia, chronic lymphocytic leukemia/small lymphocytic lymphoma (CLL/SLL), Waldenstrom macroglobulinemia, refractory B-cell non-Hodgkin's lymphoma, relapsed B-cell non-Hodgkin's lymphoma, T-cell lymphoma, a multiple myeloma, a solid tumor, a relapsed or refractory solid tumor, a neuroendocrine tumor, the neuroendocrine tumor, a neuroendocrine tumor of gut origin, neuroendocrine tumor, non-pancreatic origin, neuroendocrine tumor, a symptomatic endocrine producing tumor, a nonfunctional tumor, a bronchial neuroendocrine tumor, a laryngeal neuroendocrine tumor, a pharyngeal neuroendocrine tumor, a thyroid neuroendocrine tumor, a symptomatic endocrine producing tumor, a nonfunctional tumor, a non-small cell lung cancer (NSCLC), a glioblastoma multiforme (GBM), a hepatocellular carcinoma (HCC), a breast cancer, a head and neck squamous cell carcinoma, an E-twenty six (ETS) overexpressing castration-resistant prostate cancer, an E-twenty six (ETS) overexpressing Ewings sarcoma, a head and neck squamous cell carcinoma (HNSCC) characterized by deletion of chromosome 11q22 or loss of ataxia telangiectasia mutated (ATM) expression, a glioblastoma multiforme (GBM) characterized by 06-methylguanine-DNA methyltransferase (MGMT) methylation, a cancer associated with the pathways involving mTOR, PI3K, or Akt kinases and mutants or isoforms, cancers associated with the pathways of the following kinases: PI3Kα, PI3Kβ, PI3δ, KDR, GSK3α, GSK3β, ATM, ATX, ATR, cFMS, and/or DNA-PK kinases and mutants or isoforms, multiple myeloma, mantle cell lymphoma, diffused large B-cell lymphoma, acute myeloid lymphoma, follicular lymphoma, and solid tumors, for example, breast, lung, endometrial, ovarian, gastric, cervical, and prostate cancer, glioblastoma, renal carcinoma, hepatocellular carcinoma, colon carcinoma, neuroendocrine tumors, head and neck tumors, and sarcomas, such as Ewing's sarcoma.

5.5 Pharmaceutical Compositions

Solid forms of Compound 1 provided herein are useful for the preparation of pharmaceutical compositions, comprising an effective amount of a solid form of Compound 1 and a pharmaceutically acceptable carrier or vehicle. In some embodiments, the pharmaceutical compositions described herein are suitable for oral, parenteral, mucosal, transdermal or topical administration.

In certain embodiments, provided herein are compositions comprising one or more solid forms of Compound 1. Also provided herein are compositions comprising: (i) one or more solid forms of Compound 1 provided herein (e.g., one or more cocrystal forms or mixtures thereof), and (ii) other active or inactive ingredient(s).

In one embodiment, the pharmaceutical compositions provided herein comprise a solid form of Compound 1 and one or more pharmaceutically acceptable excipients or carriers. In one embodiment, the pharmaceutical compositions provided herein comprise Form 1 of Compound 1 and one or more pharmaceutically acceptable excipients or carriers. In one embodiment, the pharmaceutical compositions provided herein comprise Form 2 of Compound 1 and one or more pharmaceutically acceptable excipients or carriers. In one embodiment, the pharmaceutical compositions provided herein comprise Form 3 of Compound 1 and one or more pharmaceutically acceptable excipients or carriers. In one embodiment, the pharmaceutical compositions provided herein comprise Form 4 of Compound 1 and one or more pharmaceutically acceptable excipients or carriers. In one embodiment, the pharmaceutical compositions provided herein comprise Form 5 of Compound 1 and one or more pharmaceutically acceptable excipients or carriers. In one embodiment, the pharmaceutical compositions provided herein comprise Form 6 of Compound 1 and one or more pharmaceutically acceptable excipients or carriers. In one embodiment, the pharmaceutical compositions provided herein comprise Form 7 of Compound 1 and one or more pharmaceutically acceptable excipients or carriers. In one embodiment, the pharmaceutical compositions provided herein comprise Form 8 of Compound 1 and one or more pharmaceutically acceptable excipients or carriers. In one embodiment, the pharmaceutical compositions provided herein comprise one or more of the following solid forms or a mixture thereof: Form 1, Form 2, Form 3, Form 4, Form 5, Form 6, Form 7 and Form 8 of Compound 1 and one or more pharmaceutically acceptable excipients or carriers.

In one embodiment, the pharmaceutically acceptable excipients and carriers are selected from binders, diluents, disintegrants and lubricants. In another embodiment, the pharmaceutically acceptable excipients and carriers further include one or more antioxidants (e.g., EDTA or BHT).

In certain embodiments, the binders include, but are not limited to, cellulose (e.g., microcrystalline cellulose, such as AVICEL® PH 101, AVICEL® PH112, and AVICEL® PH 102) and starch (e.g., pregelatinized starch (STARCH 1500®)). In one embodiment, the binder is cellulose. In another embodiment, the binder is microcrystalline cellulose. In yet another embodiment, the binder is AVICEL® PH 101. In yet another embodiment, the binder is AVICEL® PH 102. In yet another embodiment, the binder is starch. In yet another embodiment, the binder is pregelatinized starch. In still another embodiment, the binder is STARCH 1500®.

In certain embodiments, the diluents include, but are not limited to, lactose (e.g., lactose monohydrate (FAST FLO® 316) and lactose anhydrous), cellulose (e.g., microcrystalline cellulose, such as AVICEL® PH 101 and AVICEL® PH 102). In one embodiment, the diluent is lactose. In another embodiment, the diluent is lactose monohydrate. In yet another embodiment, the diluent is FAST FLO® 316. In yet another embodiment, the diluent is lactose anhydrous. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102).

In certain embodiments, the disintegrants include, but are not limited to, starch (e.g., corn starch) and carboxymethyl cellulose (e.g., croscarmellose sodium, such as AC-DI-SOL®). In one embodiment, the disintegrant is starch. In another embodiment, the disintegrant is corn starch. In yet another embodiment, the disintegrant is carboxymethyl cellulose. In yet another embodiment, the disintegrant is croscarmellose sodium. In still another embodiment, the disintegrant is AC-DI-SOL®.

In certain embodiments, the lubricants include, but are not limited to, starch (e.g., corn starch), magnesium stearate, and stearic acid. In one embodiment, the lubricant is starch. In another embodiment, the lubricant is corn starch. In yet another embodiment, the lubricant is magnesium stearate. In still another embodiment, the lubricant is stearic acid.

In another embodiment, the pharmaceutical compositions provided herein comprise a solid form of Compound 1 and one or more pharmaceutically acceptable excipients or carriers, each independently selected from carboxymethyl cellulose, cellulose, lactose, magnesium stearate, starch, and stearic acid.

In one embodiment, the pharmaceutical compositions provided herein comprise about 2.5-10% by weight of a solid form of Compound 1, about 70-90% by weight of diluent(s)/binder(s), about 1-5% by weight of disintegrant(s), and about 0.1-2% by weight of lubricant(s).

In another embodiment, the pharmaceutical compositions provided herein comprise about 10% by weight of a solid form of Compound 1, about 59.85% by weight of mannitol, about 25% by weight of microcrystalline cellulose, about 3% by weight of sodium starch glycolate, about 1% by weight of silicon dioxide, about 0.5% by weight of stearic acid, and about 0.65% by weight of magnesium stearate.

In another embodiment, the pharmaceutical compositions provided herein comprise about 10% by weight of a solid form of Compound 1, about 59.45% by weight of mannitol, about 25% by weight of microcrystalline cellulose, about 3% by weight of sodium starch glycolate, about 1% by weight of silicon dioxide, about 0.5% by weight of stearic acid, about 0.4% BHT, and about 0.65% by weight of magnesium stearate.

In another embodiment, the pharmaceutical compositions provided herein comprise about 10% by weight of a solid form of Compound 1, about 59.35% by weight of mannitol, about 25% by weight of microcrystalline cellulose, about 3% by weight of sodium starch glycolate, about 1% by weight of silicon dioxide, about 0.5% by weight of stearic acid, about 0.5% disodium EDTA, and about 0.65% by weight of magnesium stearate.

In another embodiment, the pharmaceutical compositions provided herein comprise about 10% by weight of a solid form of Compound 1, about 58.95% by weight of mannitol, about 25% by weight of microcrystalline cellulose, about 3% by weight of sodium starch glycolate, about 1% by weight of silicon dioxide, about 0.5% by weight of stearic acid, about 0.5% disodium EDTA, about 0.4% BHT, and about 0.65% by weight of magnesium stearate.

In certain embodiments, provided herein are pharmaceutical compositions comprising an opaque coating. Without being limited by theory, it was found that a more opaque coating protected the drug product from degradation. In some embodiments, the pharmaceutical composition is formulated as a tablet. In some such embodiments, the tablet is film coated. In some embodiments, the tablet is film coated to a weight gain of 1-8%. In others, the film coating is about 5% by weight of the tablet.

In certain embodiments, provided herein are pharmaceutical compositions, wherein the amounts of the recited components can independently be varied by 1%, 2%, 3%, 4%, 5%, 6%, 7%, 8%, 9%, 10%, 15%, 20% or 25%.

The pharmaceutical compositions provided herein can be provided in a unit-dosage form or multiple-dosage form. A unit-dosage form, as used herein, refers to physically discrete unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an individually packaged tablet or capsule. A unit-dosage form may be administered in fractions or multiples thereof. A multiple-dosage form is a plurality of identical unit-dosage forms packaged in a single container to be administered in segregated unit-dosage form.

In another embodiment, provided herein are unit dosage formulations that comprise between about 0.1 mg and about 2000 mg, about 1 mg and 200 mg, about 35 mg and about 1400 mg, about 125 mg and about 1000 mg, about 250 mg and about 1000 mg, or about 500 mg and about 1000 mg solid form of Compound 1, or a pharmaceutically acceptable salt, isotopologue or solid form thereof.

In a particular embodiment, provided herein are unit dosage formulation comprising about 0.1 mg, about 0.25 mg, about 0.5 mg, about 1 mg, about 2 mg, about 2.5 mg, about 5 mg, about 7.5 mg, about 8 mg, about 10 mg, about 15 mg, about 20 mg, about 25 mg, about 30 mg, about 35 mg, about 40 mg, about 45 mg, about 50 mg, about 60 mg, about 70 mg, about 75 mg, about 100 mg, about 125 mg, about 140 mg, about 150 mg, about 175 mg, about 200 mg, about 250 mg, about 280 mg, about 300 mg, about 350 mg, about 400 mg, about 500 mg, about 560 mg, about 600 mg, about 700 mg, about 750 mg, about 800 mg, about 1000 mg or about 1400 mg of a solid form of Compound 1. In a particular embodiment, provided herein are unit dosage formulations that comprise about 2.5 mg, about 5 mg, about 7.5 mg, about 8 mg, about 10 mg, about 15 mg, about 20 mg, about 25 mg, about 30 mg, about 40 mg, about 45 mg, about 50 mg, about 60 mg or about 100 mg of a solid form of Compound 1, or a pharmaceutically acceptable salt, tautomer, isotopologue or stereoisomer thereof. In a particular embodiment, provided herein are unit dosage formulations that comprise about 1 mg, about 2 mg, about 5 mg, about 7.5 mg and about 10 mg.

In some embodiments, a unit dosage form comprising Compound 1, or a pharmaceutically acceptable salt, isotopologue or solid form thereof can be administered once daily (QD), twice daily (BID), three times daily, four times daily or more often.

In certain embodiments, provided herein are methods for preparing a composition provided herein, comprising: (i) weighing out the desired amount of a solid form of Compound 1 (e.g., Form 1, Form 2, Form 3, Form 4, Form 5, Form 6, Form 7 or Form 8) and the desired amount of excipients (such as lactose monohydrate, croscarmellose sodium and/or microcrystalline cellulose); (ii) mixing or blending the solid form of Compound 1 and the excipients; (iii) passing the mixture of the solid form of Compound 1 and excipients through a screen (such as a 25 mesh screen); (iv) mixing or blending the solid form of Compound 1 and the excipients after passage through the screen; (v) weighing out the desired amount of lubricating agents (such as stearic acid and magnesium stearate); (vi) passing the lubricating agents through a screen (such as a 35 mesh screen); (vii) mixing or blending the solid form of Compound 1, the excipients and the lubricating agents; (viii) compressing the mixture of the solid form of Compound 1, the excipients and the lubricating agents (such as into a tablet form); and optionally (ix) coating the compressed mixture of the solid form of Compound 1 thereof, the excipients and the lubricating agents with a coating agent (such as Opadry pink, yellow or beige). In certain embodiments, the methods for preparing a composition provided herein are carried out in the dark, under yellow light or in the absence of UV light.

In certain embodiments, the pharmaceutical compositions provided herein comprise Form 1 of Compound 1, including substantially pure Form 1.

In certain embodiments, the pharmaceutical compositions provided herein comprise Form 2 of Compound 1, including substantially pure Form 2.

In certain embodiments, the pharmaceutical compositions provided herein comprise Form 3 of Compound 1, including substantially pure Form 3.

In certain embodiments, the pharmaceutical compositions provided herein comprise Form 4 of Compound 1, including substantially pure Form 4.

In certain embodiments, the pharmaceutical compositions provided herein comprise Form 5 of Compound 1, including substantially pure Form 5.

In certain embodiments, the pharmaceutical compositions provided herein comprise Form 6 of Compound 1, including substantially pure Form 6.

In certain embodiments, the pharmaceutical compositions provided herein comprise Form 7 of Compound 1, including substantially pure Form 7.

In certain embodiments, the pharmaceutical compositions provided herein comprise Form 8 of Compound 1, including substantially pure Form 8.

6. EXAMPLES

The following Examples are presented by way of illustration, not limitation. The following abbreviations are used in descriptions and examples:

2MXETOH: 2-Methoxyethanol
AAC: Accelerated aging conditions (48 hours at 40° C. and 75% RH)
ACN: Acetonitril
Am: Amorphous
AmPhos: p-Dimethylamino phenylditbutylphosphine
API: Active Pharmaceutical Ingredient
AS: ID for anti-solvent crystallization experiment
Boc: tert-Butoxycarbonyl
dba: Dibenzylidene acetone
DCM: Dichloromethane
DIPEA: N,N-Diisopropylethylamine
DMF: N,N-Dimethylformide
DMSO: Dimethylsulfoxide
DSC: Differential Scanning calorimetry
ECP: ID for evaporative experiment
EDTA: Ethylenediamine tetraacetate
ESI: Electrospray ionization
EtOH: Ethanol
FTIR: Fourier Transform Infra Red Spectroscopy
GRP: Grinding experiment
HF: ID for hot-filtration crystallization experiment
HPLC: High performance liquid chromatography
IPA: 2-Propanol LCMS: Liquid Chromatography with Mass Spectroscopy
MeOH: Methanol
mp: Melting point
MS: Mass spectrometry
Ms: Mesylate or methanesulfonyl
MTBE: tert-Butyl methyl ether
MTBE: methyl tert-butyl ether
NBS: N-Bromosuccinimide
NMP: N-Methyl-2-pyrrolidone
NMP: N-methylpyrrolidinone
NMR: Nuclear magnetic resonance
PSU: ID for cooling-evaporative crystallization experiment
QSA: ID for Phase 1 experiments
RH: Relative Humidity
RT: Room Temperature
S: Solvent
SDTA: Single Differential Thermal Analysis
SLP: ID for slurry experiment
SM: Starting material
TA: Thermal Analysis
TCP: ID for thermocycling and reflux experiment
Tf: triflate or trifluoromethanesulfonyl
TFA: Trifluoroacetic acid
TFE: 2,2,2-Trifluoroethanol
TGA: Thermogravimetric Analysis
TGA-MS/TG-MS: Thermogravimetric Analysis coupled with Mass Spectroscopy
THF: Tetrahydrofuran
TLC: Thin layer chromatography
VDL: ID for vapor diffusion into solutions experiment
VDS: ID for vapor diffusion onto solids experiment
XRPD: X-Ray Powder Diffraction 6.1 Analytical Methods XRPD patterns were obtained using the Crystallics T2 high-throughput XRPD set-up. The plates were mounted on a Bruker GADDS diffractometer equipped with a Hi-Star area detector. The XRPD platform was calibrated using Silver Behenate for the long d-spacings and Corundum for the short d-spacings. Data collection was carried out at room temperature using monochromatic $CuK_\alpha$ radiation in the $2\theta$ region between 1.5° and 41.5°, which is the most distinctive part of the XRPD pattern. The diffraction pattern of each well was collected in two $2\theta$ ranges ($1.5° \leq 2\theta \leq 21.5°$ for the first frame, and $19.5° \leq 2\theta \leq 41.5°$ for the second frame) with an exposure time of 90 s for each frame. No background subtraction or curve smoothing was applied to the XRPD patterns. The carrier material used during XRPD analysis was transparent to X-rays and contributed only slightly to the background.

DSC analyses were performed on a DSC822e instrument (Mettler-Toledo GmbH, Switzerland). The DSC822e was calibrated for temperature and enthalpy with a small piece of indium (m.p. is 156.6° C.; ΔHf is 28.45 J/g). Samples were sealed in standard 40 μl aluminum pans, pin-holed and heated in the DSC from 25° C. to 300° C., at a heating rate of 10° C./min. Dry $N_2$ gas, at a flow rate of 50 ml/min was used to purge the DSC equipment during measurement. The cycling DSC's were measured in standard 40 μl aluminum pans, pin-holed and heated in the DSC from 25° C. to 190° C., then cooled back to 25° C. The heating and cooling rate was 10° C./min. Dry $N_2$ gas, at a flow rate of 50 ml/min was used to purge the DSC equipment during measurement.

TGA/SDTA analysis was adopted to determine mass loss caused by solvent or water loss from crystals. Monitoring the sample weight, during heating in a TGA/SDTA851e instrument (Mettler-Toledo GmbH, Switzerland), results in a weight vs. temperature curve. The TGA/SDTA851e was calibrated for temperature with indium and aluminum. Samples were weighed into 100 μL aluminum crucibles and sealed. The seals were pin-holed and the crucibles heated in the TGA from 25° C. to 300° C. at a heating rate of 10° C./min. Dry $N_2$ gas was used for purging. The gases evolved from the TGA samples were analyzed by a mass spectrometer Omnistar GSD 301 T2 (Pfeiffer Vacuum GmbH, Germany). The latter is a quadrupole mass spectrometer, which analyses masses in the range of 0-200 amu.

Digital images were automatically collected for all the wells of each well-plate, employing a Philips PCVC 840K CCD camera controlled by Crystallics Photoslider software.

FTIR spectra were recorded on a ThermoFischer Scientific FT-IR: Nicolet 6700.

Morphology analysis of the samples was carried out on an Olympus microscope. Small amounts of samples were dispersed in mineral oil on a glass slide with cover slips and viewed with 20× or 50× magnification.

Hygroscopicity was determined on a Surface Measurement Systems DVS. Typically a sample size of 2-10 mg was loaded into the DVS instrument sample pan and the sample was analyzed on a DVS automated sorption analyzer at room temperature. The relative humidity was increased from 0% to 90% RH at 10% RH step then 95% RH. The relative humidity was then decreased in a similar manner to accomplish a full adsorption/desorption cycle. For selected hydrated forms, the analysis started at 50% RH and increased to 90% RH at 10% RH step. The relative humidity was then decreased in a similar manner to 0% RH followed by increasing to 50% RH.

High Performance Liquid Chromatography (HPLC) was performed according to the conditions in Table 1 and gradient program in Table 2.

TABLE 1

High Performance Liquid Chromatography (HPLC) experimental conditions

| | |
|---|---|
| Manufacturer | Agilent |
| HPLC | HP1200sl |
| UV-detector | HP DAD |
| MS-detector | HP1100 API-ES MSD VL-type |
| Column | Waters Sunfire C18 (100 × 4.6 mm; 3.5 μm) |
| Column Temperature | 35° C. |
| Mobile Phase A | 10 mM ammonium acetate |
| Mobile Phase B | Acetonitrile 100% |
| Flow Rate | 1.0 ml/min |
| Post time | 1 min |
| UV-Detector | DAD |
| Range | 200-400 nm |
| Wavelength | 254 nm |
| Slit width | 4 nm |
| Time | 0-12 min |
| MS-Detector | MSD |
| Scan | positive |
| Mass Range | 70-1000 amu |
| Fragmentator | 70 |
| Time | 0-12 min |
| Autosampler: | |
| Temperature | Not controlled |
| Injection mode | loop |
| Injection volume | 5 μL |
| Needle wash | 2/3; ACN/$H_2O$ (v/v) |
| Dilution solvent | 0.1% TFA water/acetonitrile (v/v = 50/50) |

TABLE 2

High Performance Liquid Chromatography (HPLC) experimental gradient program

| Time (mins) | % A | % B |
| --- | --- | --- |
| 0 | 90 | 10 |
| 1 | 90 | 10 |
| 6 | 10 | 90 |
| 9 | 10 | 90 |
| 10 | 90 | 10 |

The compound integrity is expressed as a peak-area percentage, calculated from the area of each peak in the chromatogram, except the 'injection peak', and the total peak-area, as follows:

$$\text{peak} - \text{area } \% = \frac{\text{peak} - \text{area}}{\text{total} - \text{area}} * 100\%$$

The peak-area percentage of the compound of interest is employed as an indication of the purity of the component in the sample.

Crystal16® multiple-reactor system (Avantium Technologies) holds 16 (4×4) standard HPLC glass vials (11.5 mm diameter, flat bottomed, 1.8 mL volume). A unit consists of four independently heated aluminum reactor blocks encased in a robust bench top setup. These blocks are electrically heated and cooled by a combination of Peltier elements and a cryostat. In order to prevent condensation of water on the reactor blocks and electronics during runs at temperatures below 10° C., the Crystal16® system provides an inlet for a dry purge gas (typically nitrogen). Operating Parameters are provided in Table 3.

TABLE 3

Operating Parameters of Crystal16 ® multiple-reactor system

| | |
| --- | --- |
| Temperature range | −15° C. to 150° C. |
| Heating/cooling | Individually programmable per reactor block |
| Temperature profile | Unlimited heating/cooling/hold steps per run programmable |
| Temperature control accuracy | 0.1° C. |
| Heating/cooling ramps | Programmable between 0° C. and 20° C./min |
| Stirrer speed (magnetic stirrer bars) | Programmable from 0-1250 rpm |
| Turbidity measurement | Per individual reactor in transmission |

6.2 Summary of Cocrystal Formation Screen

A total of 316 cocrystal formation experiments were divided over four different crystallization methods. Based on the chemical structure of Compound 1, 15 different coformers were selected (Table 5). The cocrystal formation experiments were performed as described in §6.3.

Physical stability of all samples was studied by exposing all solids to accelerated ageing conditions (40° C./75% RH for 48 hours) followed by re-analysis by XRPD and digital imaging. After exposure to accelerated ageing conditions, all solids were re-classified on the basis of their new XRPD patterns. The assignment of solid forms was primarily based on the XRPD analysis.

The cocrystals formed with Benzoic acid (Form 1), Fumaric acid (Form 2 and Form 3), Gentisic acid (Form 4 and Form 5), Nicotinamide (Form 6) and Succinic acid (Form 7) appear to be stable at accelerated aging conditions (40° C. and 75% RH). However, the cocrystals show a relatively high content of an impurity. The impurity was determined either by FT-IR or HPLC.

The cocrystal with maleic acid (Form 8) was stable after exposure to accelerated ageing conditions for (40° C./75% RH for 48 hours) and confirmed by TGMS, FTIR and HPLC analysis. Concluding remarks per analysis of these solids are given in Table 4.

TABLE 4

Summary table of the analytical experiments, results and conclusions of the cocrystals of Compound 1

| | Form 1 | Form 2 | Form 3 | Form 4 |
| --- | --- | --- | --- | --- |
| XRPD | Unique pattern | Unique pattern | Unique pattern | Unique pattern |
| TGMS | 5% mass loss (methanol) | 5.1% mass loss (water) | 4.2% mass loss (water & methanol) | 1.7% mass loss (water) |
| SDTA | Series of endothermic events ($T_{peak}$ is 89 & 259° C. decomposition) | Series of endothermic events ($T_{peak}$ is 115 & 177° C.) | Series of endothermic events ($T_{peak}$ is 93 & 178.1° C.) | Series of endothermic events ($T_{peak}$ is 101.3; 141.6; 169.4 & 199° C.) Exotermic event 173° C. |
| HPLC | Purity of Cmpd 1 (97.5%) Impurity RT = 4.54 min with 1.34% | Purity of Cmpd 1 (97.9%) Impurity RT = 4.54 min with 0.9% | Purity of Cmpd 1 (99.6%) | Purity of Cmpd 1 (100%) |
| FTIR | Changes in the spectrum as compared to that of the starting material 1800-1400 cm$^{-1}$ shifts tertiary amines, but also presence of the impurity determined by HPLC | Changes in the spectrum as compared to that of the starting material 1800-1400 cm$^{-1}$ shifts tertiary amines but also presence of the impurity determined by HPLC | Changes in the spectrum as compared to that of the starting material 1800-1400 cm$^{-1}$ shifts tertiary amines but also presence of the impurity determined by HPLC | Changes in the spectrum as compared to that of the starting material 1800-1400 cm$^{-1}$ shifts tertiary amines |

TABLE 4-continued

Summary table of the analytical experiments, results and conclusions of the cocrystals of Compound 1

| Conclusion | Cocrystal of Cmpd 1 with benzoic acid | Cocrystal of Cmpd 1 with fumaric acid, | Cocrystal of Cmpd 1 with fumaric acid | Cocrystal of Cmpd 1 with gentisic acid |
|---|---|---|---|---|
| | Form 5 | Form 6 | Form 7 | Form 8 |
| XRPD | Unique pattern | Unique pattern | Unique pattern | Unique pattern |
| TGMS | 1.6% mass loss (water) | 3.8% mass loss (THF & water) | 3.8% mass loss (water) | 4.6% mass loss (water) |
| SDTA | Series of endothermic events ($T_{peak}$ is 194 & 236° C.) | Series of endothermic events ($T_{peak}$ is 115.7 & 133.8° C.) | Series of endothermic events ($T_{peak}$ is 108.8; 163.4 & 260° C. decomposition) | Single melting point ($T_{peak}$ is 118.7° C.) |
| HPLC | Purity of Cmpd 1 (92%) | Purity of Cmpd 1 (100%) | Purity of Cmpd 1 (98.8%) Impurity RT = 4.54 min with 0.6% | Purity of Cmpd 1 (100%) |
| FTIR | Changes in the spectrum as compared to that of the starting material 1800-1400 $cm^{-1}$ shifts tertiary amines, but also presence of the impurity as determined by HPLC as well | Changes in the spectrum as compared to that of the starting material 1800-1400 $cm^{-1}$ shifts tertiary amines, but also presence of an impurity | Changes in the spectrum as compared to that of the starting material 1800-1400 $cm^{-1}$ shifts tertiary amines, but also presence of the impurity as determined by HPLC as well | Changes in the spectrum as compared to that of the starting material 1800-1600 $cm^{-1}$ shifts tertiary amines |
| Conclusion | Cocrystal of Cmpd 1 with gentisic acid | Cocrystal of Cmpd 1 with nicotinamide | Cocrystal of Cmpd 1 with succinic acid | Cocrystal of Cmpd 1 with maleic acid |

Form 1, a cocrystal solid form of Compound 1 with benzoic acid, is a methanol solvated form which desolvates at 89° C. and undergoes degradation starting with 200° C. Both HPLC and FT-IR indicated the presence of an impurity with retention time of 4.54 minutes. Nevertheless the FT-IR spectrum indicated that Compound 1 forms cocrystals with benzoic acid.

Form 2 and Form 3 are two cocrystal solid forms of Compound 1 with fumaric acid. Form 2 is a hydrate and Form 3 is a mixed hydrate/solvate with methanol. Apparently both Form 2 and Form 3 undergo desolvation and melt at a temperature around 177° C. The FT-IR spectra of Form 2 and Form 3 indicated that Compound 1 forms cocrystals with fumaric acid, although impurities were more visible in the Form 2 spectra. Nevertheless, the HPLC data of Form 2 indicates the existence of the impurity with retention time 4.54 minutes.

Form 4 and Form 5 are two cocrystal solid forms of Compound 1 with gentisic acid. FT-IR spectrum confirms cocrystallization for both Form 4 and Form 5. Nevertheless, Form 5 seems to contain impurity based on both HPLC and FT-IR analysis. On the other hand Form 4 is a chemically pure material, but SDTA signal of Form 4 shows that Form 4 may undergo through several solid state transformations during the SDTA analysis. Form 4 first desolvates and the process is followed by another series of endothermic events. Also the coformer alone was observed in the SDTA signal of Form 4.

Form 6 is a cocrystal formed by Compound 1 with nicotinamide and seems to be a mixed solvate/hydrate with THF. Form 6 first desolvates at a temperature around 115° C., followed by melt event at 134° C. and decomposition starting with 200° C. Although HPLC data shows a high sample purity, some traces of impurity were detected by FT-IR.

Form 7 is a cocrystal formed by Compound 1 with succinic acid which desolvates at 108° C. and melts at 163° C. Degradation of the cocrystal takes place at 200° C. and the melting event of the free base was observed at around 260° C. The FT-IR spectra confirms the co-crystallization of Compound 1 with succinic acid. Nevertheless, the impurity with a retention time of 4.54 minutes was also observed in samples.

Form 8 is a cocrystal formed by Compound 1 with maleic acid. The SDTA signal shows that Form 8 dehydrates and melts at around 120° C. followed by immediate decomposition. The FT-IT spectrum confirms the cocrystal formation of Compound 1 with maleic acid. Purity of Form 8 sample was assessed as 100% (area) by HPLC.

Almost all the investigated cocrystals (Form 1, Form 2, Form 3, Form 4, Form 5, Form 6 and Form 7) with the exception of Form 8 show multiple endothermic events by the SDTA signal suggesting their solvated/hydrated nature and also possible solid-state phase transformations that may take place at molecular level.

TGMS analysis of all the cocrystals (Form 1, Form 2, Form 3, Form 4, Form 5, Form 6, Form 7 and Form 8) reveal that these cocrystals are solvated and/or hydrated.

Form 8 has a melting point above 120° C. but significantly lower than Compound 1 free base and therefore it might be an indication of a higher solubility of this cocrystal over that of the free base.

HPLC analysis of Form 1, Form 2, Form 5 and Form 7 show the presence of an impurity with a retention time of 4.54 minutes.

The FT-IR spectra of Form 1, Form 2, Form 3, Form 4, Form 5, Form 6, Form 7 and Form 8 clearly show significant changes in the shifts at around 1800-1400 $cm^{-1}$ indicating the interaction of co-former molecules with the nitrogens of Compound 1.

On the basis of the results presented above, it is possible to make co-crystals of Compound 1 with both aliphatic and aromatic carboxylic acids (e.g., fumaric, maleic, succinic, benzoic and gentisic acid) as well as with amides (e.g., nicotinamides).

6.3 Experimental Methods

In total, 316 experiments were performed, including 124 cooling evaporative experiments, 64 slurry experiments, 64 powder in saturated solution experiments and 64 grinding experiments. In all methods, 4 solvents (see Table 6) and 15 coformers were tested (see Table 5), including 4 blank experiments per method. The coformers and the solvents used were the same for all four methods. The coformers have been selected on the basis of their H-bonding capability, diversity, pharmaceutical acceptability and solubility in the proposed solvents. An overview of the combination of methods and solvents used is provided in Table 5 and Table 6. The solvents used in the polymorph screen were either HPLC or reagent grade.

TABLE 5

Coformers used in the cocrystal screen

| # | Cocrystal former |
|---|---|
| 1 | N-methyl-D-Glucamine |
| 2 | Maleic acid |
| 3 | Glutamic acid, L- |
| 4 | Benzoic Acid |
| 5 | L(+)-Arginine |
| 6 | Nicotinamide |
| 7 | Fumaric acid |
| 8 | Tromethamine |
| 9 | Cinnamamide |
| 10 | Saccharin |
| 11 | L-Tyrosine |
| 12 | Dihydroxybenzoic acid, 2,5- |
| 13 | Choline chloride |
| 14 | Succinic acid |
| 15 | Lysine-,L |
| — | — |

TABLE 6

Solvents used in the cocrystal screen

| # | Solvents |
|---|---|
| 1 | Methanol |
| 2 | Tetrahydrofuran |
| 3 | Methanol/Water (50/50) |
| 4 | Tetrahydrofuran/Water (50/50) |

6.3.1 Cooling Evaporative Experiments

The cooling evaporative experiments employed 6 coformers, 4 solvents and two Compound 1:coformer ratios (see Table 8). Compound 1 free base (the starting material) and coformers were solid dosed in 1.8 mL experimental vials. A suitable volume of solvent was added to reach a close-to saturated solution. Following, the HPLC vials were capped and placed in the Crystal16® system to undergo the temperature profile as described in Table 7. Also 4 control experiments were performed. At the end of the temperature profile, the solids were separated from the liquids, dried and analyzed by XRPD and digital imaging. The mother liquids after separation of solids were evaporated and the remaining solids analyzed by XRPD and digital imaging too.

Subsequently, all solids were placed in a climate chamber at 40° C. and 75% RH for 48 hours and again analyzed by XRPD and digital imaging.

TABLE 7

Temperature profiles ($T_{profile}$) for the cocrystallization experiments

| $T_{start}$ (° C.) | Heating rate (° C./min) | $T_{max}$ (° C.) | Hold (minute) | Cooling rate (° C./h) | $T_{end}$ (° C.) | Age time (h) |
|---|---|---|---|---|---|---|
| 20 | 10 | 40 | 60 | 1 | 2 | 48 |

TABLE 8

Experimental conditions of the cocrystal cooling evaporation experiments

| Coformer (CI) | Solvent | Mass of starting material (mg) | Mass CI (mg) | Ratio (SM:CI) | Dissolved before $T_{profile}$ | Solids after $T_{profile}$ |
|---|---|---|---|---|---|---|
| Maleic acid | MeOH | 30.4 | 11.60 | 1:1.1 | No | Yes |
| | THF | 30.7 | 11.80 | | No | Yes |
| | MeOH/Water (50/50) | 29.8 | 12.10 | | No | Yes |
| | THF/Water (50/50) | 30.1 | 11.70 | | No | Yes |
| | MeOH | 30.5 | 41.60 | 1:4 | No | Yes |
| | THF | 29.5 | 41.30 | | No | Yes |
| | MeOH/Water (50/50) | 30.0 | 42.10 | | No | Yes |
| | THF/Water (50/50) | 30.2 | 41.40 | | No | No |
| Benzoic Acid | MeOH | 30.1 | 12.60 | 1:1.1 | No | Yes |
| | THF | 30.5 | 11.90 | | No | Yes |
| | MeOH/Water (50/50) | 31.6 | 12.00 | | No | Yes |
| | THF/Water (50/50) | 30.4 | 12.90 | | No | Yes |
| | MeOH | 30.3 | 44.40 | 1:4 | No | Yes |
| | THF | 29.8 | 44.50 | | No | Yes |
| | MeOH/Water (50/50) | 30.0 | 43.80 | | No | Yes |
| | THF/Water (50/50) | 30.0 | 44.50 | | No | Yes |

TABLE 8-continued

Experimental conditions of the cocrystal cooling evaporation experiments

| Coformer (CI) | Solvent | Mass of starting material (mg) | Mass CI (mg) | Ratio (SM:CI) | Dissolved before $T_{profile}$ | Solids after $T_{profile}$ |
|---|---|---|---|---|---|---|
| Nicotinamide | MeOH | 29.8 | 12.70 | 1:1.1 | No | Yes |
|  | THF | 30.8 | 11.90 |  | No | Yes |
|  | MeOH/Water (50/50) | 31.1 | 12.50 |  | No | Yes |
|  | THF/Water (50/50) | 29.7 | 12.50 |  | No | Yes |
|  | MeOH | 30.0 | 44.70 | 1:4 | No | Yes |
|  | THF | 30.3 | 44.70 |  | No | Yes |
|  | MeOH/Water (50/50) | 30.5 | 46.20 |  | No | Yes |
|  | THF/Water (50/50) | 29.8 | 44.10 |  | No | Yes |
| Fumaric acid | MeOH | 30.0 | 11.90 | 1:1.1 | No | Yes |
|  | THF | 30.2 | 13.80 |  | No | Yes |
|  | MeOH/Water (50/50) | 29.8 | 12.00 |  | No | Yes |
|  | THF/Water (50/50) | 29.9 | 11.70 |  | No | Yes |
|  | MeOH | 29.6 | 42.40 | 1:4 | No | Yes |
|  | THF | 29.6 | 41.80 |  | No | Yes |
|  | MeOH/Water (50/50) | 30.2 | 41.90 |  | No | Yes |
|  | THF/Water (50/50) | 30.2 | 42.10 |  | No | Yes |
| Gentisic acid (Dihydroxy benzoic acid, 2,5-) | MeOH | 30.9 | 15.40 | 1:1.1 | No | Yes |
|  | THF | 29.8 | 15.90 |  | No | Yes |
|  | MeOH/Water (50/50) | 29.6 | 15.50 |  | No | Yes |
|  | THF/Water (50/50) | 29.7 | 15.50 |  | No | Yes |
|  | MeOH | 29.6 | 55.30 | 1:4 | No | Yes |
|  | THF | 30.1 | 55.30 |  | No | Yes |
|  | MeOH/Water (50/50) | 30.6 | 56.30 |  | No | Yes |
|  | THF/Water (50/50) | 30.3 | 55.00 |  | No | Yes |
| Succinic acid | MeOH | 29.8 | 12.00 | 1:1.1 | No | Yes |
|  | THF | 30.7 | 11.70 |  | No | Yes |
|  | MeOH/Water (50/50) | 30.4 | 11.80 |  | No | Yes |
|  | THF/Water (50/50) | 29.8 | 12.00 |  | No | Yes |
|  | MeOH | 29.8 | 42.40 | 1:4 | No | Yes |
|  | THF | 30.7 | 43.00 |  | No | Yes |
|  | MeOH/Water (50/50) | 29.7 | 43.20 |  | No | Yes |
|  | THF/Water (50/50) | 30.1 | 42.60 |  | No | Yes |
| none | MeOH | 30.0 | — | — | No | Yes |
|  | THF | 30.1 | — |  | No | Yes |
|  | MeOH/Water (50/50) | 30.2 | — |  | No | Yes |
|  | THF/Water (50/50) | 29.9 | — |  | No | Yes |

Volume of solvent is 1000 μL.

6.3.2 Powder in Saturated Solutions Experiments

In these experiments 6 coformers and 4 solvents were tested (see Table 9). In each solvent, saturated solutions of Compound 1 were prepared. To the saturated solutions the solid coformers were added until the coformer did not dissolve anymore or precipitation occurred. The samples remained for 4 hours at ambient temperature, while stirring.

In addition, 6 control experiments were performed. Subsequently, the solids were separated from the liquids. The solids were dried and mother liquors evaporated under vacuum. All obtained solids were then analyzed by XRPD and digital imaging.

The solids were placed in a climate chamber at 40° C. and 75% RH for 48 hr after which they were analyzed by XRPD and digital imaging.

TABLE 9

Experimental conditions for the "powder in saturated solutions" experiments

| Coformer (CI) | Solvent | Mass of Cmpd 1 (mg) | Mass of Coformer (mg) | Molar Ratio (Cmpd 1:Co-former) | Dissolved before $T_{profile}$ | Solids after $T_{profile}$ |
|---|---|---|---|---|---|---|
| Maleic acid | THF | 20.0 | 34.90 | 1:5 | No | Yes |
|  | MeOH/Water (50/50) | 20.0 | 34.90 | 1:5 | No | No |
|  | THF/Water (50/50) | 20.0 | 34.90 | 1:5 | No | No |
|  | MeOH | 20.0 | 34.90 | 1:5 | No | Yes |
| Benzoic Acid | THF | 20.0 | 36.70 | 1:5 | No | No |
|  | MeOH/Water (50/50) | 20.0 | 36.70 | 1:5 | No | Yes |
|  | THF/Water (50/50) | 20.0 | 36.70 | 1:5 | No | No |
|  | MeOH | 20.0 | 36.70 | 1:5 | No | Yes |
| Nicotinamide | THF | 20.0 | 36.30 | 1:5 | No | Yes |
|  | MeOH/Water (50/50) | 20.0 | 36.30 | 1:5 | No | No |
|  | THF/Water (50/50) | 20.0 | 36.30 | 1:5 | No | Yes |
|  | MeOH | 20.0 | 36.30 | 1:5 | No | Yes |

TABLE 9-continued

Experimental conditions for the "powder in saturated solutions" experiments

| Coformer (CI) | Solvent | Mass of Cmpd 1 (mg) | Mass of Coformer (mg) | Molar Ratio (Cmpd 1:Coformer) | Dissolved before $T_{profile}$ | Solids after $T_{profile}$ |
|---|---|---|---|---|---|---|
| Fumaric acid | THF | 20.0 | 34.90 | 1:5 | No | Yes |
|  | MeOH/Water (50/50) | 20.0 | 34.90 | 1:5 | No | Yes |
|  | THF/Water (50/50) | 20.0 | 34.90 | 1:5 | No | Yes |
|  | MeOH | 20.0 | 34.90 | 1:5 | No | Yes |
| Gentisic acid (Dihydroxy benzoic acid, 2,5-) | THF | 20.0 | 46.30 | 1:5 | No | Yes |
|  | MeOH/Water (50/50) | 20.0 | 46.30 | 1:5 | No | Yes |
|  | THF/Water (50/50) | 20.0 | 46.30 | 1:5 | No | Yes |
|  | MeOH | 20.0 | 46.30 | 1:5 | No | No |
| Succinic acid | THF | 20.0 | 35.50 | 1:5 | No | Yes |
|  | MeOH/Water (50/50) | 20.0 | 35.50 | 1:5 | No | No |
|  | THF/Water (50/50) | 20.0 | 35.50 | 1:5 | No | Yes |
|  | MeOH | 20.0 | 35.50 | 1:5 | No | Yes |
| none | THF | 20.0 | — | 1:5 | No | No |
|  | MeOH/Water (50/50) | 20.0 | — | 1:5 | No | No |
|  | THF/Water (50/50) | 20.0 | — | 1:5 | No | No |
|  | MeOH | 20.0 | — | 1:5 | No | Yes |

Volume of solvent is 1000 µL.

6.3.3 Slurry Experiments

Compound 1 free base was solid dosed in 1.8 mL scale experimental vials. The coformer was added with a ratio of 1:1.1 (Compound 1:coformer). The solvent and a stirring bar were added to the vials. The experiments used 6 coformers and 4 solvents (see Table 10) and 4 control experiments without coformer were also performed. Then the vials were capped and stirred at ambient conditions for 3 days. After the solids were separated from the liquids, the solids were analyzed wet by XRPD and digital imaging. Then both the solids and mother liquors were dried and evaporated under vacuum at ambient temperature (10 mbar for 24 hours). The solids obtained were then analyzed by XRPD and digital imaging. Subsequently, the solids were incubated in a climate chamber at 40° C. and 75% RH for 48 hours and again analyzed by XRPD and digital imaging.

TABLE 10

Experimental conditions of the cocrystal slurry experiments

| Coformer (CI) | Solvent | Mass of Cmpd 1 (mg) | Mass CI (mg) | Molar Ratio (Cmpd 1:Coformer) | Dissolved before $T_{profile}$ | Solids after $T_{profile}$ |
|---|---|---|---|---|---|---|
| Maleic acid | MeOH | 30.3 | 12.00 | 1:1.1 | No | Yes |
|  | THF | 30.3 | 11.40 | 1:1.1 | No | Yes |
|  | MeOH/Water (50/50) | 29.9 | 11.60 | 1:1.1 | No | Yes |
|  | THF/Water (50/50) | 30.6 | 11.90 | 1:1.1 | No | Yes |
| Benzoic Acid | MeOH | 30.2 | 12.00 | 1:1.1 | No | Yes |
|  | THF | 30.1 | 12.60 | 1:1.1 | No | Yes |
|  | MeOH/Water (50/50) | 30.4 | 13.00 | 1:1.1 | No | Yes |
|  | THF/Water (50/50) | 30.1 | 13.40 | 1:1.1 | No | Yes |
| Nicotinamide | MeOH | 30.1 | 12.40 | 1:1.1 | No | Yes |
|  | THF | 30.0 | 12.40 | 1:1.1 | No | Yes |
|  | MeOH/Water (50/50) | 30.4 | 12.30 | 1:1.1 | No | Yes |
|  | THF/Water (50/50) | 29.8 | 12.70 | 1:1.1 | No | Yes |
| Fumaric acid | MeOH | 30.7 | 12.00 | 1:1.1 | No | Yes |
|  | THF | 29.7 | 12.30 | 1:1.1 | No | Yes |
|  | MeOH/Water (50/50) | 29.6 | 12.10 | 1:1.1 | No | Yes |
|  | THF/Water (50/50) | 30.9 | 11.90 | 1:1.1 | No | Yes |
| Gentisic acid (Dihydroxy benzoic acid, 2,5-) | MeOH | 29.9 | 15.70 | 1:1.1 | No | Yes |
|  | THF | 30.7 | 15.80 | 1:1.1 | No | Yes |
|  | MeOH/Water (50/50) | 30.4 | 16.00 | 1:1.1 | No | Yes |
|  | THF/Water (50/50) | 30.1 | 16.10 | 1:1.1 | No | Yes |
| Succinic acid | MeOH | 30.5 | 11.60 | 1:1.1 | No | Yes |
|  | THF | 29.8 | 11.70 | 1:1.1 | No | Yes |
|  | MeOH/Water (50/50) | 30.1 | 12.80 | 1:1.1 | No | Yes |
|  | THF/Water (50/50) | 29.8 | 12.20 | 1:1.1 | No | Yes |
| none | MeOH | 30.5 | 0.10 | 1:1.1 | No | Yes |
|  | THF | 29.7 | 0.10 | 1:1.1 | No | Yes |
|  | MeOH/Water (50/50) | 30.2 | 0.10 | 1:1.1 | No | Yes |
|  | THF/Water (50/50) | 30.6 | 0.10 | 1:1.1 | No | Yes |

Volume of solvent is 500 µL.

6.3.4 Grinding Experiments 64 single-solvent-drop grinding experiments were performed using 6 coformers and 4 solvents. Moreover 4 control experiments were performed. Compound 1 free base was weighed into metal grinding vials, containing two stainless steel grinding balls. The coformers and solvents were added (see Table 11). The molar ratio of compound 1 free base and the coformer is 1:1.1. The experiments were shaken for 1 hour at a frequency of 30 Hz. After the 1-hour shaking, the samples were analyzed by XRPD and digital imaging. Subsequently the samples were exposed to accelerated aging conditions (40° C., 75% RH) for 48 hr and re-analyzed by XRPD and digital imaging.

TABLE 11

Conditions of grinding experiments

| Coformer | Solvent | Mass of Cmpd 1 (mg) | Mass of Coformer (mg) | Solids after $T_{profile}$ |
|---|---|---|---|---|
| Maleic acid | MeOH | 29.9 | 12.30 | Yes |
| | THF | 30.1 | 11.70 | Yes |
| | MeOH/Water (50/50) | 30.1 | 11.60 | Yes |
| | THF/Water (50/50) | 29.8 | 11.80 | Yes |
| Benzoic Acid | MeOH | 29.8 | 12.90 | Yes |
| | THF | 29.6 | 12.50 | Yes |
| | MeOH/Water (50/50) | 30.1 | 12.70 | Yes |
| | THF/Water (50/50) | 29.9 | 12.40 | Yes |
| Nicotinamide | MeOH | 30.3 | 12.90 | Yes |
| | THF | 30.0 | 12.20 | Yes |
| | MeOH/Water (50/50) | 30.1 | 12.80 | Yes |
| | THF/Water (50/50) | 29.9 | 12.60 | Yes |
| Fumaric acid | MeOH | 30.3 | 11.90 | Yes |
| | THF | 29.9 | 12.10 | Yes |
| | MeOH/Water (50/50) | 29.9 | 12.00 | Yes |
| | THF/Water (50/50) | 30.2 | 11.90 | Yes |
| Gentisic acid (Dihydroxy benzoic acid, 2,5-) | MeOH | 29.6 | 15.40 | Yes |
| | THF | 29.8 | 15.40 | Yes |
| | MeOH/Water (50/50) | 29.7 | 15.30 | Yes |
| | THF/Water (50/50) | 29.9 | 15.40 | Yes |
| Succinic acid | MeOH | 30.8 | 11.70 | Yes |
| | THF | 29.7 | 11.90 | Yes |
| | MeOH/Water (50/50) | 29.6 | 12.00 | Yes |
| | THF/Water (50/50) | 30.0 | 11.30 | Yes |
| none | MeOH | 30.3 | 0.10 | Yes |
| | THF | 30.0 | 0.10 | Yes |
| | MeOH/Water (50/50) | 30.0 | 0.10 | Yes |
| | THF/Water (50/50) | 31.1 | 0.10 | Yes |

Volume of solvent is 10 µL.

6.3.5 Cocrystal Solid Form 1

Form 1 was prepared in grinding experiments when benzoic acid was used as coformer and the mixture of methanol and water (50/50) was used as solvent. Form 1 is a methanol solvated cocrystal form of Compound 1 and benzoic acid.

FIG. 1 provides an overlay of XRPD patterns (from bottom to top) of: Compound 1, Form 1 and benzoic acid. A list of X-Ray Diffraction Peaks for Form 1 is provided below in Table 12.

TABLE 12

X-Ray Diffraction Peaks for Form 1

| Two-theta angle (°) | d Space (Å) | Relative Intensity (%) |
|---|---|---|
| 7.78 | 11.35 | 82.06 |
| 13.02 | 6.79 | 54.62 |
| 13.54 | 6.53 | 23.54 |
| 20.62 | 4.3 | 10.7 |
| 24.26 | 3.66 | 21.5 |
| 25.02 | 3.55 | 45.6 |
| 26.1 | 3.41 | 27.99 |

FIG. 2 and FIG. 3 provide TGMS data and TGA/SDTA data of Form 1, respectively. A mass loss of 5% corresponding to methanol was observed during an endothermic event with $T_{peak}$ 89° C. suggesting the solvated nature of the sample. According to the SDTA signal in FIG. 3, degradation already starts at 200° C.

Figure 4:
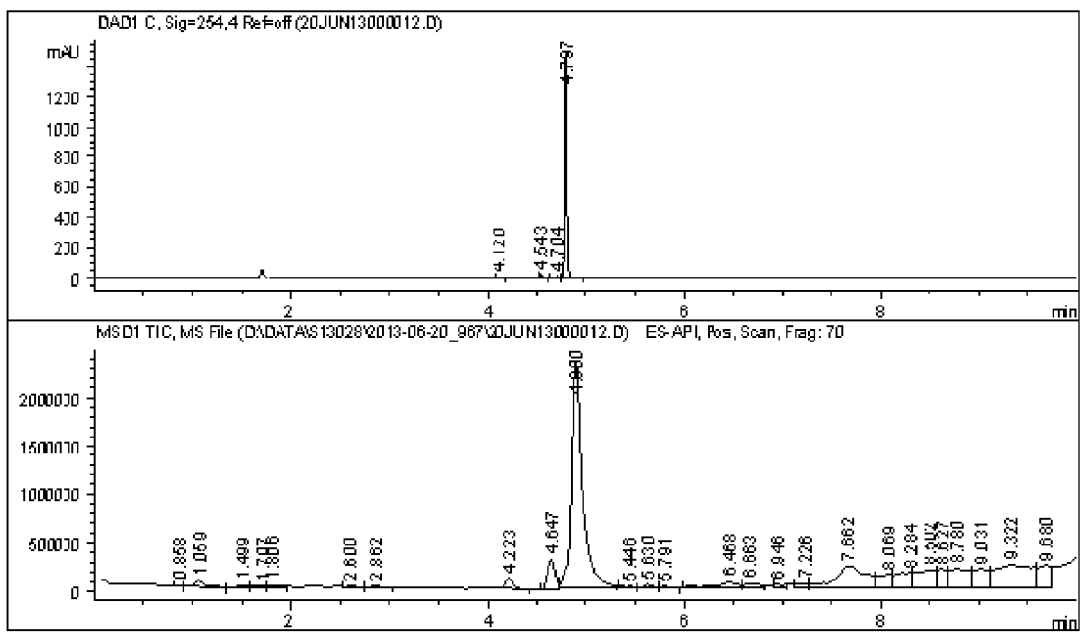
FIG. 4 depicts high performance liquid chromatography coupled with mass spectrometry of Form 1.

FIG. 4 provides HPLC and MS data of Form 1. The peak retention time is 4.8 minutes. HPLC data indicates that the sample purity is 97.5% (area %).

Figure 5:
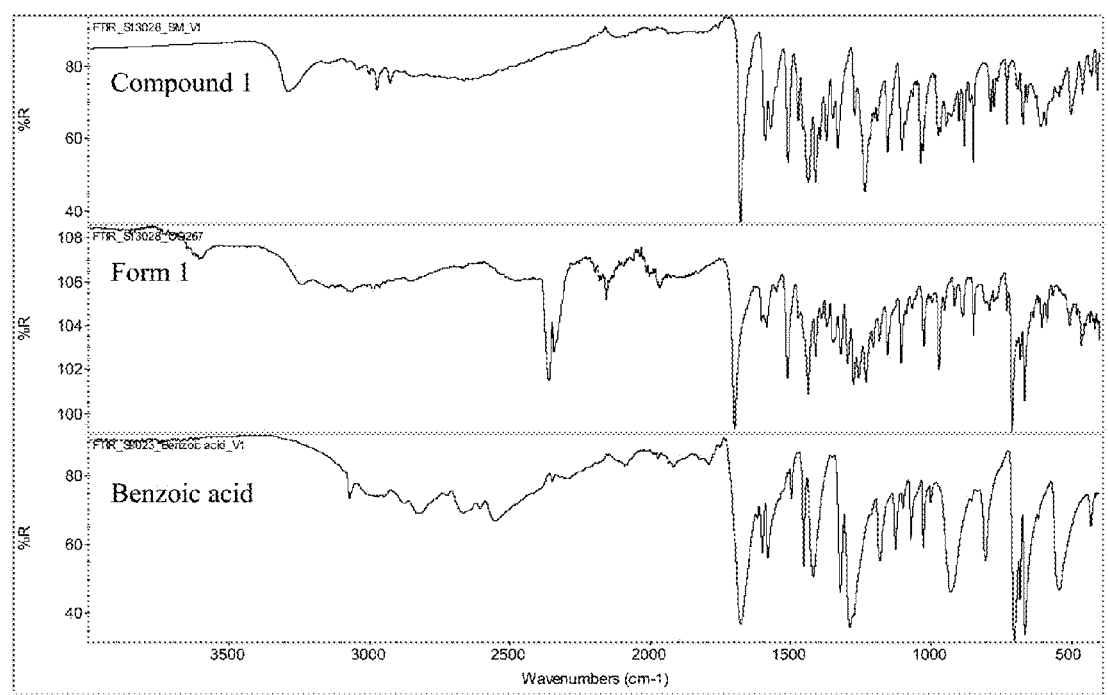
FIG. 5 depicts a fourier transform infrared spectroscopy (FTIR) overlay of Compound 1, Form 1 and benzoic acid.

FIG. 5 provides an FTIR overlay of the starting material Compound 1 (blue), Form 1 (red) and benzoic acid (green). The overlay indicates that the main shifts take place in the spectra in the region 1800-1500 cm$^{-1}$ and 1600-1400 cm$^{-1}$.

Figure 6:
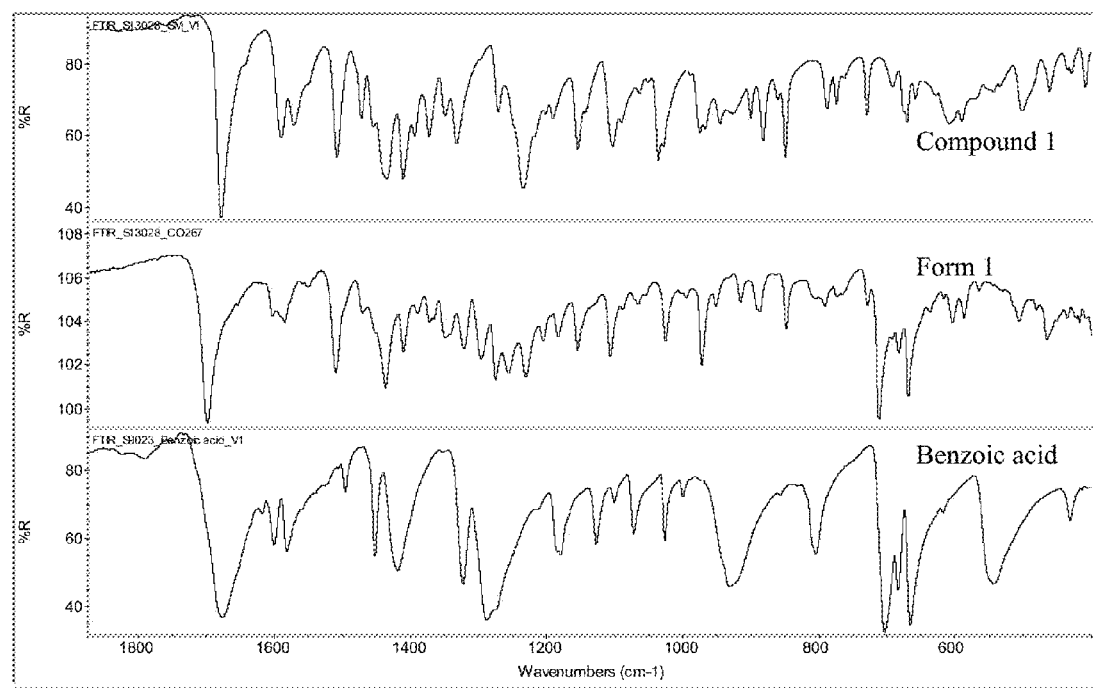
FIG. 6 depicts a FTIR overlay of Compound 1, Form 1 and benzoic acid in the region of 1800-400 $cm^{-1}$.

FIG. 6 provides an FTIR overlay of the starting material Compound 1 (blue), Form 1 (red) and benzoic acid (green) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.3.6 Cocrystal Solid Form 2

Form 2 was prepared in grinding experiments when fumaric acid was used as coformer and the mixture of methanol and water (50/50) was used as solvent. Form 2 is a hydrated cocrystal form of Compound 1 and fumaric acid.

FIG. 7 provides an overlay of XRPD patterns (from bottom to top) of: Compound 1, Form 2, Form 3 and Fumaric acid. A list of X-Ray Diffraction Peaks for Form 2 of Compound 1 is provided below in Table 13.

TABLE 13

X-Ray Diffraction Peaks for Form 2

| Two-theta angle (°) | d Space (Å) | Relative Intensity (%) |
|---|---|---|
| 7.66 | 11.53 | 77.32 |
| 10.42 | 8.48 | 37.33 |
| 14.02 | 6.31 | 23.27 |
| 17.46 | 5.07 | 16.56 |
| 18.38 | 4.82 | 14.78 |
| 19.3 | 4.59 | 16.49 |
| 24.06 | 3.69 | 27.03 |
| 27.02 | 3.3 | 85.2 |

FIG. 8 and FIG. 9 provide TGMS data and TGA/SDTA data of Form 2. A mass loss of 5.1% between about 35° C. and about 135° C. corresponding to water was observed during an endothermic event with $T_{peak}$ 115° C. suggesting the solvated nature of the sample. According to the SDTA signal in FIG. 9, an endothermic melt event was observed at 177° C., followed by immediate decomposition.

Figure 10:
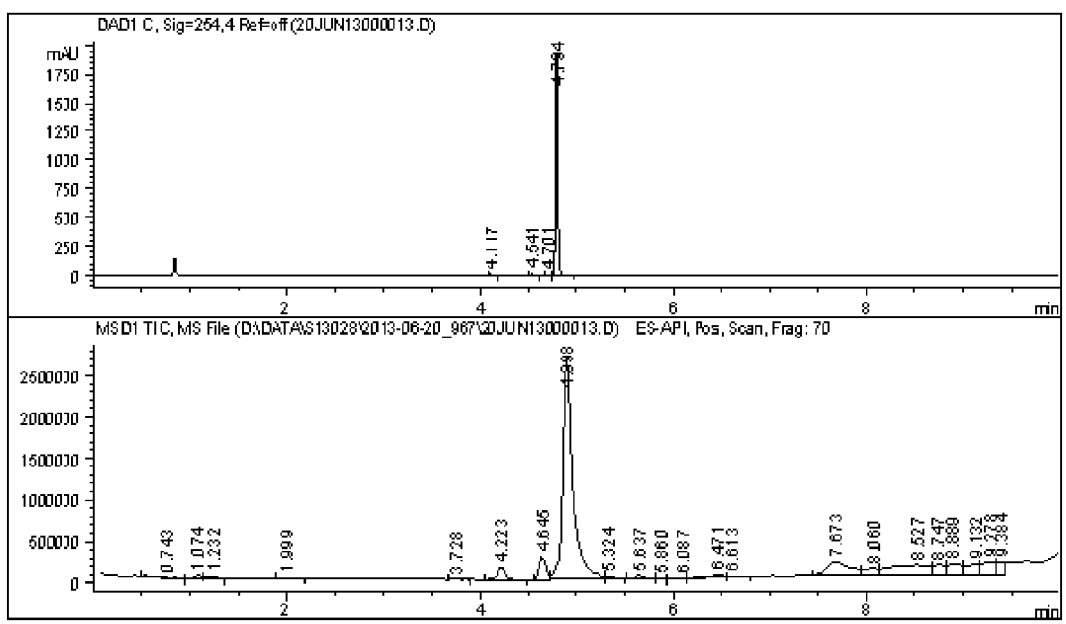
FIG. 10 depicts high performance liquid chromatography coupled with mass spectrometry of Form 2.

FIG. 10 provides HPLC and MS data of Form 2. The peak retention time is 4.8 minutes. The HPLC data indicates that the sample purity is 98.0% (area %).

Figure 11:
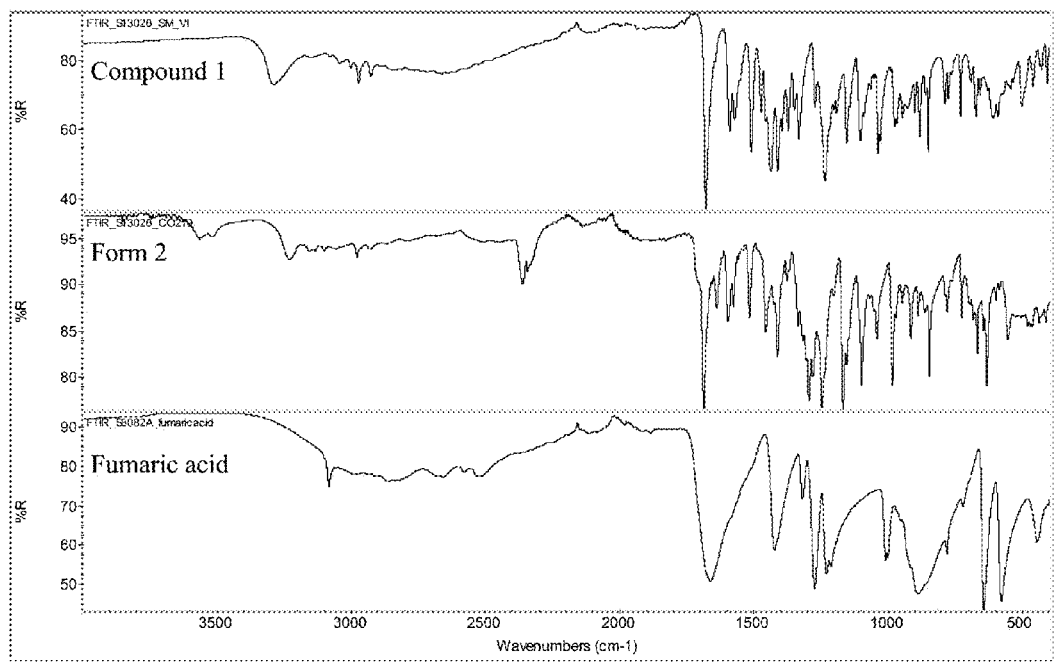
FIG. 11 depicts a FTIR overlay of Compound 1, Form 2 and benzoic acid.

FIG. 11 provides an FTIR overlay of the starting material Compound 1 (blue), Form 2 (red) and fumaric acid (green). The overlay indicates that the main shifts take place in the spectra in the region 1800-1500 cm$^{-1}$ and 1600-1400 cm$^{-1}$.

Figure 12:
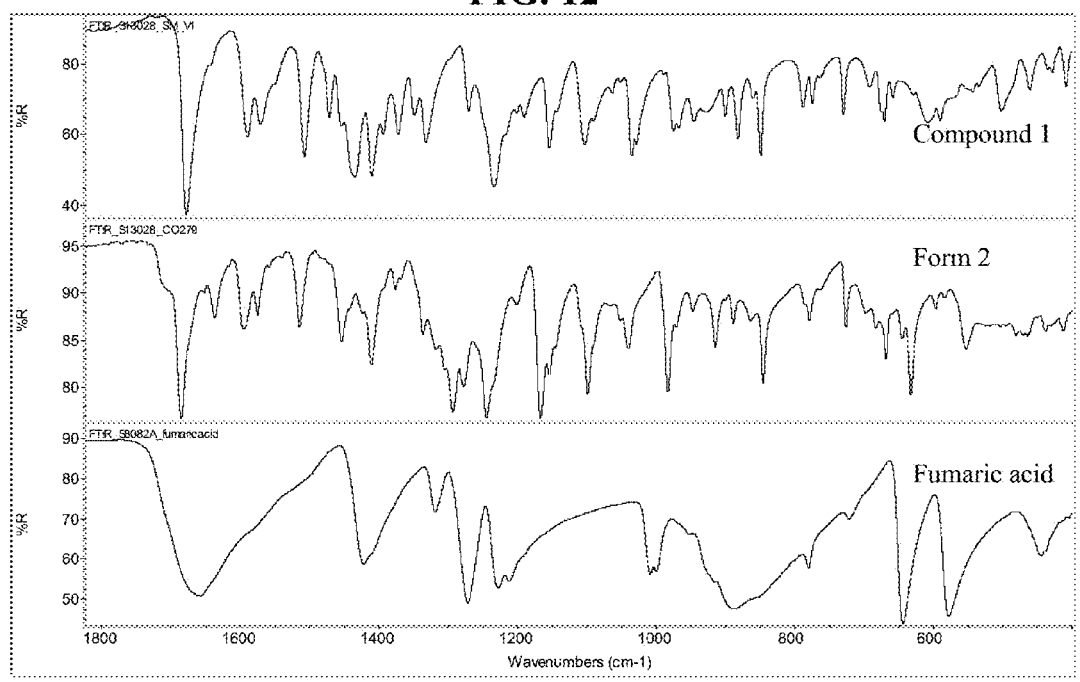
FIG. 12 depicts a FTIR overlay of Compound 1, Form 2 and benzoic acid in the region of 1800-400 $cm^{-1}$.

FIG. 12 provides an FTIR overlay of the starting material Compound 1 (blue), Form 2 (red) and fumaric acid (green) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.3.7 Cocrystal Solid Form 3

Form 3 was prepared in cooling evaporative experiments when fumaric acid was used as coformer and methanol was used as solvent. Form 3 is a methanol and water solvated cocrystal form of Compound 1 and fumaric acid.

FIG. 7 provides an overlay of XRPD patterns (from bottom to top) of: Compound 1, Form 2, Form 3 and Fumaric acid. A list of X-Ray Diffraction Peaks for Form 3 of Compound 1 is provided below in Table 14.

TABLE 14

X-Ray Diffraction Peaks for Form 3

| Two-theta angle (°) | d Space (Å) | Relative Intensity (%) |
| --- | --- | --- |
| 9.06 | 9.75 | 79.55 |
| 13.66 | 6.47 | 14.11 |
| 17.14 | 5.17 | 12.91 |
| 22.74 | 3.91 | 27.27 |
| 24.58 | 3.62 | 25.39 |
| 26.06 | 3.42 | 44.2 |
| 26.9 | 3.31 | 29.59 |
| 28.7 | 3.11 | 38.87 |

FIG. 13 and FIG. 14 provide TGMS data and TGA/SDTA data of Form 3. A mass loss of 4.2% between about 35° C. and about 105° C. corresponding to water and methanol was observed during an endothermic event with $T_{peak}$ 93° C. suggesting the solvated nature of the sample. According to the SDTA signal in FIG. 14, an endothermic melt event was observed at 178.1° C., followed by immediate decomposition.

Figure 15:
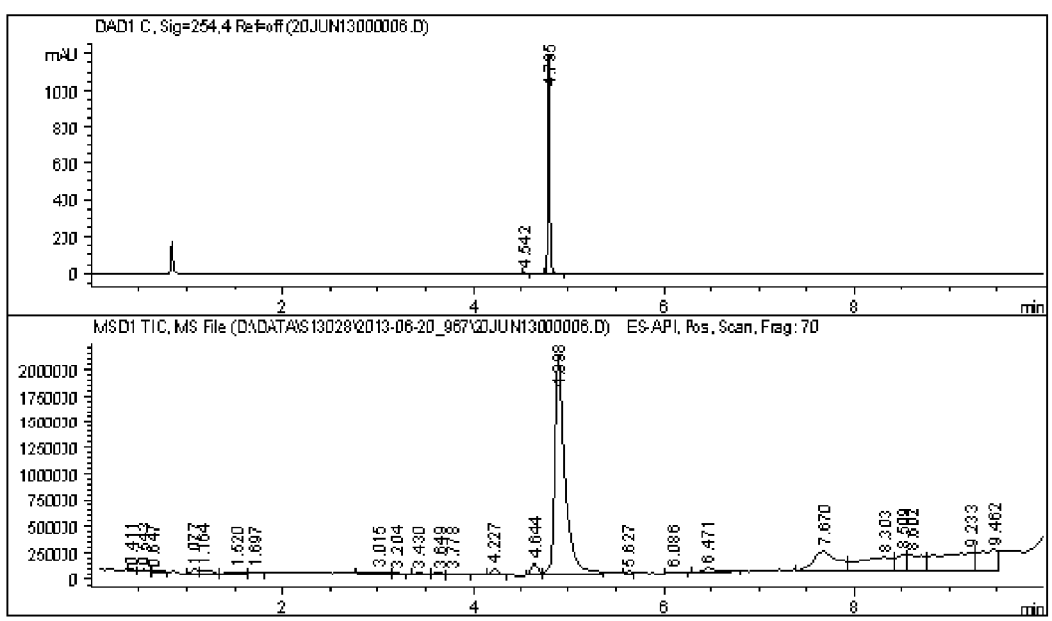
FIG. 15 depicts high performance liquid chromatography coupled with mass spectrometry of Form 3.

FIG. 15 provides HPLC and MS data of Form 3. The peak retention time is 4.8 minutes. The HPLC data indicates that the sample purity is 100.0% (area %).

Figure 16:
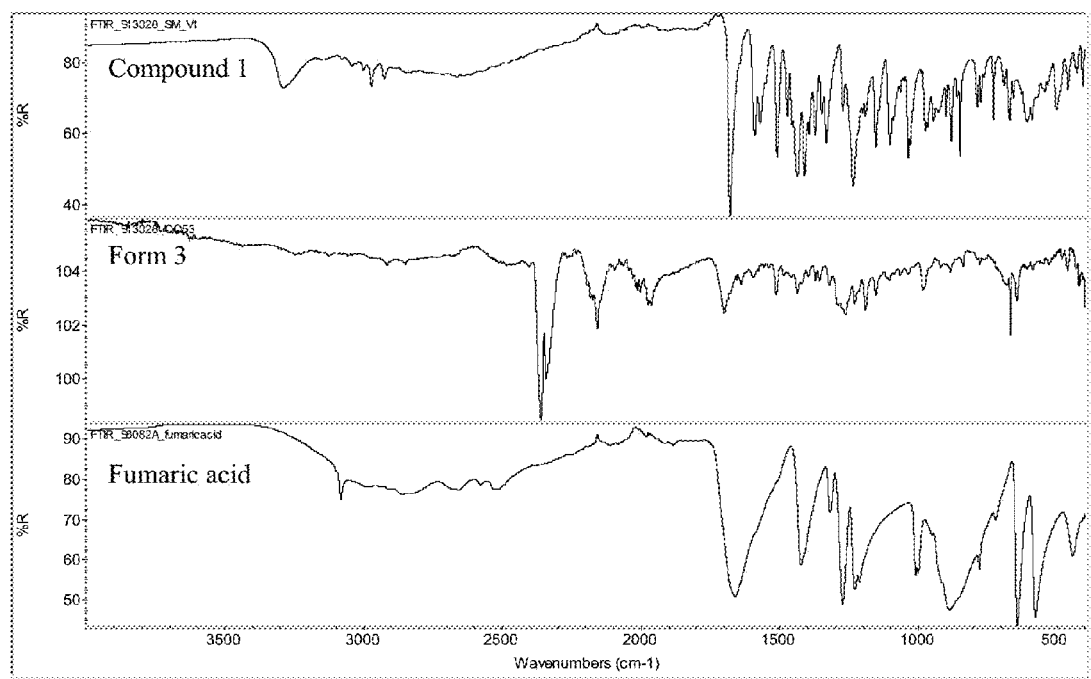
FIG. 16 depicts a FTIR overlay of Compound 1, Form 3 and benzoic acid.

FIG. 16 provides an FTIR overlay of the starting material Compound 1 (blue), Form 3 (red) and fumaric acid (green). The overlay indicates that the main shifts take place in the spectra in the region 1800-1500 cm$^{-1}$ and 1600-1400 cm$^{-1}$.

Figure 17:
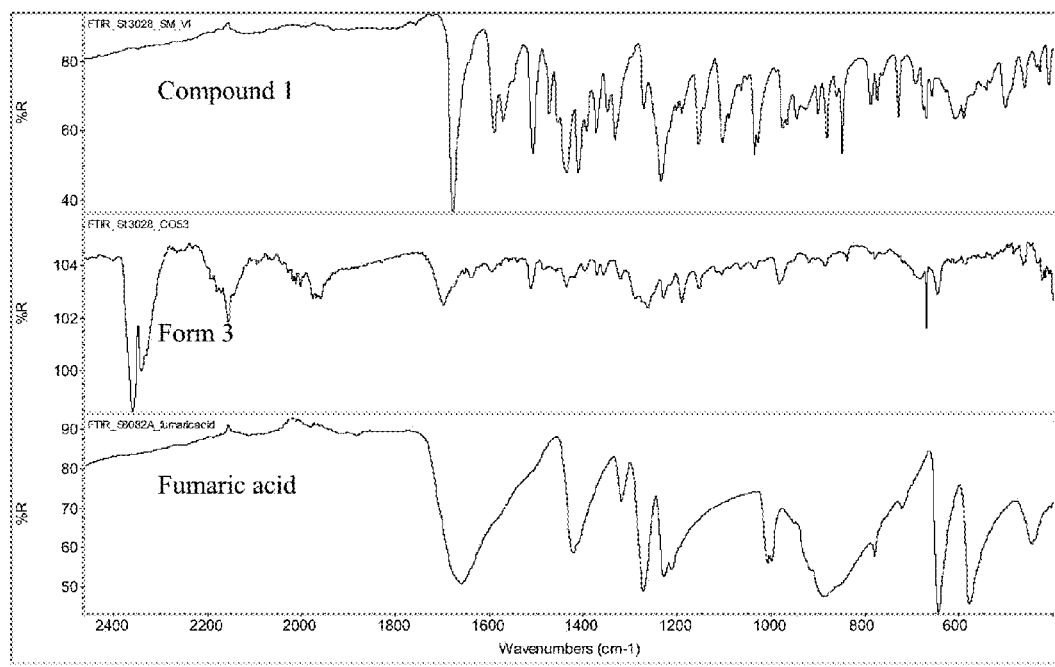
FIG. 17 depicts a FTIR overlay of Compound 1, Form 3 and benzoic acid in the region of 1800-400 $cm^{-1}$.

FIG. 17 provides an FTIR overlay of the starting material Compound 1 (blue), Form 3 (red) and fumaric acid (green) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.3.8 Cocrystal Solid Form 4

Form 4 was prepared in cooling evaporative experiments when gentisic acid was used as coformer and the mixture of methanol and water (50/50) was used as solvent. Form 4 is a hydrated cocrystal form of Compound 1 and gentisic acid.

FIG. 18 provides an overlay of XRPD patterns of: Compound 1, Form 4, Form 5 and gentisic acid (from bottom to top). A list of X-Ray Diffraction Peaks for Form 4 of Compound 1 is provided below in Table 15.

TABLE 15

X-Ray Diffraction Peaks for Form 4

| Two-theta angle (°) | d Space (Å) | Relative Intensity (%) |
| --- | --- | --- |
| 6.62 | 13.34 | 14.26 |
| 7.58 | 11.65 | 30.02 |
| 8.9 | 9.92 | 8.57 |
| 9.42 | 9.38 | 9.56 |
| 12.22 | 7.23 | 45.27 |
| 12.82 | 6.9 | 24.53 |
| 13.34 | 6.63 | 71.66 |
| 13.9 | 6.36 | 13.45 |
| 14.34 | 6.17 | 10.11 |
| 16.14 | 5.49 | 14.05 |
| 18.94 | 4.68 | 12.58 |
| 20.46 | 4.34 | 7.7 |
| 22.34 | 3.97 | 24.96 |
| 22.9 | 3.88 | 53.61 |
| 23.66 | 3.76 | 24.65 |
| 24.22 | 3.67 | 28.84 |
| 25.18 | 3.53 | 73.43 |
| 26.62 | 3.34 | 19.81 |
| 27.46 | 3.24 | 23.79 |
| 33.02 | 2.71 | 20.57 |

FIG. 19 and FIG. 20 provide TGMS data and TGA/SDTA data of Form 4. A mass loss of 1.7% between approximately 110° C. and approximately 150° C. corresponding to water was observed during an endothermic event with $T_{peak}$ 101.3 and 141.6° C., suggesting the solvated nature of the sample, followed by another endothermic event with $T_{peak}$ 169.4° C. An exothermic event with $T_{peak}$ 175° C. suggests re-crystallization to another form. According to the SDTA signal in FIG. 20, an endothermic melt event was observed at 199° C., followed by immediate decomposition.

Figure 21:
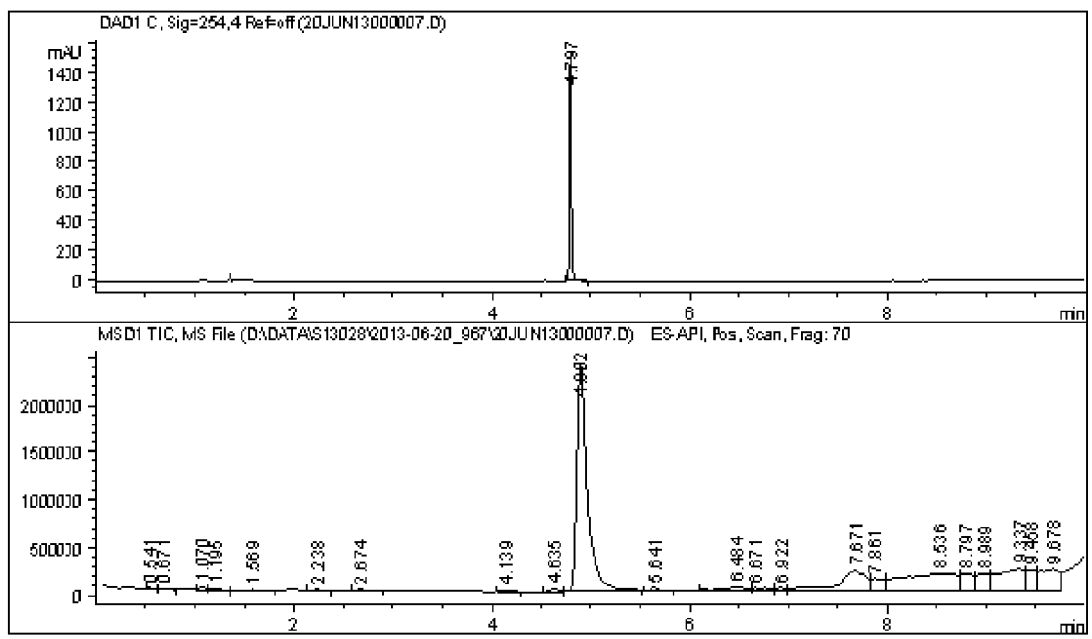
FIG. 21 depicts high performance liquid chromatography coupled with mass spectrometry of Form 4.

FIG. 21 provides HPLC and MS data of Form 4. The peak retention time is 4.8 minutes. The HPLC data indicates that the sample purity is 100.0% (area %).

Figure 22:
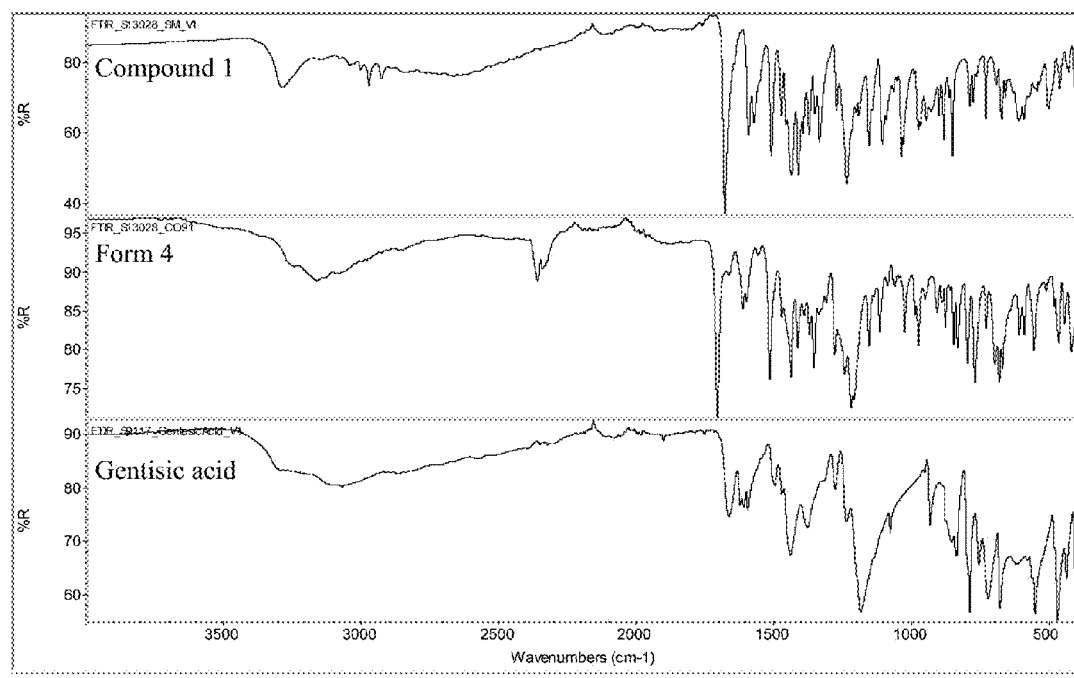
FIG. 22 depicts a FTIR overlay of Compound 1, Form 4 and gentisic acid.

FIG. 22 provides an FTIR overlay of the starting material Compound 1 (blue), Form 4 (red) and gentisic acid (green). The overlay indicates that the main shifts take place in the spectra in the region 1800-1500 cm$^{-1}$ and 1600-1400 cm$^{-1}$.

Figure 23:
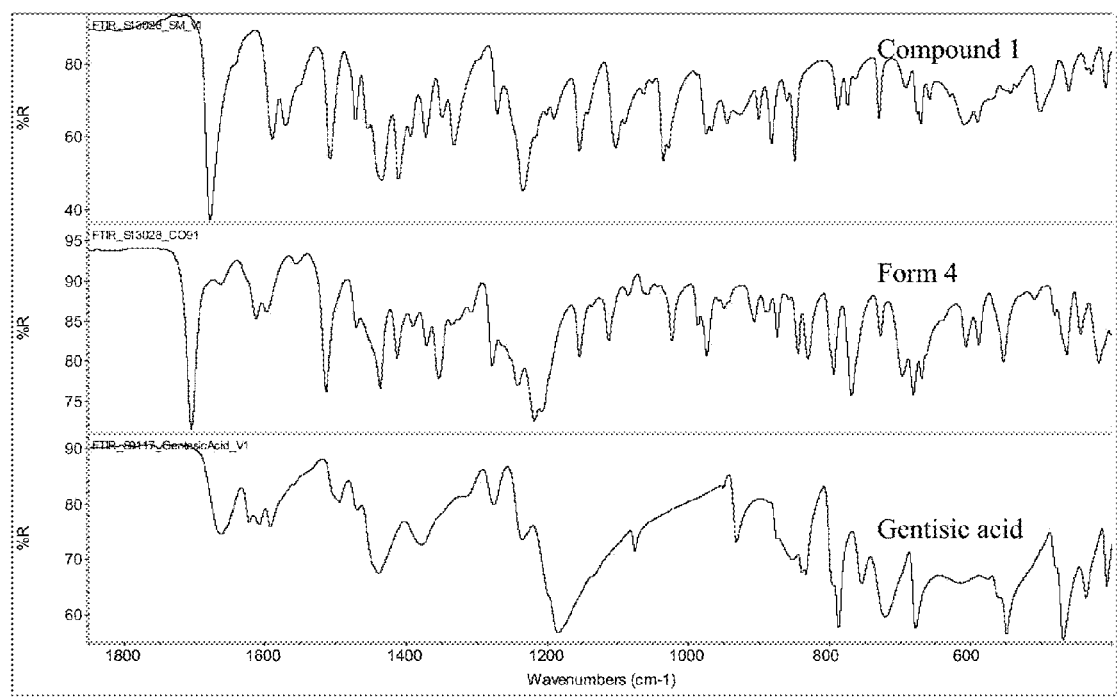
FIG. 23 depicts a FTIR overlay of Compound 1, Form 4 and gentisic acid in the region of 1800-400 $cm^{-1}$.

FIG. 23 provides an FTIR overlay of the starting material Compound 1 (blue), Form 4 (red) and gentisic acid (green) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.3.9 Cocrystal Solid Form 5

Form 5 was prepared in cooling evaporative experiments when gentisic acid was used as coformer and methanol was used as solvent. Form 5 is a hydrated cocrystal form of Compound 1 and gentisic acid.

FIG. 18 provides an overlay of XRPD patterns of: Compound 1, Form 4, Form 5 and gentisic acid (from bottom to top). A list of X-Ray Diffraction Peaks for Form 5 of Compound 1 is provided below in Table 16.

TABLE 16

X-Ray Diffraction Peaks for Form 5

| Two-theta angle (°) | d Space (Å) | Relative Intensity (%) |
|---|---|---|
| 10.82 | 8.17 | 17.72 |
| 16.9 | 5.24 | 9.12 |
| 17.42 | 5.08 | 60.71 |
| 19.3 | 4.59 | 22.22 |
| 24.7 | 3.6 | 89.63 |
| 28.34 | 3.15 | 33.09 |
| 30.86 | 2.89 | 29.05 |
| 37.58 | 2.39 | 14.42 |

FIG. 24 and FIG. 25 provide TGMS data and TGA/SDTA data of Form 5. A mass loss of 1.6% between approximately 35° C. and approximately 155° C. corresponding to water was observed during an endothermic event with $T_{peak}$ 180° C. suggesting the solvated nature of the sample. According to the SDTA signal in FIG. 25, an endothermic melt event was observed at 194° C., followed by immediate decomposition at 236° C.

Figure 26:
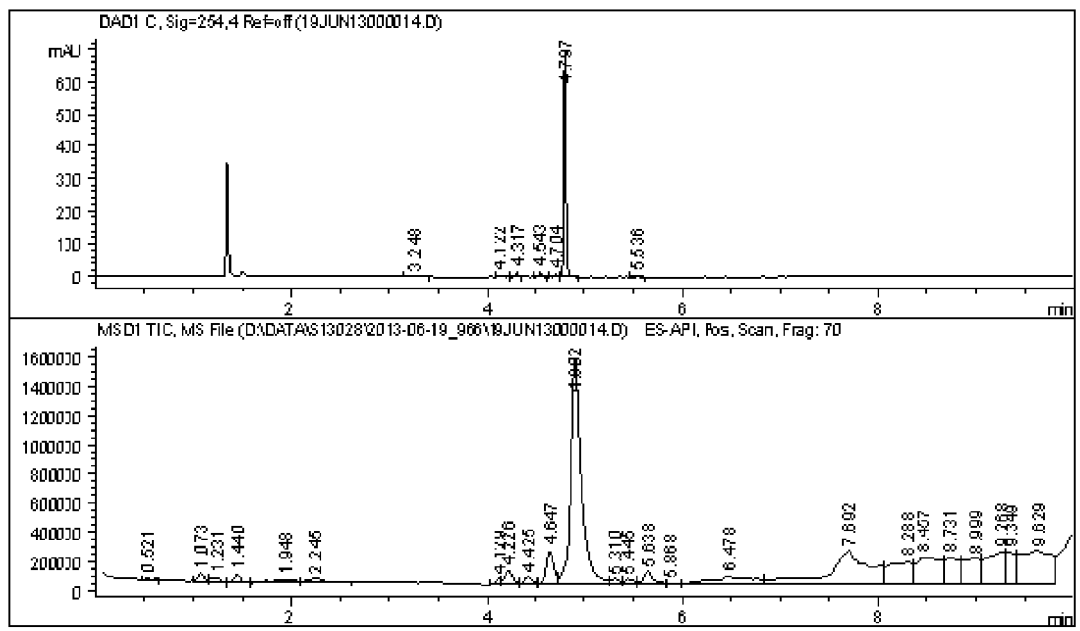
FIG. 26 depicts high performance liquid chromatography coupled with mass spectrometry of Form 5.

FIG. 26 provides HPLC and MS data of Form 5. The peak retention time is 4.8 minutes. The HPLC data indicates that the sample purity is 92.0% (area %).

Figure 27:
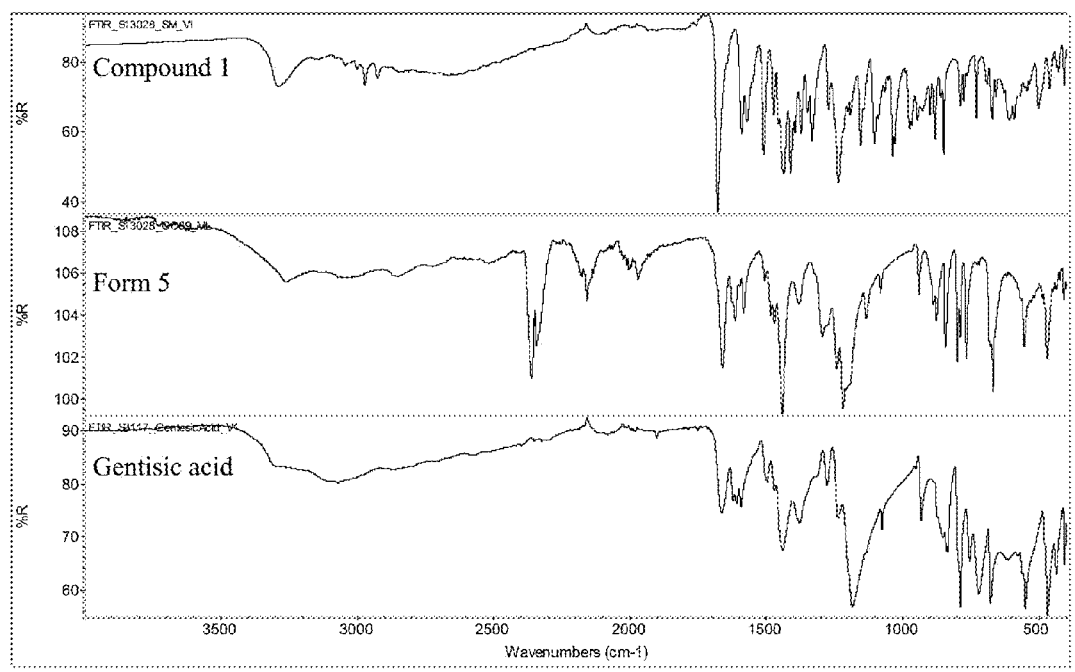
FIG. 27 depicts a FTIR overlay of Compound 1, Form 5 and gentisic acid.

FIG. 27 provides an FTIR overlay of the starting material Compound 1 (blue), Form 5 (red) and gentisic acid (green). The overlay indicates that the main shifts take place in the spectra in the region 1800-1500 cm$^{-1}$ and 1600-1400 cm$^{-1}$.

Figure 28:
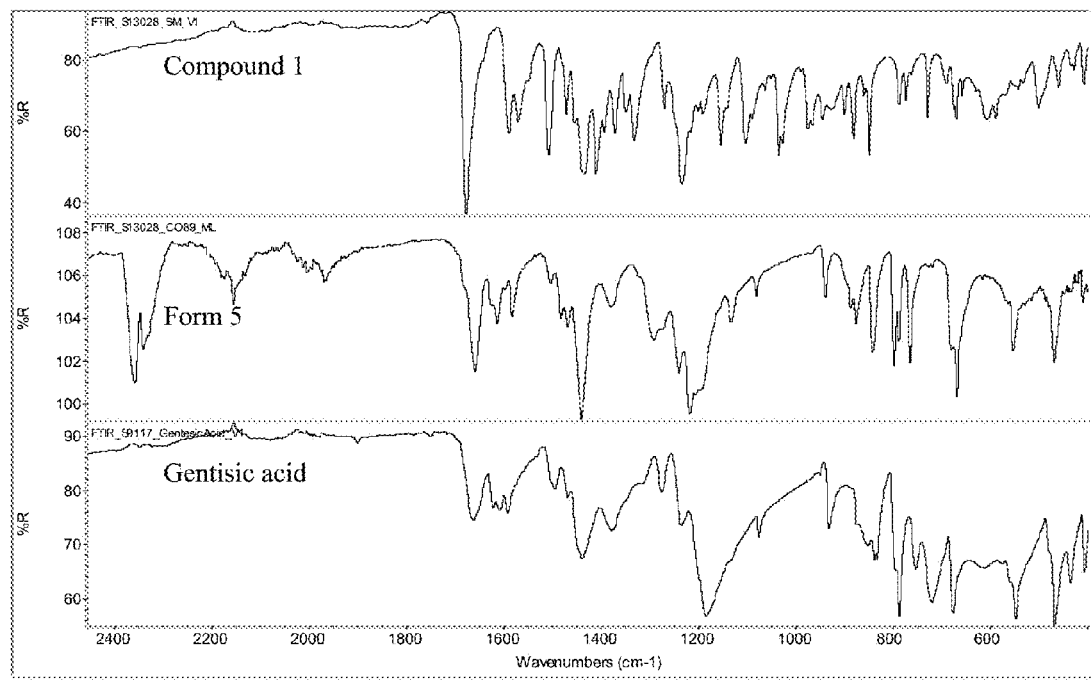
FIG. 28 depicts a FTIR overlay of Compound 1, Form 5 and gentisic acid in the region of 1800-400 $cm^{-1}$.

FIG. 28 provides an FTIR overlay of the starting material Compound 1 (blue), Form 5 (red) and gentisic acid (green) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.3.10 Cocrystal Solid Form 6

Form 6 was prepared in grinding experiments when nicotinamide was used as coformer and the mixture of THF and water (50/50) was used as solvent. Form 6 is a THF/water solvated cocrystal form of Compound 1 and nicotinamide.

FIG. 29 provides an overlay of XRPD patterns of: Compound 1, Form 6 and nicotinamide (from bottom to top). A list of X-Ray Diffraction Peaks for Form 6 of Compound 1 is provided below in Table 17.

TABLE 17

X-Ray Diffraction Peaks for Form 6

| Two-theta angle (°) | d Space (Å) | Relative Intensity (%) |
|---|---|---|
| 6.02 | 14.66 | 20.63 |
| 7.46 | 11.84 | 20.21 |
| 11.5 | 7.69 | 81.85 |
| 13.3 | 6.65 | 11.43 |
| 14.9 | 5.94 | 39.22 |
| 18.66 | 4.75 | 16.2 |
| 20.38 | 4.35 | 18.72 |
| 23.42 | 3.79 | 82.75 |
| 24.18 | 3.68 | 47.45 |
| 25.06 | 3.55 | 80.21 |
| 26.1 | 3.41 | 24.4 |
| 26.9 | 3.31 | 16.32 |
| 27.98 | 3.19 | 16.91 |
| 28.78 | 3.1 | 17.38 |

FIG. 30 provides TGMS data of Form 6. A mass loss of 3.8% corresponding to THF and water was observed during a double endothermic event with $T_{peak}$ 115.7° C. and 133.8° C., suggesting the solvated nature of the sample. According to the SDTA signal in FIG. 31, an endothermic melt event was observed at the above mentioned temperatures, 115.7° C. and 133.8° C., followed by immediate decomposition at 200° C.

Figure 32:
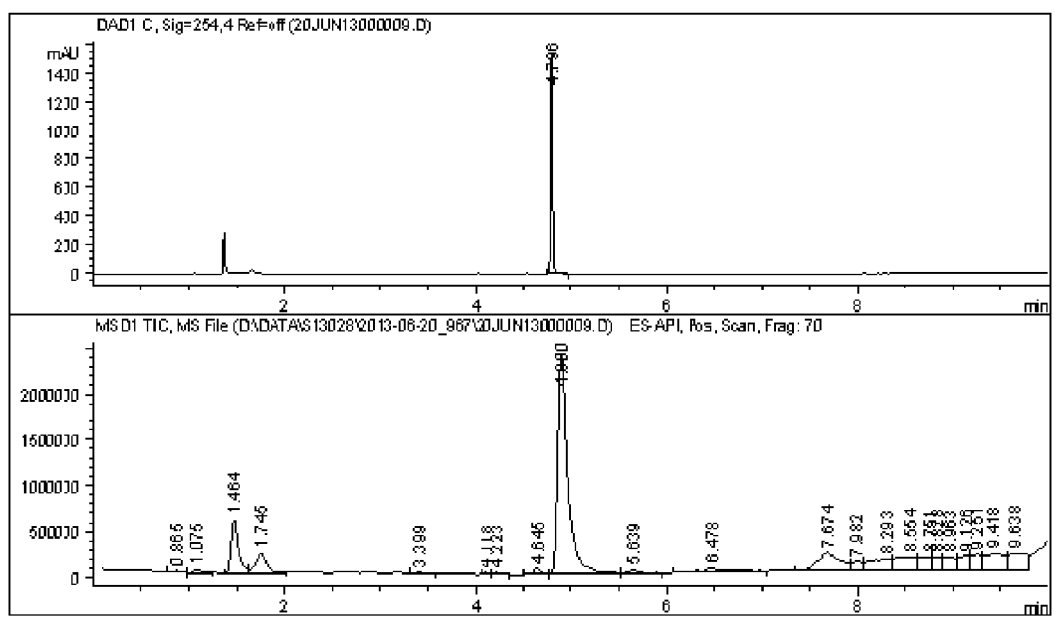
FIG. 32 depicts high performance liquid chromatography coupled with mass spectrometry of Form 6.

FIG. 32 provides HPLC and MS data of Form 6. The peak retention time is 4.8 minutes. The HPLC data indicates that the sample purity is 100.0% (area %).

Figure 33:
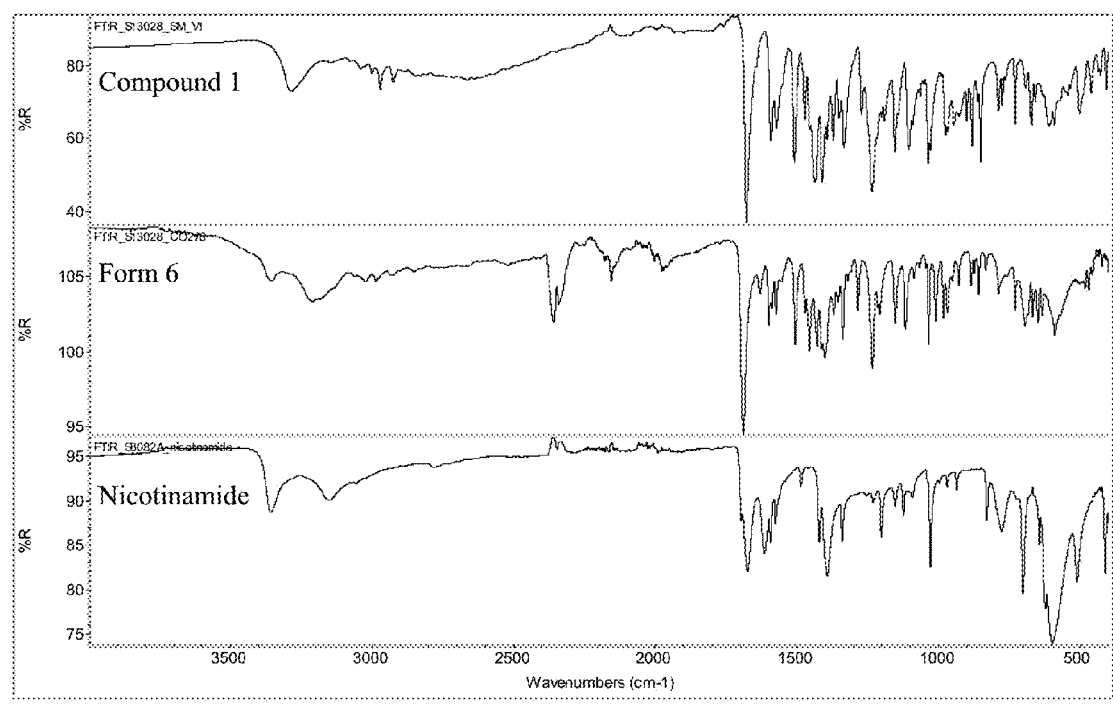
FIG. 33 depicts a fourier transform infrared spectroscopy (FTIR) overlay of Compound 1, Form 6 and nicotinamide.

FIG. 33 provides an FTIR overlay of the starting material Compound 1 (blue), Form 6 (red) and nicotinamide (green). The overlay indicates that the main shifts take place in the spectra in the region 1800-1500 cm$^{-1}$ and 1600-1400 cm$^{-1}$.

Figure 34:
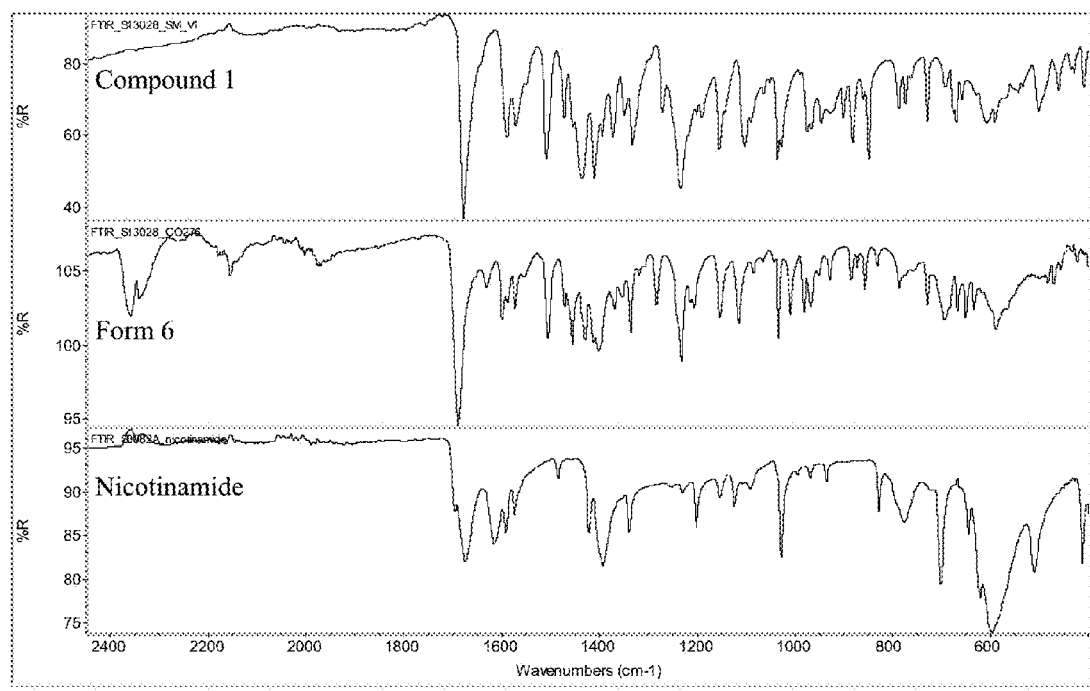
FIG. 34 depicts a FTIR overlay of Compound 1, Form 6 and nicotinamide in the region of 1800-400 $cm^{-1}$.

FIG. 34 provides an FTIR overlay of the starting material Compound 1 (blue), Form 6 (red) and nicotinamide (green) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.3.11 Cocrystal Solid Form 7

Form 7 was prepared in grinding experiments when succinic acid was used as coformer and the mixture of methonal and water (50/50) was used as solvent. Form 7 is a hydrated cocrystal form of Compound 1 and succinic acid.

FIG. 35 provides an overlay of XRPD patterns of: Compound 1, Form 7 and succinic acid (from bottom to top). A list of X-Ray Diffraction Peaks for Form 7 of Compound 1 is provided below in Table 18.

TABLE 18

X-Ray Diffraction Peaks for Form 7

| Two-theta angle (°) | d Space (Å) | Relative Intensity (%) |
|---|---|---|
| 7.62 | 11.59 | 72.94 |
| 10.54 | 8.38 | 31.45 |
| 13.82 | 6.4 | 24.43 |
| 17.46 | 5.07 | 18.19 |
| 17.94 | 4.94 | 16.96 |
| 19.34 | 4.58 | 18.39 |
| 24.26 | 3.66 | 23.69 |
| 26.7 | 3.33 | 82.32 |
| 27.38 | 3.25 | 11.54 |

FIG. 36 provides TGMS data of Form 7. A mass loss of 3.8% corresponding to water was observed during an endothermic event with $T_{peak}$ 108.8° C., suggesting the solvated nature of the sample. According to the SDTA signal in FIG. 37, another endothermic melt event was observed at 163.4° C., followed by immediate decomposition.

Figure 38:
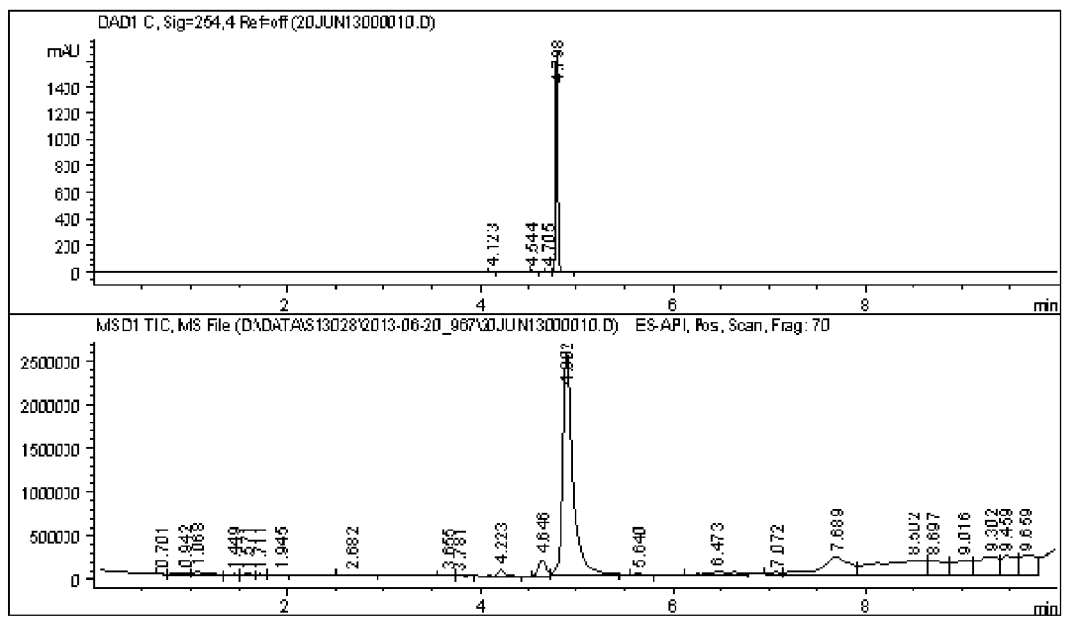
FIG. 38 depicts high performance liquid chromatography coupled with mass spectrometry of Form 7.

FIG. 38 provides HPLC and MS data of Form 7. The peak retention time is 4.8 minutes. The HPLC data indicates that the sample purity is 98.8% (area %).

Figure 39:
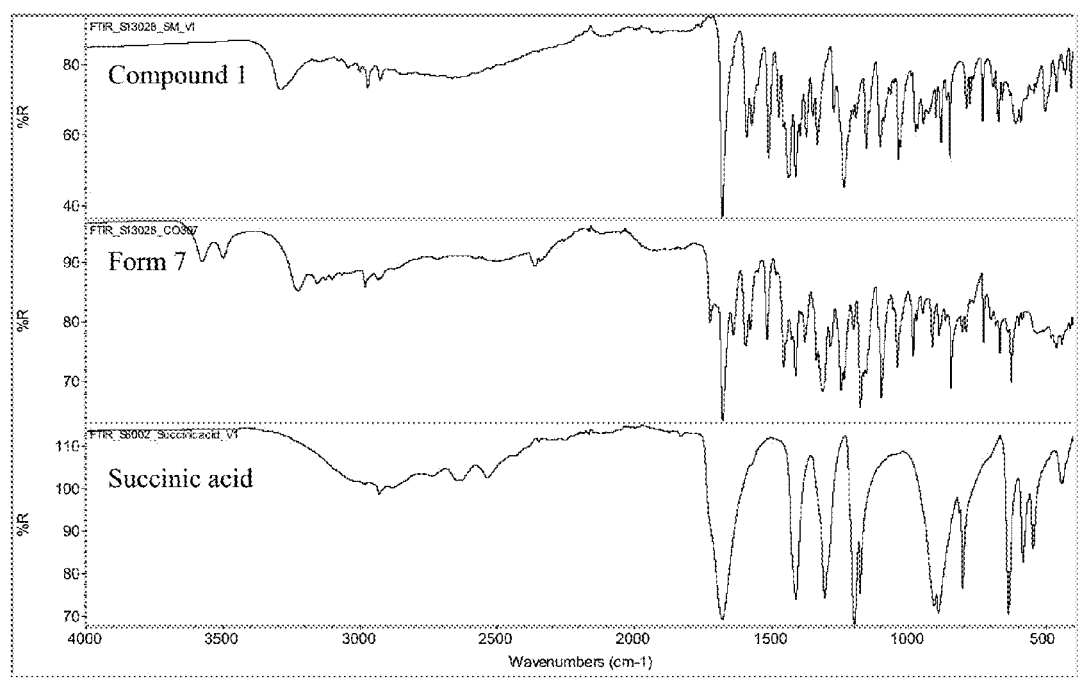
FIG. 39 depicts a fourier transform infrared spectroscopy (FTIR) overlay of Compound 1, Form 7 and succinic acid.

FIG. 39 provides an FTIR overlay of the starting material Compound 1 (blue), Form 7 (red) and succinic acid (green). The overlay indicates that the main shifts take place in the spectra in the region 1800-1500 cm$^{-1}$ and 1600-1400 cm$^{-1}$.

Figure 40:
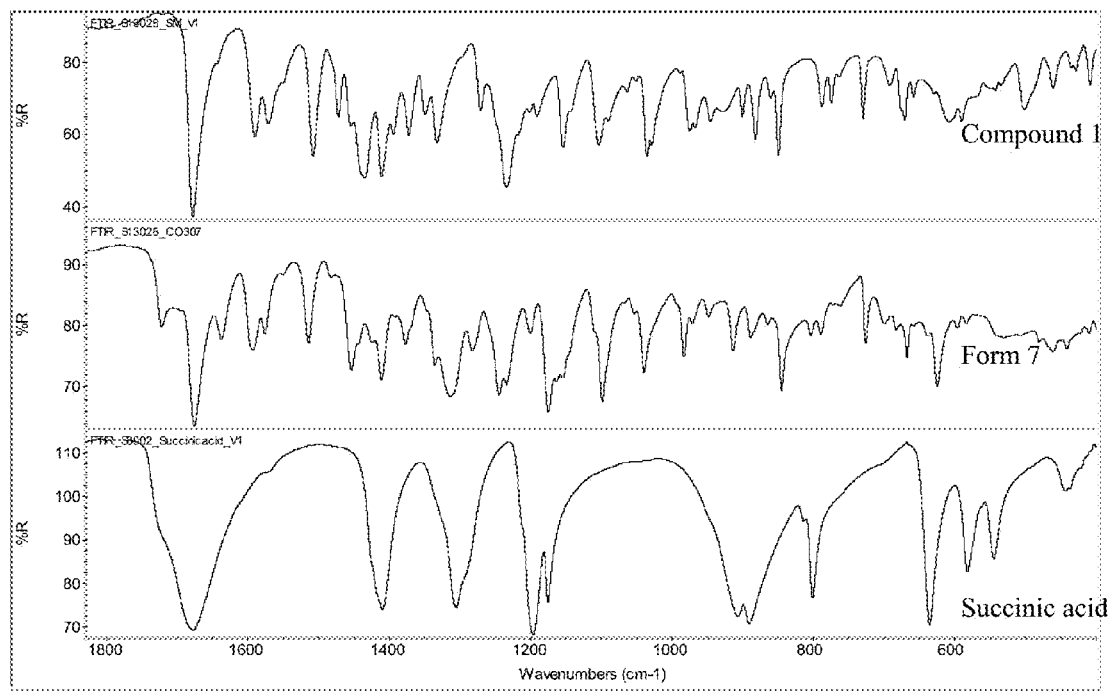
FIG. 40 depicts a FTIR overlay of Compound 1, Form 7 and succinic acid in the region of 1800-400 $cm^{-1}$.

FIG. 40 provides an FTIR overlay of the starting material Compound 1 (blue), Form 7 (red) and succinic acid (green) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.3.12 Cocrystal Solid Form 8

Form 8 was prepared in grinding experiments when maleic acid was used as coformer and the mixture of methonal and water (50/50) was used as solvent. Form 8 is a hydrated cocrystal form of Compound 1 and maleic acid.

FIG. 41 provides an overlay of XRPD patterns of: Compound 1, Form 8 and succinic acid (from bottom to top). A list of X-Ray Diffraction Peaks for Form 8 of Compound 1 is provided below in Table 19.

TABLE 19

X-Ray Diffraction Peaks for Form 8

| Two-theta angle (°) | d Space (Å) | Relative Intensity (%) |
|---|---|---|
| 6.94 | 12.72 | 43.53 |
| 12.54 | 7.05 | 12.02 |
| 13.82 | 6.4 | 91.12 |
| 16.54 | 5.35 | 14.71 |
| 20.82 | 4.26 | 7.88 |
| 22.18 | 4 | 29.97 |
| 22.78 | 3.9 | 27.37 |
| 24.46 | 3.63 | 27.58 |
| 26.22 | 3.39 | 33.82 |
| 26.98 | 3.3 | 38.32 |
| 27.66 | 3.22 | 59.4 |
| 28.7 | 3.11 | 11 |
| 29.66 | 3.01 | 12.33 |

FIG. 42 provides TGMS data of Form 8. A mass loss of 4.6% corresponding to water was observed during an endothermic event with $T_{peak}$ 118.7° C., suggesting the solvated nature of the sample. According to the SDTA signal in FIG. 43, the endothermic event was followed by immediate decomposition.

Figure 44:
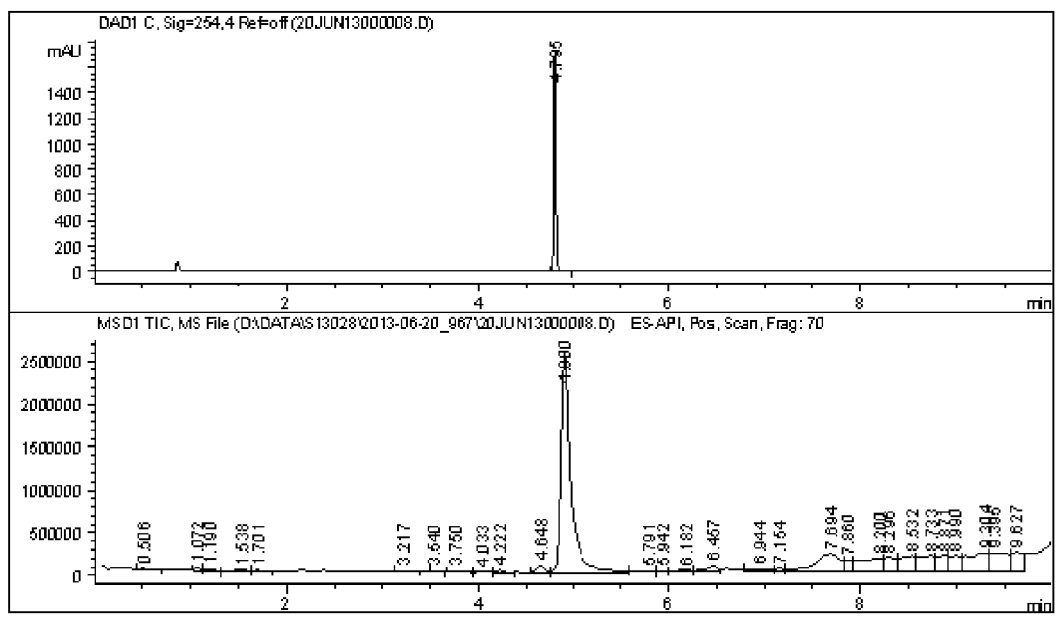
FIG. 44 depicts high performance liquid chromatography coupled with mass spectrometry of Form 8.

FIG. 44 provides HPLC and MS data of Form 8. The peak retention time is 4.8 minutes. The HPLC data indicates that the sample purity is 100.0% (area %).

Figure 45:
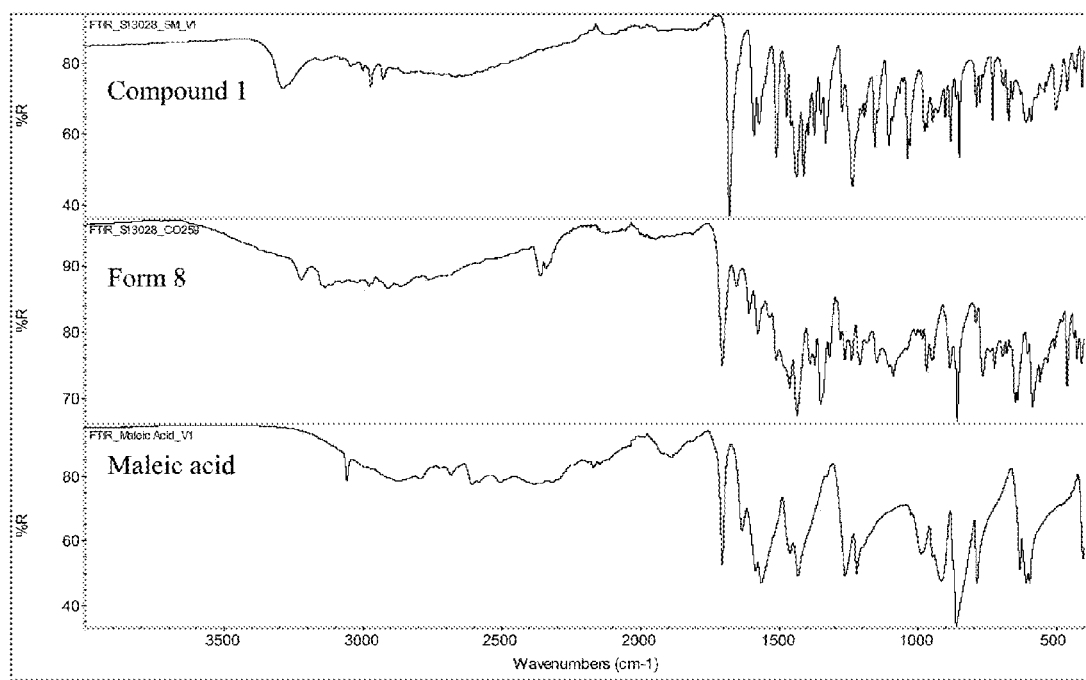
FIG. 45 depicts a fourier transform infrared spectroscopy (FTIR) overlay of Compound 1, Form 8 and maleic acid.

FIG. 45 provides an FTIR overlay of the starting material Compound 1 (blue), Form 8 (red) and maleic acid (green). The overlay indicates that the main shifts take place in the spectra in the region 1800-1500 cm$^{-1}$ and 1600-1400 cm$^{-1}$.

Figure 46:
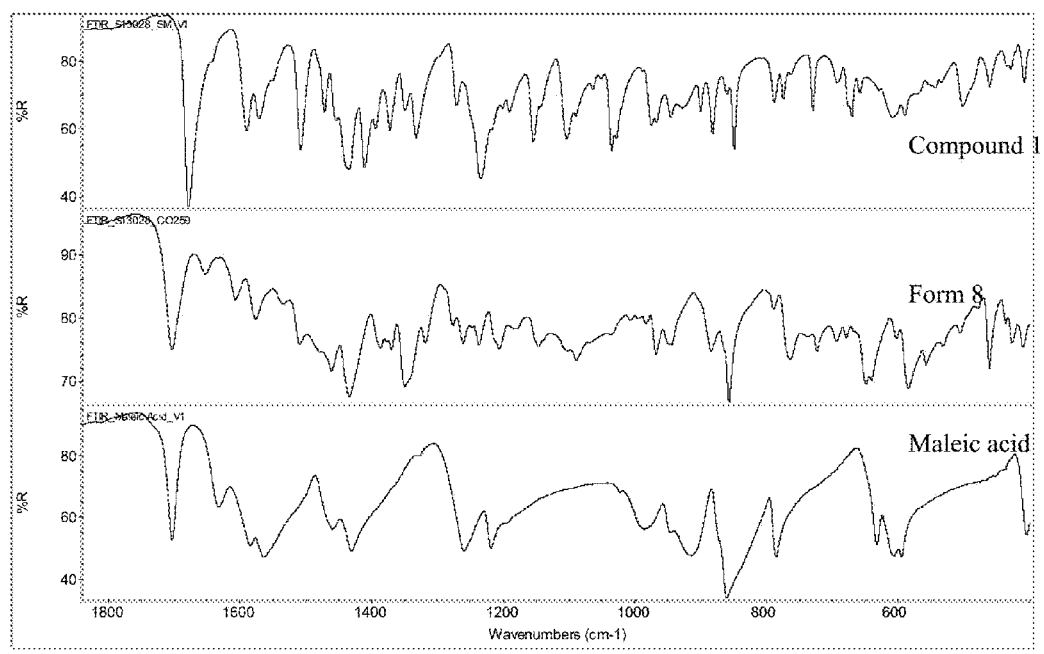
FIG. 46 depicts a FTIR overlay of Compound 1, Form 8 and maleic acid in the region of 1800-400 $cm^{-1}$.

FIG. 46 provides an FTIR overlay of the starting material Compound 1 (blue), Form 8 (red) and maleic acid (green) in the region of 1800-400 cm$^{-1}$. The overlay emphasizes the area between 1800-1500 cm$^{-1}$ and 1600-1400 cm$^{-1}$ corresponding to tertiary amines shifts where the H-bonding is taking place between the coformer and Compound 1.

6.4 Biological Examples

6.4.1 Biochemical Assays

TOR HTR-FRET Assay. The following is an example of an assay that can be used to determine the TOR kinase inhibitory activity of solid forms of Compound 1. A solid form of Compound 1 is dissolved in DMSO and prepared as 10 mM stocks and diluted appropriately for the experiments. Reagents are prepared as follows:

"Simple TOR buffer" (used to dilute high glycerol TOR fraction): 10 mM Tris pH 7.4, 100 mM NaCl, 0.1% Tween-20, 1 mM DTT. Invitrogen recombinant TOR enzyme (cat# PV4753) is diluted in this buffer to an assay concentration of 0.200 µg/mL.

ATP/Substrate solution: 0.075 mM ATP, 12.5 mM MnCl$_2$, 50 mM Hepes, pH 7.4, 50 mM β-GOP, 250 nM Microcystin LR, 0.25 mM EDTA, 5 mM DTT, and 3.5 µg/mL GST-p70S6.

Detection reagent solution: 50 mM HEPES, pH 7.4, 0.01% Triton X-100, 0.01% BSA, 0.1 mM EDTA, 12.7 µg/mL Cy5-αGST Amersham (Cat#PA92002V), 9 ng/mL α-phospho p70S6 (Thr389) (Cell Signaling Mouse Monoclonal #9206L), 627 ng/mL α-mouse Lance Eu (Perkin Elmer Cat#AD0077).

To 20 µL of the Simple TOR buffer is added 0.5 µL of test solid form in DMSO. To initiate the reaction 5 µL of ATP/Substrate solution is added to 20 µL of the Simple TOR buffer solution (control) and to the compound solution prepared above. The assay is stopped after 60 minutes by adding 5 µL of a 60 mM EDTA solution; 10 µL of detection reagent solution is then added and the mixture is allowed to sit for at least 2 hours before reading on a Perkin-Elmer Envision Microplate Reader set to detect LANCE Eu TR-FRET (excitation at 320 nm and emission at 495/520 nm).

DNA-PK Assay.

DNA-PK assay is performed using the procedures supplied in the Promega DNA-PK assay kit (catalog # V7870). DNA-PK enzyme can be purchased from Promega (Promega cat#V5811).

6.5 Formulation Examples

Certain formulations comprising solid forms of Compound 1 are prepared and tested for a number of physical and chemical properties. Modifications are made and subsequent formulations are also tested, until formulations possessing desirable physical and chemical properties are found. The following example describes these formulations and their testing.

Study 1:

A $2^{3-1}$ study evaluates the effect of diluents, disintegrant and drug loading on tablet physical properties and chemical stability. Examples of formulation compositions are shown in Table 20. Initial tablet development is carried out in normal room UV light.

TABLE 20

Exemplary Formulation Composition Of Various Tablet Formulations

| | | | | |
|---|---|---|---|---|
| Solid Form of Compound 1 (mg) | 0.5 | 0.5 | 5 | 5 |
| Microcrystalline Cellulose (mg) | 63.75 | 83.75 | 59.25 | 79.25 |
| Partially pregelatinized corn starch (mg) | | 10 | | 10 |
| Lactose monohydrate, spray dried (mg) | 30 | | 30 | |
| Crospovidone (mg) | | 4 | 4 | |
| Croscarmellose Na (mg) | 4 | | | 4 |
| Silicon dioxide (mg) | 1 | 1 | 1 | 1 |
| Magnesium Stearate (mg) | 0.75 | 0.75 | 0.75 | 0.75 |
| total uncoated tablet (mg) | 100 | 100 | 100 | 100 |
| Opadry II coating (mg) | 4 | 4 | 4 | 4 |
| total coated tablet (mg) | 104 | 104 | 104 | 104 |

Study 2:

A study is conducted to evaluate the effect of antioxidant (e.g., butylated hydroxyl toluene, BHT) and chelating agent (e.g., disodium edentate, Na$_2$-EDTA) on the stability of solid forms of Compound 1 in formulated product. The impact of dosage form (tablet vs capsule) on the stability of solid forms of Compound 1 is evaluated.

Examples of formulation compositions are shown in Table 21. All of the processes are carried out in dark.

TABLE 21

Exemplary Formulation Composition

| Ingredients | Capsule | Capsule | Capsule | Capsule | Tablet | Capsule |
|---|---|---|---|---|---|---|
| Solid Form of Compound 1 | 0.5 | 0.5 | 0.5 | 0.5 | 0.5 | 0.5 |
| Mannitol (Mannogem EZ) | 84 | 94.1 | | 93.6 | 83.6 | |
| MCC PH112 | 10 | | 94.1 | | 10 | |
| Lactose | | | | | | 93.6 |
| Sodium starch glycolate | 3 | 3 | 3 | 3 | 3 | 3 |
| stearic acid | 1 | 1 | 1 | 1 | 1 | 1 |
| Butylated hydroxy toluene | | 0.4 | 0.4 | 0.4 | 0.4 | 0.4 |
| Na$_2$-EDTA | 0.5 | | | 0.5 | 0.5 | 0.5 |
| Mg stearate | 1 | 1 | 1 | 1 | 1 | 1 |
| Total | 100 | 100 | 100 | 100 | 100 | 100 |

Study 3:

Further study can be conducted to study the influence of coating and desiccant on the stability of Compound 1 tablets. All processes can be carried out under yellow light to prevent any UV light exposure to the Compound 1 formulations.

An exemplary formulation composition is provided in Table 22.

TABLE 22

Exemplary Formulation Composition Of Tablet

| Ingredients | % w/w |
|---|---|
| Solid form of Compound 1 | 0.5 |
| Mannitol (Mannogem EZ) | 83.6 |
| MCC PH112 | 10 |
| Sodium starch glycolate | 3 |
| stearic acid | 1 |
| Butylated hydroxy toluene | 0.4 |
| Na$_2$-EDTA | 0.5 |
| Mg stearate | 1 |
| Total | 100 |

TABLE 23

Exemplary Tablet Formulations

| | % w/w (mg) Batch # | | | |
|---|---|---|---|---|
| Ingredients | 1 | 2 | 3 | 4 |
| Solid form of Compound 1 (active ingredient) | 10 | 10 | 10 | 10 |
| Mannitol (Mannogem EZ) | qs | qs | qs | qs |
| Microcrystalline Cellulose (PH 112) | 25 | 25 | 25 | 25 |
| Sodium Starch Glycolate | 3 | 3 | 3 | 3 |
| Silicon dioxide | 1 | 1 | 1 | 1 |
| Stearic acid | 0.5 | 0.5 | 0.5 | 0.5 |
| Disodium EDTA | | | 0.5 | 0.5 |
| BHT | | 0.4 | | 0.4 |
| Magnesium Stearate | 0.65 | 0.65 | 0.65 | 0.65 |
| Total | 100 | 100 | 100 | 100 |
| Color | Yellow | Yellow | Yellow | Yellow |

Preparation of Tablets:

The blends according to Table 24 to Table 29 are prepared as follows. Microcrystalline cellulose is weighed and added to an amber colored straight sided glass jar. The lid is closed and the jar is shakened in order to coat the inside of the jar. Active ingredient (solid form of Compound 1) is added and blended for 10 minutes at 46 rpm using a Turbula mixer. The blend is passed through a 25 mesh screen and blended again for 10 minutes at 46 rpm using a Turbula mixer. The resulting blend is passed through a 35 mesh screen. Remaining excipients are added, except for lubricant (magnesium stearate). The resulting mixture is blended for 10 minutes at 46 rpm using a Turbula mixer. 6 grams of the resulting blend is added an amber glass jar. Lubricant is added and blended for 1 minute and 35 seconds at 46 rpm using a Turbula mixer. For low strength tablet formulations, 140 mg tablets are prepared using a 7.14 mm punch and die. For high strength tablet formulations, 400 mg tablets are prepared using a 10.3 mm punch and die.

TABLE 24

Exemplary Low Strength Tablet Formulation #1

| Ingredient | Source | Amount (weight %) |
|---|---|---|
| Solid form of Compound 1 | | 0.7 |
| microcrystalline cellulose | FMC Biopolymer | 38.1 |
| Mannitol | Roquette | 57.2 |
| sodium carboxymethylcellulose | FMC Biopolymer | 3.0 |
| magnesium stearate | Nitika Chemicals | 1.0 |

TABLE 25

Exemplary Low Strength Tablet Formulation #2

| Ingredient | Source | Amount (weight %) |
|---|---|---|
| Solid form of Compound 1 | | 0.7 |
| microcrystalline cellulose | FMC Biopolymer | 75.3 |
| pregelatinized starch | Colorcon | 20.0 |
| sodium carboxymethylcellulose | FMC Biopolymer | 3.0 |
| magnesium stearate | Nitika Chemicals | 1.0 |

TABLE 26

Exemplary Low Strength Tablet Formulation #3

| Ingredient | Source | Amount (weight %) |
|---|---|---|
| Solid form of Compound 1 | | 0.7 |
| microcrystalline cellulose | FMC Biopolymer | 38.1 |
| Lactose monohydrate | Meggle Pharma | 57.2 |
| sodium carboxymethylcellulose | FMC Biopolymer | 3.0 |
| magnesium stearate | Nitika Chemicals | 1.0 |

TABLE 27

Exemplary High Strength Tablet Formulation #1

| Ingredient | Source | Amount (weight %) |
|---|---|---|
| Solid form of Compound 1 | | 25.0 |
| microcrystalline cellulose | FMC Biopolymer | 28.4 |
| Mannitol | Roquette | 42.6 |
| sodium carboxymethylcellulose | FMC Biopolymer | 3.0 |
| magnesium stearate | Nitika Chemicals | 1.0 |

TABLE 28

Exemplary High Strength Tablet Formulation #2

| Ingredient | Source | Amount (weight %) |
|---|---|---|
| Solid form of Compound 1 | | 25.0 |
| microcrystalline cellulose | FMC Biopolymer | 51.0 |
| pregelatinized starch | Colorcon | 20.0 |
| sodium carboxymethylcellulose | FMC Biopolymer | 3.0 |
| magnesium stearate | Nitika Chemicals | 1.0 |

TABLE 29

Exemplary High Strength Tablet Formulation #3

| Ingredient | Source | Amount (weight %) |
|---|---|---|
| Solid form of Compound 1 | | 25.0 |
| microcrystalline cellulose | FMC Biopolymer | 28.4 |
| Lactose monohydrate | Meggle Pharma | 42.6 |
| sodium carboxymethylcellulose | FMC Biopolymer | 3.0 |
| magnesium stearate | Nitika Chemicals | 1.0 |

The above formulations are subjected to a 6 week stability study.

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A solid form comprising (a) 1-ethyl-7-(2-methyl-6-(1H-1,2,4-triazol-3-yl)pyridin-3-yl)-3,4-dihydropyrazino[2,3-b]pyrazin-2(1H)-one; and (b) a coformer selected from the group consisting of gentisic acid and nicotinamide.

2. The solid form of claim 1, wherein the coformer is gentisic acid.

3. The solid form of claim 1, wherein the coformer is nicotinamide.

4. The solid form of claim 1, which is greater than 80% by weight of a crystal form.

5. The solid form of claim 4, which is greater than 80% by weight of a cocrystal.

6. The solid form of claim 5, which is greater than 90% by weight of a cocrystal.

7. The solid form of claim 6, which is greater than 95% by weight of a crystal form.

8. The solid form of claim 7, which contains less than 3% by weight of other solid forms of 1-ethyl-7-(2-methyl-6-(1H-1,2,4-triazol-3-yl)pyridin-3-yl)-3,4-dihydropyrazino[2,3-b]pyrazin-2(1H)-one.

9. The solid form of claim 8, further comprising amorphous 1-ethyl-7-(2-methyl-6-(1H-1,2,4-triazol-3-yl)pyridin-3-yl)-3,4-dihydropyrazino[2,3-b]pyrazin-2(1H)-one.

10. The solid form of claim 9, which is greater than 99% by weight of a crystal form.

11. A pharmaceutical composition comprising the solid form of claim 1, and a pharmaceutically acceptable excipient or carrier.

12. The pharmaceutical composition of claim 11, which is a single unit dosage form.

13. The pharmaceutical composition of claim 12, which is a tablet.

14. The pharmaceutical composition of claim 12, which is a capsule.

* * * * *